US012703691B2

(12) United States Patent
Fleming et al.

(10) Patent No.: US 12,703,691 B2
(45) Date of Patent: Aug. 11, 2026

(54) PHD INHIBITOR COMPOUNDS, COMPOSITIONS, AND THEIR USE

(71) Applicant: Akebia Therapeutics, Inc., Cambridge, MA (US)

(72) Inventors: Paul E. Fleming, Cambridge, MA (US); Thomas P. Blaisdell, Cambridge, MA (US); Senkara Rao Allu, Cambridge, MA (US)

(73) Assignee: Akebia Therapeutics, Inc., Cambridge, MA (US)

( * ) Notice: Subject to any disclaimer, the term of this patent is extended or adjusted under 35 U.S.C. 154(b) by 845 days.

(21) Appl. No.: 17/906,653

(22) PCT Filed: Mar. 19, 2021

(86) PCT No.: PCT/US2021/023228
§ 371 (c)(1),
(2) Date: Sep. 19, 2022

(87) PCT Pub. No.: WO2021/188944
PCT Pub. Date: Sep. 23, 2021

(65) Prior Publication Data

US 2023/0212138 A1 Jul. 6, 2023

Related U.S. Application Data

(60) Provisional application No. 62/992,616, filed on Mar. 20, 2020.

(51) Int. Cl.
*C07D 401/04* (2006.01)
*C07D 401/14* (2006.01)
*C07D 413/14* (2006.01)
*C07D 417/14* (2006.01)

(52) U.S. Cl.
CPC ......... *C07D 401/04* (2013.01); *C07D 401/14* (2013.01); *C07D 413/14* (2013.01); *C07D 417/14* (2013.01); *C07B 2200/05* (2013.01)

(58) Field of Classification Search
CPC .. C07D 401/04; C07D 401/14; C07D 413/14; C07D 417/14
See application file for complete search history.

(56) References Cited

U.S. PATENT DOCUMENTS

| | | | |
|---|---|---|---|
| 4,663,327 | A | 5/1987 | Sasse et al. |
| 4,698,344 | A | 10/1987 | Sasse et al. |
| 4,772,608 | A | 9/1988 | Sasse et al. |
| 5,175,176 | A | 12/1992 | Sasse et al. |
| 5,620,995 | A | 4/1997 | Weidmann et al. |
| 7,811,595 | B2 | 10/2010 | Kawamoto et al. |
| 8,323,671 | B2 | 12/2012 | Wu et al. |
| 8,343,952 | B2 | 1/2013 | Wu et al. |
| 8,524,699 | B2 | 9/2013 | Kai et al. |
| 8,598,210 | B2 | 12/2013 | Kawamoto et al. |
| 8,722,895 | B2 | 5/2014 | Kawamoto et al. |
| 8,940,773 | B2 | 1/2015 | Kawamoto et al. |
| 9,040,522 | B2 | 5/2015 | Brown et al. |
| 9,168,249 | B2 | 10/2015 | Thede et al. |
| 9,598,370 | B2 | 3/2017 | Kawamoto et al. |
| 10,729,681 | B2 | 8/2020 | Kawamoto et al. |
| 11,426,393 | B2 | 8/2022 | Kawamoto et al. |
| 11,883,386 | B2 | 1/2024 | Kawamoto et al. |
| 2012/0309977 | A1 | 12/2012 | Lanthier et al. |
| 2012/0322772 | A1 | 12/2012 | Flamme et al. |
| 2023/0159489 | A1 | 5/2023 | Fleming et al. |
| 2023/0227426 | A1 | 7/2023 | Fleming et al. |
| 2024/0358691 | A1 | 10/2024 | Kawamoto et al. |

FOREIGN PATENT DOCUMENTS

| | | | |
|---|---|---|---|
| CN | 101213189 | A | 7/2008 |
| CN | 101541785 | A | 9/2009 |
| CN | 101600710 | B3 | 12/2009 |
| CN | 101631785 | B4 | 1/2010 |

(Continued)

OTHER PUBLICATIONS

Tanaka (Bioorganic & Medicinal Chemistry 28 (2020) 115182, available online Nov. 9, 2019) (Year: 2019).*
International Search Report for PCT/US2021/023219 dated Jul. 6, 2021 (6 pages).
International Search Report for PCT/US2021/023222 dated Jul. 6, 2021 (5 pages).
International Search Report for PCT/US2021/023228 dated Jun. 28, 2021 (10 pages).
"4-[2-(5-acetylpyridin-2-yl)-3-oxo-1H-pyrazol-4-yl]benzonitrile", PubChem, National Center for Biotechnology Information, CID 135129723, Dec. 15, 2018 from URL: https://pubchem.ncbi.nlm.nih.gov/compound/135129723 (10 pages).

(Continued)

*Primary Examiner* — Kortney L. Klinkel
*Assistant Examiner* — Richard Grant Peckham
(74) *Attorney, Agent, or Firm* — Proskauer Rose LLP

(57) ABSTRACT

The present invention provides, in part, novel small molecule inhibitors of PHD, having a structure according to Formula (A), and sub-formulas thereof: or a pharmaceutically acceptable salt thereof. The compounds provided herein can be useful for treatment of diseases including heart (e.g. ischemic heart disease, congestive heart failure, and valvular heart disease), lung (e.g., acute lung injury, pulmonary hypertension, pulmonary fibrosis, and chronic obstructive pulmonary disease), liver (e.g. acute liver failure and liver fibrosis and cirrhosis), and kidney (e.g. acute kidney injury and chronic kidney disease) disease.

(A)

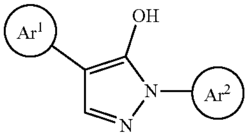

2 Claims, 1 Drawing Sheet

(56) References Cited

FOREIGN PATENT DOCUMENTS

| | | | | |
|---|---|---|---|---|
| CN | 105492433 B5 | 4/2016 | | |
| CN | 106831735 A | 6/2017 | | |
| CN | 109879804 A | 6/2019 | | |
| DE | 3443308 B6 | 5/1986 | | |
| DE | 102006050512 A1 | 4/2008 | | |
| DE | 102007044032 A1 | 3/2009 | | |
| EP | 3336084 A1 | 6/2018 | | |
| IN | 201621021801 A | 12/2017 | | |
| JP | S60255788 B7 | 12/1985 | | |
| JP | S61137878 B8 | 6/1986 | | |
| JP | 2008539180 A | 11/2008 | | |
| JP | 2010507602 A | 3/2010 | | |
| JP | 2010507605 A | 3/2010 | | |
| JP | 2012513976 A | 6/2012 | | |
| JP | 2016501882 A | 1/2016 | | |
| JP | 2016515582 A | 5/2016 | | |
| RU | 2469031 C2 | 12/2012 | | |
| TW | 200833330 A | 8/2008 | | |
| WO | WO 2006/114213 A1 | 11/2006 | | |
| WO | WO 2007/090068 A2 | 8/2007 | | |
| WO | WO 2008/002576 A2 | 1/2008 | | |
| WO | WO 2008/040002 A2 | 4/2008 | | |
| WO | WO 2008/067874 A1 | 6/2008 | | |
| WO | WO 2008/121861 A2 | 10/2008 | | |
| WO | 2010005851 A1 | 1/2010 | | |
| WO | 2010076524 A3 | 8/2010 | | |
| WO | WO 2013/134660 A1 | 9/2013 | | |
| WO | WO 2014/089364 A1 | 6/2014 | | |
| WO | WO-2014160810 A1 | * | 10/2014 | ........... A61K 31/444 |
| WO | WO 2016/148306 A1 | 9/2016 | | |
| WO | WO 2017/143131 A1 | 8/2017 | | |
| WO | WO 2021/188936 A1 | 9/2021 | | |
| WO | WO 2021 /188938 A1 | 9/2021 | | |
| WO | WO 2021/188944 A1 | 9/2021 | | |
| WO | WO 2021/216530 A1 | 10/2021 | | |
| WO | WO 2022/036188 A1 | 2/2022 | | |

OTHER PUBLICATIONS

Buchi, et al., "Synthesis and pharmacological properties of certain pyridylpyrazol-5-one", Helvetica Chimica Acta, vol. 49 (pp. 272-280) (10 pages).

Lee, et al., "Hypoxia signaling in human diseases and therapeutic targets", Experimental & Molecular Medicine, vol. 51, Jun. 20, 2019, pp. 1-13, DOI: 10.1038/s12276-019-0235-1, (13 pages).

Patani, et al. "Bioisosterism: A Rational Approach in Drug Design", Chemical Reviews, vol. 96, No. 8, 1996, pp. 3147-3176 DOI: 10.1021/cr950066q (30 pages).

U.S. Appl. No. 17/906,650, filed Sep. 19, 2022, Fleming et al.

U.S. Appl. No. 17/906,652, filed Sep. 19, 2022, Fleming et al.

U.S. Appl. No. 18/041,490, filed Feb. 13, 2023, Blaisdell et al.

Beck et al., "Discovery of Molidustat (BAY 85-3934): A Small-Molecule Oral HIF-Prolyl Hydroxylase (HIF-PH) Inhibitor for the Treatment of Renal Anemia", ChemMedChem, vol. 13, No. 10, Feb. 28, 2018, pp. 988-1003, DOI: 10.1002/cmdc.201700783, (16 pages).

Cadieux et al., "Synthesis and biological evaluation of substituted pyrazoles as blockers of divalent metal transporter 1 (DMT1)", Bioorganic & Medicinal Chemistry Letters, vol. 22. No. 1, Nov. 25, 2011, pp. 90-95, DOI: 10.1016/j.bmcl.2011.11.069, (6 pages).

Markham, Anthony, "Vadadustat: First Approval", Drugs, vol. 80, Aug. 27, 2020, pp. 1365-1371, DOI: 10.1007/s40265-020-01383-z, (7 pages).

Xue et al., "Prolyl Hydroxylase-3 is down regulated in colorectal cancer cells and inhibits IKKB independent of hydroxylase activity", Gastroenterology, vol. 138, No. 2, Feb. 2010, pp. 606-615, DOI: 10.1053/j.gastro.2009.09.049, (5 pages).

Compound with CAS Registry No. 5575-24-6. 2-(6-Chloro-2-pyridinyl)-1,2-dihydro-5- methyl-4-phenyl-3H-pyrazol-3-one. Nov. 16, 1984 (1 page).

Guillo, Sandrine, et al., "N-arylation of 3-alkoxypyrazoles, the case of the pyridines", Tetrahedron, vol. 66, No. 14, Apr. 3, 2010, pp. 2654-2663 (10 pages).

Laskaris, Paris, et al., "A Novel Polyaminocarboxylate Compound to Treat Murine Pulmonary Aspergillosis by Interfering with Zinc Metabolism", Antimicrobial Agents and Chemotherapy, vol. 62, No. 6, Jun. 1, 2018 (11 pages).

* cited by examiner

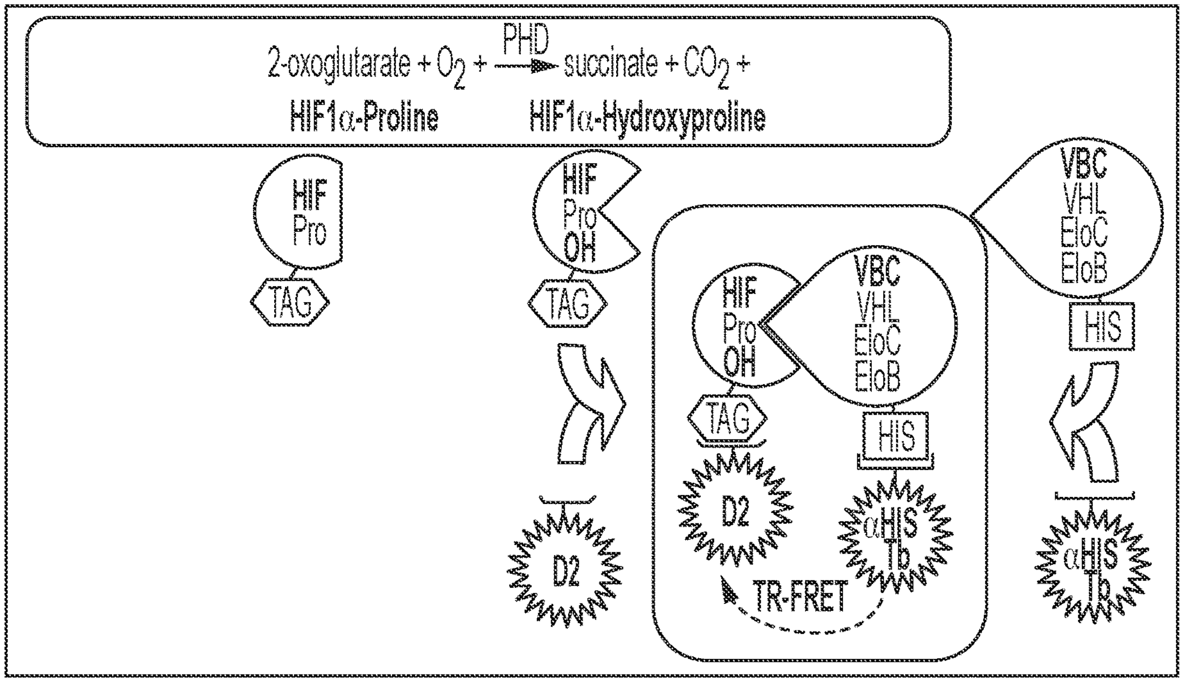

αHis-Tb: monoclonal antibody anti-6His-Terbium-cryptate Gold; $CO_2$: carbon dioxide; D2: streptavidin (SA)-D2 Acceptor; EloB: elongin B; EloC: elongin C; HIF-Pro: proline 564 of HIF; HIF-Pro-OH: HIF-1α-hydroxyproline 564; HIF-1α: hypoxia inducible factor 1 alpha; $O_2$: oxygen; PHD: prolyl-4-hydroxylase domain; PHD1: prolyl-4-hydroxylase domain 1; PHD2: prolyl-4-hydroxylase domain 2; PHD3: prolyl-4-hydroxylase domain 3; TR-FRET: time-resolved fluorescence resonance energy transfer; VBC: Von Hippel—Lindau protein, elongin B, elongin C complex; VHL: Von Hippel—Lindau

PHD INHIBITOR COMPOUNDS, COMPOSITIONS, AND THEIR USE

CROSS-REFERENCE TO RELATED APPLICATIONS

This application is a 35 U.S.C. § 371 National Stage Application of International Application No. PCT/US2021/023228, filed on Mar. 19, 2021, which claims priority to U.S. Provisional Patent Application No. 62/992,616, filed Mar. 20, 2020, which are hereby incorporated by reference in their entireties.

BACKGROUND

Hypoxia is a condition or state in which the supply of oxygen is insufficient for normal life function, for example, where there is low arterial oxygen supply. Hypoxia can lead to functional impairment of cells and structural tissue damage. The activation of cellular defense mechanisms during hypoxia is mediated by HIF (Hypoxia-inducible factor) protein. In response to hypoxic conditions, levels of HIFα are elevated in most cells because of a decrease in HIFα prolyl hydroxylation. Prolyl hydroxylation of HIFα is accomplished by a family of proteins variously termed the prolyl hydroxylase domain-containing proteins (PHD1, 2, and 3), also known as HIF prolyl hydroxylases (HPH-3, 2, and 1) or EGLN-2, 1, and 3. The PHD proteins are oxygen sensors and regulate the stability of HIF in an oxygen dependent manner. The three PHD isoforms function differently in their regulation of HIF and may have other non-HIF related regulatory roles.

In fact, many studies demonstrate that stabilization of HIF can dampen tissue inflammation and promote its repair. Accordingly, compounds that can inhibit the activity of PHD proteins may be particular beneficial in new therapies (Lee et al. (2019) Exp. Mol. Med. 51:68)

Described herein are novel small molecule PHD inhibitors that have utility for the treatment of disease including heart (e.g. ischemic heart disease, congestive heart failure, and valvular heart disease), lung (e.g., acute lung injury, pulmonary hypertension, pulmonary fibrosis, and chronic obstructive pulmonary disease), liver (e.g. acute liver failure and liver fibrosis and cirrhosis), and kidney (e.g. acute kidney injury and chronic kidney disease) disease.

SUMMARY

The present invention provides, among other things, novel small molecule inhibitors of PHD and have utility for the treatment of diseases, including but not limited to heart (e.g. ischemic heart disease, congestive heart failure, and valvular heart disease), lung (e.g., acute lung injury, pulmonary hypertension, pulmonary fibrosis, and chronic obstructive pulmonary disease), liver (e.g. acute liver failure and liver fibrosis and cirrhosis), and kidney (e.g. acute kidney injury and chronic kidney disease) disease.

In an aspect, provided herein are compounds having a structure according to Formula (A), (A)

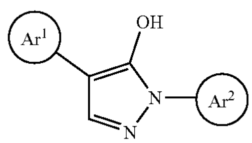

or a pharmaceutically acceptable salt thereof, wherein:

$Ar^1$ is aryl or heteroaryl, optionally substituted with one or more groups selected from halogen, CN, OH, $C_{1-3}$ alkyl optionally substituted with CN or one or more halogens, and $C_{1-3}$ alkoxy; and $Ar^2$ is pyrid-2-yl, optionally substituted with one or more groups selected from halogen; amino; amide; OH; a sulfonyl group; a sulfinyl group; a carbonyl group; a phosphoryl group; $C_{3-6}$ cycloalkyl; $C_{3-6}$ heterocycloalkyl optionally substituted with a sulfonyl group or =O; $C_{1-3}$ alkyl optionally substituted with carbonyl or one or more halogens; and heteroaryl optionally substituted with $C_{1-3}$ alkyl or phenyl.

In embodiments, $Ar^1$ is

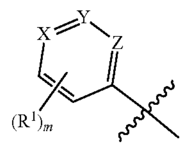

wherein

X is N or $CR^{1a}$;

Y and Z are independently CH or N;

$R^{1a}$ is H, CN, halogen, $C_{1-3}$ alkoxy, OH, or $C_{1-3}$ alkyl optionally substituted with CN;

$R^1$, each time taken, is independently selected from the group consisting of hydrogen, halogen, CN, OH, $C_{1-3}$ alkyl optionally substituted with one or more halogens, and $C_{1-3}$ alkoxy; and m is 1, 2, 3 or 4.

In embodiments, $Ar^1$ is

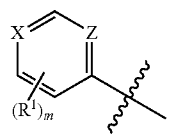

In embodiments, $Ar^1$ is

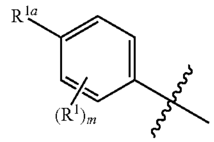

wherein $R^{1a}$ is H, CN, halogen, $C_{1-3}$ alkoxy, OH, or $C_{1-3}$ alkyl optionally substituted with CN.

In embodiments, $R^{1a}$ is H, CN, halogen, $C_{1-3}$ alkoxy, OH, or $C_{1-3}$ alkyl optionally substituted with CN.

In embodiments, $R^1$, each time taken, is independently selected from the group consisting of hydrogen, halogen, CN, OH, $C_{1-3}$ alkyl optionally substituted with one or more halogens, and $C_{1-3}$ alkoxy.

In embodiments, $Ar^2$ is

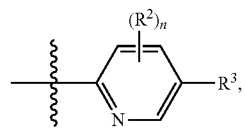

wherein $R^2$, each time taken, is independently selected from the group consisting of hydrogen, halogen, $NR^4R^5$, OH, $C_{1-3}$ alkyl, and $C_{3-6}$ cycloalkyl;

$R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens;

$R^6$ is $C_{1-3}$ alkyl, $NHCOR^{15}$, $NR^{16}R^{17}$, or phenyl;

$R^7$ is $C_{1-3}$ alkyl, $C_{3-5}$ cycloalkyl, phenyl, or $NR^{18}R^{19}$.

$R^8$ is NH or $NCH_3$;

$R^{10}$ is $C_{1-3}$ alkyl or $NHSO_2R^{20}$;

$R^{11}$ is $COR^{21}$ or $SO_2R^{22}$;

$R^9$, $R^{12}$, $R^{13}$ $R^{14}$, $R^{15}$, and $R^{20}$ are each independently $C_{1-3}$ alkyl;

$R^{21}$ is heterocycloalkyl, cycloalkyl, or $C_{1-3}$ alkyl;

$R^{22}$ is $NR^{23}R^{24}$ or $C_{1-3}$ alkyl optionally substituted with carboxyl;

$R^4$, $R^5$, $R^{16}$, $R^{17}$, $R^{18}$, $R^{19}$, $R^{23}$ and $R^{24}$ are each independently H or $C_{1-3}$ alkyl;

p is 1, 2, or 3; and n is 0, 1, 2 or 3.

In embodiments, $Ar^2$ is

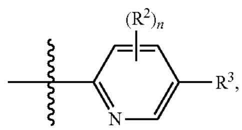

wherein $R^3$ is selected from the group consisting of F, Cl, Br, and I.

In embodiments, $Ar^2$ is

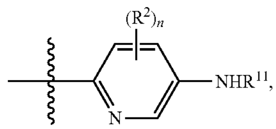

wherein $R^{11}$ is $COR^{21}$ or $SO_2R^{22}$; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; and $R^{23}$ and $R^{24}$ are independently H or $C_{1-3}$ alkyl.

In embodiments, $Ar^2$ is

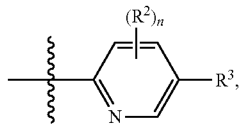

wherein $R^3$ is cycloalkyl or heterocycloalkyl optionally substituted with $SO_2R^{14}$ or =O; and $R^{14}$ is $C_{1-3}$ alkyl.

In embodiments, $Ar^2$ is

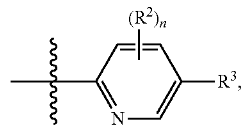

wherein $R^3$ is heteroaryl optionally substituted with $C_{1-3}$ alkyl or phenyl.

In embodiments, cycloalkyl or optionally substituted heterocycloalkyl is selected from the group consisting of

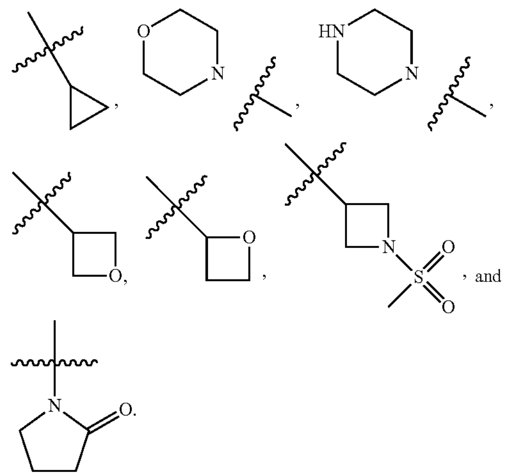

In embodiments, an optionally substituted heteroaryl is selected from the group consisting of

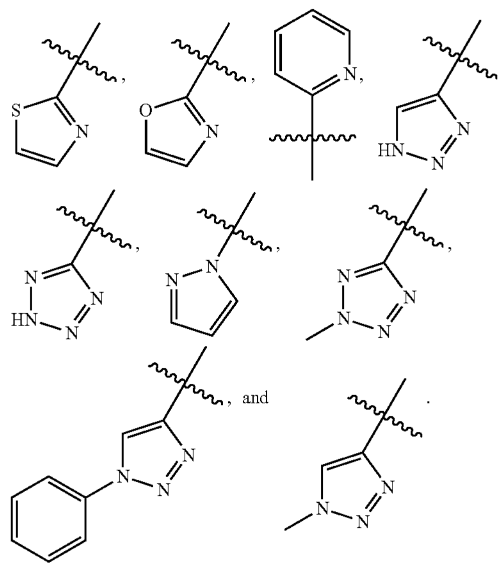

In embodiments, $R^2$, each time taken, is independently selected from the group consisting of hydrogen, halogen, $NR^4R^5$, OH, $C_{1-3}$ alkyl, and $C_{3-6}$ cycloalkyl, wherein $R^4$ and Rare each independently H or $C_{1-3}$ alkyl.

In embodiments, $R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens, wherein $R^6$ is $C_{1-3}$ alkyl, $NHCOR^{15}$, $NR^{16}R^{17}$, or phenyl; $R^7$ is $C_{1-3}$ alkyl, $C_{3-5}$ cycloalkyl, phenyl, or $NR^{18}R^{19}$; $R^8$ is NH or $NCH_3$; $R^{10}$ is $C_{1-3}$ alkyl or $NHSO_2R^{20}$; $R^{11}$ is $COR^{21}$ or $SO_2R^{22}$; $R^9$, $R^{12}$, $R^{13}$ $R^{14}$, $R^{15}$, and $R^{20}$ are each independently $C_{1-3}$ alkyl; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; $R^4$, $R^5$, $R^{16}$, $R^{17}$, $R^{18}$, $R^{19}$, $R^{23}$ and $R^{24}$ are each independently H or $C_{1-3}$ alkyl; and p is 1, 2, or 3.

In embodiments, a compound of Formula (A) has the following structure, (I)

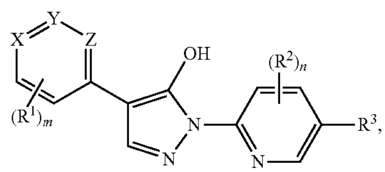

or a pharmaceutically acceptable salt thereof.

In embodiments of Formula (I), X is N or $CR^{1a}$; Y and Z are independently CH or N; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens; $R^4$ and $R^5$ are each independently H or $C_{1-3}$ alkyl; $R^6$ is $C_{1-3}$ alkyl, $NHCOR^{15}$, $NR^{16}R^{17}$, or phenyl; $R^7$ is $C_{1-3}$ alkyl, $C_{3-5}$ cycloalkyl, phenyl, or $NR^{H}R^{19}$ $R^8$ is NH or $NCH_3$; $R^9$ is $C_{1-3}$ alkyl; $R^{10}$ is $C_{1-3}$ alkyl or $NHSO_2R^{20}$; $R^{11}$ is $COR^{21}$ or $SO_2R^{22}$; $R^{12}$ and $R^{13}$ are each independently $C_{1-3}$ alkyl; $R^{14}$ is $C_{1-3}$ alkyl; $R^{15}$ is $C_{1-3}$ alkyl; $R^{16}$ and $R^{17}$ are each independently H or $C_{1-3}$ alkyl; $R^{18}$ and $R^{19}$ are each independently H or $C_{1-3}$ alkyl; $R^{20}$ is $C_{1-3}$ alkyl; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; $R^{23}$ and $R^{24}$ are each independently H or $C_{1-3}$ alkyl; m is 1, 2, 3, or 4; n is 0, 1, 2 or 3; and p is 1, 2, or 3.

In embodiments, a compound of Formula (A) or Formula (I) has the following structure, (II)

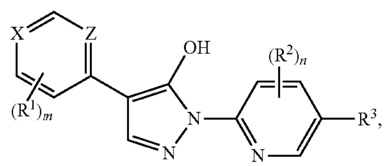

or a pharmaceutically acceptable salt thereof.

In embodiments, X is N or $CR^{1a}$; Z is CH or N; $R^1$, each time taken, is independently selected from the group consisting of hydrogen, halogen, CN, OH, $C_{1-3}$ alkyl optionally substituted one or more halogens, and $C_{1-3}$ alkoxy; Ria is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens; $R^4$ and $R^5$ are each independently H or $C_{1-3}$ alkyl; $R^6$ is $C_{1-3}$ alkyl, $NHCOR^{15}$, $NR^{16}R^{17}$, or phenyl; $R^7$ is $C_{1-3}$ alkyl, $C_{3-5}$ cycloalkyl, phenyl, or $NR^{18}R^{19}$; $R^8$ is NH or $NCH_3$; $R^9$ is $C_{1-3}$ alkyl; $R^{10}$ is $C_{1-3}$ alkyl or $NHSO_2R^{20}$; $R^{11}$ is $COR^{21}$ or $SO_2R^{22}$; $R^{12}$ and $R^{13}$ are each independently $C_{1-3}$ alkyl; $R^{14}$ is $C_{1-3}$ alkyl; $R^{15}$ is $C_{1-3}$ alkyl; $R^{16}$ and $R^{17}$ are independently H or $C_{1-3}$ alkyl; $R^{18}$ and $R^{19}$ are independently H or $C_{1-3}$ alkyl; $R^{20}$ is $C_{1-3}$ alkyl; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; $R^{23}$ and $R^{24}$ are independently H or $C_{1-3}$ alkyl; m is 1, 2, 3, or 4; n is 0, 1, 2 or 3; and p is 1, 2, or 3.

In embodiments, a compound of Formula (A), Formula (I), or Formula (II) has the following structure, (III)

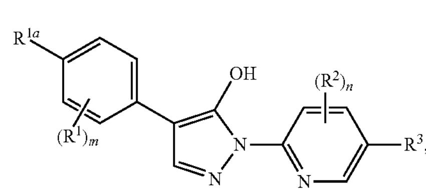

or a pharmaceutically acceptable salt thereof.

In embodiments of Formula (III), $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^3$ is $SO_2R^6$, $SOR^7R^8$, $SOR^9$, $COR^{10}$, $(CH_2)_pCOOH$, $NHR^{D}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens; $R^4$ and $R^5$ are each independently H or $C_{1-3}$ alkyl; $R^6$ is $C_{1-3}$ alkyl, $NHCOR^{15}$, $NR^{16}R^{17}$, or phenyl; $R^7$ is $C_{1-3}$ alkyl, $C_{3-5}$ cycloalkyl, phenyl, or $NR^{18}R^{19}$; $R^8$ is NH or $NCH_3$; $R^9$ is $C_{1-3}$ alkyl; $R^{10}$ is $C_{1-3}$ alkyl or $NHSO_2R^{20}$; $R^{11}$ is $COR^{21}$ or $SO_2R^{22}$; $R^{12}$ and $R^{13}$ are each independently $C_{1-3}$ alkyl; $R^{14}$ is $C_{1-3}$ alkyl; $R^{15}$ is $C_{1-3}$ alkyl; $R^{16}$ and $R^{17}$ are independently H or $C_{1-3}$ alkyl; $R^{18}$ and $R^{19}$ are independently H or $C_{1-3}$ alkyl; $R^{20}$ is $C_{1-3}$ alkyl; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; $R^{23}$ and $R^{24}$ are independently H or $C_{1-3}$ alkyl; m is 1, 2, 3, or 4; n is 0, 1, 2 or 3; and p is 1, 2, or 3.

In embodiments, a compound of Formula (A), Formula (I), Formula (II) or Formula (III) has the following structure, (IV)

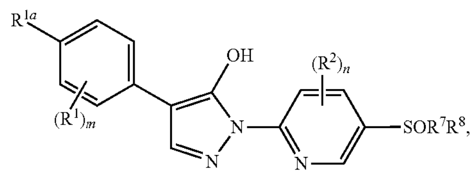

or a pharmaceutically acceptable salt thereof.

In embodiments of Formula (IV), $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^7$ is $C_{1-3}$ alkyl, $C_{3-5}$ cycloalkyl, phenyl, or $NR^{18}R^{19}$; $R^8$ is NH or $NCH_3$; $R^{18}$ is and $R^{19}$ are each independently H or $C_{1-3}$ alkyl; m is 1, 2, 3, or 4; and n is 0, 1, 2 or 3.

In embodiments, $R^1$ is $C_{1-3}$ alkyl. In embodiments, $R^1$ is $CH_3$.

In embodiments, a compound of Formula (A), Formula (I), Formula (II), Formula (III) or Formula (IV) has the following structure, (IVa)

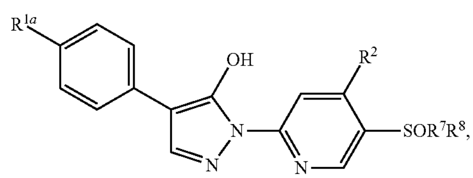

or a pharmaceutically acceptable salt thereof.

In embodiments, $R^{1a}$ is CN or halogen; $R^2$ is selected from the group consisting of hydrogen or $C_{1-3}$ alkyl; $R^7$ is $C_{1-3}$ alkyl, $C_{3-5}$ cycloalkyl, phenyl, or $NR^{18}R^{19}$; $R^8$ is NH or $NCH_3$; and $R^{18}$ and $R^{19}$ are each independently H or $C_{1-3}$ alkyl.

In embodiments, $R^{1a}$ is CN.

In embodiments, $R^{1a}$ is halogen. In embodiments, $R^{1a}$ is Cl.

In embodiments, $R^2$ is $C_{1-3}$ alkyl.

In embodiments, $R^2$ is $CH_3$.

In embodiments, $R^7$ is $C_{1-3}$ alkyl. In embodiments, $R^7$ is $CH_3$. In embodiments, $R^7$ is $CH_2CH_3$. In embodiments, $R^7$ is $CH(CH_3)_2$. In embodiments, $R^7$ is $C_{3-5}$ cycloalkyl. In embodiments, $R^7$ is cyclopropyl. In embodiments, $R^7$ is cyclopentyl. In embodiments, $R^7$ is phenyl. In embodiments, $R^7$ is $NR^{18}R^{19}$, and wherein $R^{18}$ and $R^{19}$ are each independently H or $C_{1-3}$ alkyl.

In embodiments, $R^{18}$ and $R^{19}$ are independently H. In embodiments, $R^{18}$ is H and $R^{19}$ is $C_{1-3}$ alkyl. In embodiments, $R^{19}$ is $CH_3$. In embodiments, $R^{18}$ and $R^{19}$ are independently $CH_3$.

In embodiments, $R^8$ is NH. In embodiments, $R^8$ is $NCH_3$.

In embodiments, a compound of Formula (A), Formula (I), Formula (II) or Formula (III) has the following structure, (V)

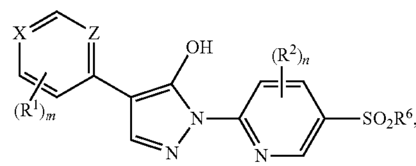

or a pharmaceutically acceptable salt thereof.

In embodiments, X is N or $CR^{1a}$; Z is N or CH; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^6$ is $C_{1-3}$ alkyl, $NHCOR^{15}$, $NR^{16}R^{17}$, or phenyl; $R^{15}$ is $C_{1-3}$ alkyl; $R^{16}$ and $R^{17}$ are each independently H or $C_{1-3}$ alkyl; m is 1, 2, 3, or 4; and n is 0, 1, 2 or 3.

In embodiments, X is N. In embodiments, X is $CR^{1a}$.

In embodiments, $R^{1a}$ is CN. In embodiments, $R^{1a}$ is halogen. In embodiments, $R^{1a}$ is Cl. In embodiments, $R^{1a}$ is F. In embodiments, $R^{1a}$ is Br. In embodiments, $R^{1a}$ is $C_{1-3}$ alkoxy.

In embodiments, $R^{1a}$ is methoxy. In embodiments, $R^{1a}$ is H. In embodiments, $R^{1a}$ is $C_{1-3}$ alkyl optionally substituted with CN. In embodiments, $R^{1a}$ is $CH_2CN$. In embodiments, $R^{1a}$ is OH.

In embodiments, Z is CH. In embodiments, Z is N.

In embodiments, $R^1$ is H. In embodiments, $R^1$ is $C_{1-3}$ alkyl. In embodiments, $R^1$ is $CH_3$. In embodiments, $R^1$ is $C_{1-3}$ alkoxy. In embodiments, $R^1$ is methoxy. In embodiments, $R^1$ is CN.

In embodiments, $R^2$ is H. In embodiments, $R^2$ is $C_{1-3}$ alkyl. In embodiments, $R^2$ is $CH_3$.

In embodiments, $R^6$ is $C_{1-3}$ alkyl. In embodiments, $R^6$ is $CH_3$. In embodiments, $R^6$ is $NHCOR^{15}$, and wherein $R^{15}$ is $C_{1-3}$ alkyl. In embodiments, $R^{15}$ is $CH_3$. In embodiments, $R^6$ is $NR^{16}R^{17}$, and wherein $R^{16}$ and $R^{17}$ are each independently H or $C_{1-3}$ alkyl. In embodiments, $R^6$ is $NH_2$. In embodiments, $R^6$ is phenyl.

In embodiments, a compound of Formula (A), Formula (I), Formula (II) or Formula (III) has the following structure, (VI)

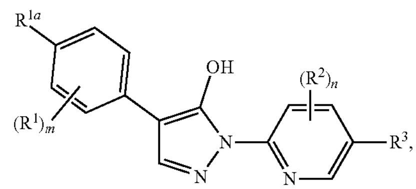

or a pharmaceutically acceptable salt thereof, wherein $R^3$ is cycloalkyl or heterocycloalkyl optionally substituted with $SO_2R^{14}$ or =O.

In embodiments, $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and R are each independently H or $C_{1-3}$ alkyl; $R^{14}$ is $C_{1-3}$ alkyl; m is 1, 2, 3, or 4; and n is 0, 1, 2 or 3.

In embodiments, a compound of Formula (A), Formula (I), Formula (II), Formula (III) or Formula (VI) has the following structure, (VIa)

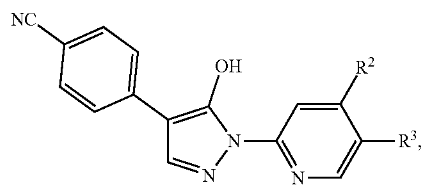

or a pharmaceutically acceptable salt thereof, wherein $R^3$ is cycloalkyl or heterocycloalkyl optionally substituted with $SO_2R^{14}$ or ═O.

In embodiments, $R^2$ is hydrogen or $C_{1-3}$ alkyl; and $R^{14}$ is $C_{1-3}$ alkyl.

In embodiments, $R^2$ is H. In embodiments, $R^2$ is $C_{1-3}$ alkyl. In embodiments, $R^2$ is $CH_3$.

In embodiments, $R^3$ is cycloalkyl.

In embodiments, $R^3$ is cyclopropyl.

In embodiments, $R^3$ is heterocycloalkyl optionally substituted with $SO_2R^{14}$ or ═O, and wherein $R^{14}$ is $C_{1-3}$ alkyl.

In embodiments, $R^3$ is

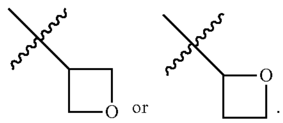 [SMILES: *C1COC1 ; *C1CCO1]

In embodiments, $R^3$ is

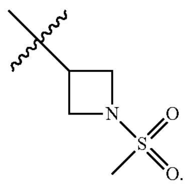 [SMILES: *C1CN(S(C)(=O)=O)C1]

In embodiments, $R^3$ is

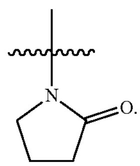 [SMILES: *N1CCCC1=O]

In embodiments, a compound of Formula (A), Formula (I), Formula (II) or Formula (III) has the following structure, (VII)

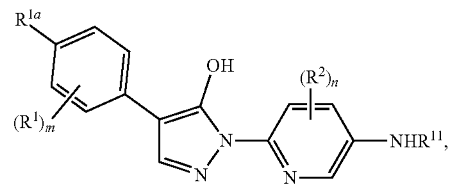

or a pharmaceutically acceptable salt thereof.

In embodiments, $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^{11}$ is $COR^{21}$ or $SO_2R^{22}$; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; $R^{23}$ and $R^{24}$ are independently H or $C_{1-3}$ alkyl; m is 1, 2, 3, or 4; and n is 0, 1, 2 or 3.

In embodiments, a compound of Formula (A), Formula (I), Formula (II), Formula (III) or Formula (VII) has the following structure, (VIIa)

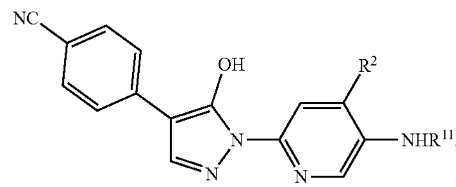

or a pharmaceutically acceptable salt thereof.

In embodiments, $R^2$ is hydrogen or $C_{3-6}$ cycloalkyl; $R^{11}$ is $COR^{21}$ or $SO_2R^{22}$; $R^{21}$ is heterocycloalkyl, cycloalkyl, or $C_{1-3}$ alkyl; and $R^{22}$ is $NR^{23}R^{24}$ or $C_{1-3}$ alkyl optionally substituted with carboxyl, wherein $R^{23}$ and $R^{24}$ are independently H or $C_{1-3}$ alkyl.

In embodiments, $R^2$ is H. In embodiments, $R^2$ is $C_{1-3}$ alkyl. In embodiments, $R^2$ is $CH_3$.

In embodiments, $R^{11}$ is $COR^{21}$, and wherein $R^{21}$ is heterocycloalkyl, cycloalkyl, or $C_{1-3}$ alkyl.

In embodiments, $R^{21}$ is heterocycloalkyl. In embodiments, $R^{21}$ is

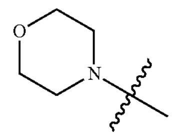

In embodiments, $R^{21}$ is

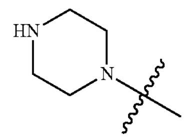

In embodiments, $R^{21}$ is cycloalkyl. In embodiments, $R^{21}$ is cyclopropyl. In embodiments, $R^{21}$ is $C_{1-3}$ alkyl. In embodiments, $R^{21}$ is $CH_2CH_3$.

In embodiments, $R^{11}$ is $SO_2R^{22}$, wherein $R^{22}$ is $NR^{23}R^{24}$ or $C_{1-3}$ alkyl optionally substituted with carboxyl, and wherein $R^{23}$ and $R^{24}$ are independently H or $C_{1-3}$ alkyl.

In embodiments, $R^{22}$ is $C_{1-3}$ alkyl optionally substituted with carboxyl. In embodiments, $R^{22}$ is $CH_3$. In embodiments, $R^{22}$ is $CH_2CH_3$. In embodiments, $R^{22}$ is $CH_2COOH$. In embodiments, $R^{22}$ is $NR^{23}R^{24}$, and wherein $R^{23}$ and $R^{24}$ are independently H or $C_{1-3}$ alkyl. In embodiments, $R^{22}$ is $NHCH_3$. In embodiments, $R^{22}$ is $N(CH_3)_2$.

In embodiments, a compound of Formula (A), Formula (I), Formula (II) or Formula (III) has the following structure, (VIII)

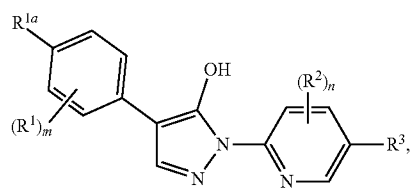

or a pharmaceutically acceptable salt thereof, wherein $R^3$ is heteroaryl optionally substituted with $C_{1-3}$ alkyl or phenyl.

In embodiments, $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; m is 1, 2, 3, or 4; and n is 0, 1, 2 or 3.

In embodiments, a compound of Formula (A), Formula (I), Formula (II), Formula (III) or Formula (VIII) has the following structure, (VIIIa)

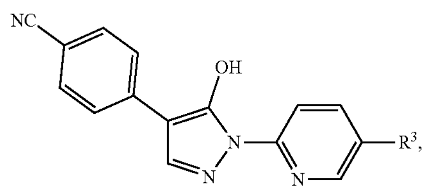

or a pharmaceutically acceptable salt thereof, wherein $R^3$ is heteroaryl optionally substituted with $C_{1-3}$ alkyl or phenyl.

In embodiments, $R^2$ is H.

In embodiments, $R^3$ is heteroaryl. In embodiments, $R^3$ is

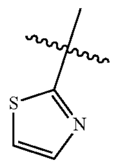

In embodiments, $R^3$ is

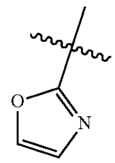

In embodiments, $R^3$ is

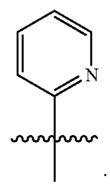

In embodiments, $R^3$ is

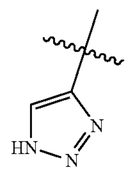

In embodiments, $R^3$ is

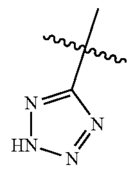

In embodiments, $R^3$ is

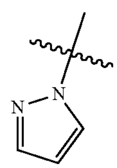

In embodiments, $R^3$ is heteroaryl optionally substituted with $C_{1-3}$ alkyl or phenyl. In embodiments, $R^3$ is

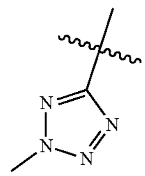

In embodiments, $R^3$ is

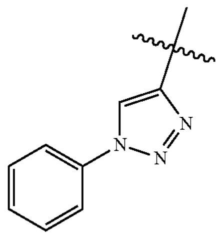

In embodiments, $R^3$ is

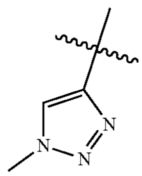

In embodiments, a compound of Formula (A), Formula (I), Formula (II) or Formula (III) has the following structure, (IX)

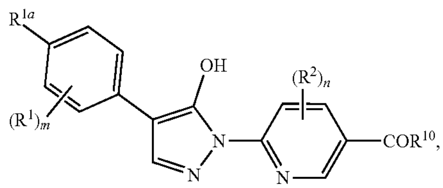

or a pharmaceutically acceptable salt thereof.

In embodiments, $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^{10}$ is $C_{1-3}$ alkyl or $NHSO_2R^{20}$; $R^{20}$ is $C_{1-3}$ alkyl; m is 1, 2, 3, or 4; and n is 0, 1, 2 or 3.

In embodiments, a compound of Formula (A), Formula (I), Formula (II), Formula (III) or Formula (IX) has the following structure, (IXa)

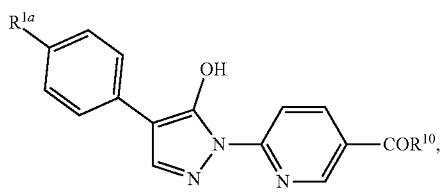

or a pharmaceutically acceptable salt thereof.

In embodiments, $R^{1a}$ is CN or halogen; $R^{10}$ is $C_{1-3}$ alkyl or $NHSO_2R^{20}$; and $R^{20}$ is $C_{1-3}$ alkyl.

In embodiments, $R^{1a}$ is CN. In embodiments, $R^{1a}$ is halogen. In embodiments, $R^{1a}$ is Cl.

In embodiments, $R^{10}$ is $C_{1-3}$ alkyl. In embodiments, $R^{10}$ is $CH_3$. In embodiments, $R^{10}$ is $CH(CH_3)_2$. In embodiments, $R^{10}$ is $CH_2CH_3$. In embodiments, $R^{10}$ is $NHSO_2R^{20}$, and wherein $R^{20}$ is $C_{1-3}$ alkyl. In embodiments, $R^{20}$ is $CH_3$.

In embodiments, a compound of Formula (A), Formula (I), Formula (II) or Formula (III) has the following structure, (X)

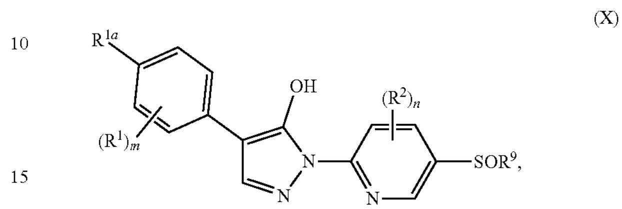

or a pharmaceutically acceptable salt thereof.

In embodiments, $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^9$ is $C_{1-3}$ alkyl; m is 1, 2, 3, or 4; and n is 0, 1, 2 or 3.

In embodiments, $R^{1a}$ is CN.

In embodiments, $R^1$ is H.

In embodiments, $R^2$ is H.

In embodiments, $R^9$ is $C_{1-3}$ alkyl. In embodiments, $R^9$ is $CH_3$.

In embodiments, a compound of Formula (A), Formula (I), Formula (II), or Formula (III) has the following structure, (XI)

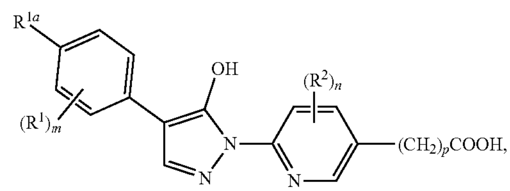

or a pharmaceutically acceptable salt thereof.

In embodiments, $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; m is 1, 2, 3, or 4; n is 0, 1, 2 or 3; and p is 1, 2, or 3.

In embodiments, $R^{1a}$ is CN.

In embodiments, $R^1$ is H.

In embodiments, $R^2$ is H.

In embodiments, p is 1.

In embodiments, a compound of Formula (A), Formula (I), Formula (II) or Formula (III) has the following structure, (XII)

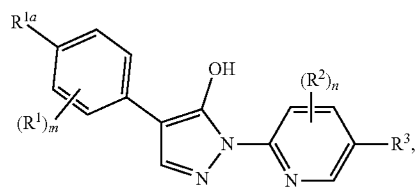

or a pharmaceutically acceptable salt thereof, wherein $R^3$ is halogen.

In embodiments, $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; m is 1, 2, 3, or 4; and n is 0, 1, 2 or 3.

In embodiments, $R^{1a}$ is CN.

In embodiments, $R^1$ is H.

In embodiments, $R^2$ is H.

In embodiments, $R^3$ is Cl. In embodiments, $R^3$ is Br. In embodiments, $R^3$ is F.

In embodiments, a compound of Formula (A), Formula (I), Formula (II) or Formula (III) has the following structure, (XIII)

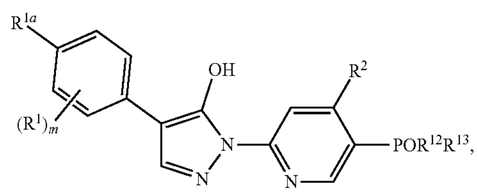

or a pharmaceutically acceptable salt thereof.

In embodiments, $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; and $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^{12}$ is $C_{1-3}$ alkyl; $R^{13}$ is $C_{1-3}$ alkyl; and m is 1, 2, 3, or 4.

In embodiments, $R^{1a}$ is CN.

In embodiments, $R^1$ is H.

In embodiments, $R^2$ is $C_{1-3}$ alkyl. In embodiments, $R^2$ is $CH_3$.

In embodiments, $R^{12}$ is $C_{1-3}$ alkyl. In embodiments, $R^{12}$ is $CH_3$.

In embodiments, $R^{13}$ is $C_{1-3}$ alkyl. In embodiments, $R^{13}$ is $CH_3$.

In some embodiments, the compound is any one of Compounds 1-33:

| Cmpd No. | Structure |
| --- | --- |
| 1 | 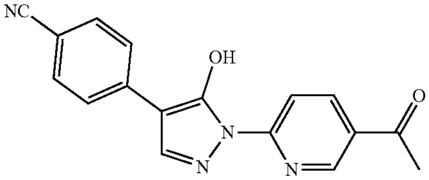 [SMILES: CC(=O)c1ccc(-n2ncc(-c3ccc(C#N)cc3)c2O)nc1] |
| 2 | 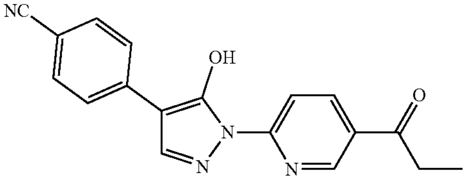 [SMILES: CCC(=O)c1ccc(-n2ncc(-c3ccc(C#N)cc3)c2O)nc1] |
| 3 | 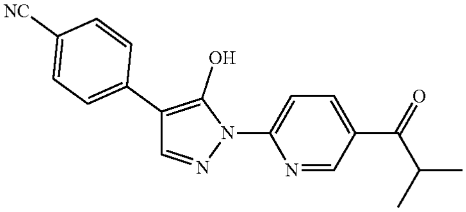 [SMILES: CC(C)C(=O)c1ccc(-n2ncc(-c3ccc(C#N)cc3)c2O)nc1] |
| 4 | 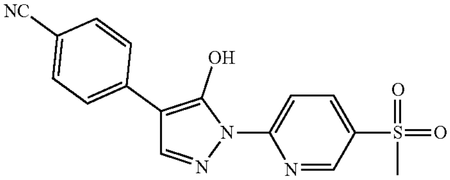 [SMILES: CS(=O)(=O)c1ccc(-n2ncc(-c3ccc(C#N)cc3)c2O)nc1] |
| 5 | 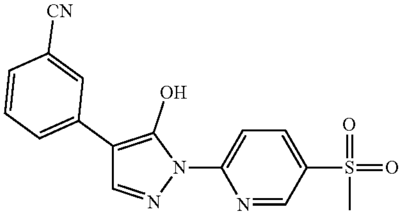 [SMILES: CS(=O)(=O)c1ccc(-n2ncc(-c3cccc(C#N)c3)c2O)nc1] |
| 6 | 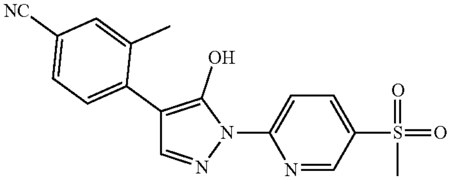 [SMILES: Cc1cc(C#N)ccc1-c1cnn(-c2ccc(S(C)(=O)=O)cn2)c1O] |
| 7 | 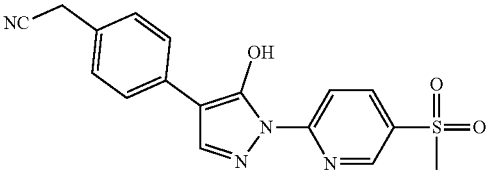 [SMILES: CS(=O)(=O)c1ccc(-n2ncc(-c3ccc(CC#N)cc3)c2O)nc1] |

-continued
| Cmpd No. | Structure |
|---|---|
| 8 | 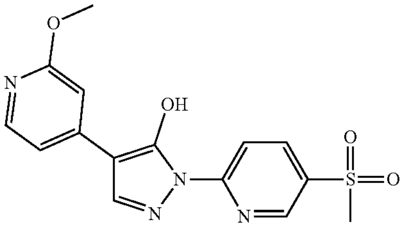 [SMILES: COc1cc(-c2cnn(-c3ccc(S(C)(=O)=O)cn3)c2O)ccn1] |
| 9 | 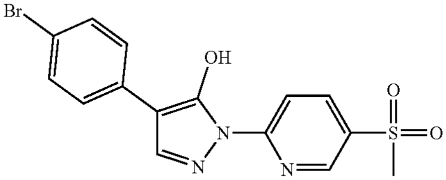 |
| 10 | 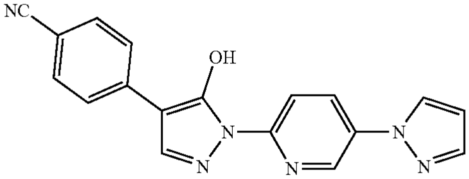 [SMILES: N#Cc1ccc(-c2cnn(-c3ccc(-n4cccn4)cn3)c2O)cc1] |
| 11 | 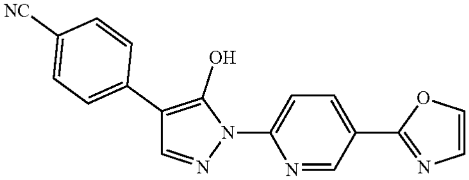 |
| 12 | 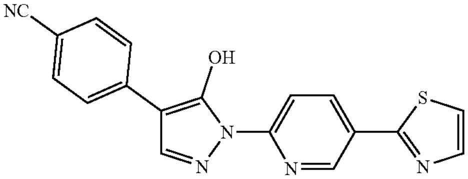 [SMILES: N#Cc1ccc(-c2cnn(-c3ccc(-c4nccs4)cn3)c2O)cc1] |
| 13 | 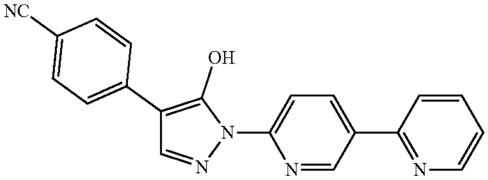 [SMILES: N#Cc1ccc(-c2cnn(-c3ccc(-c4ccccn4)cn3)c2O)cc1] |
| 14 | 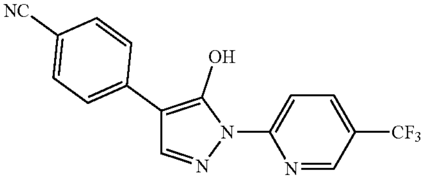 [SMILES: N#Cc1ccc(-c2cnn(-c3ccc(C(F)(F)F)cn3)c2O)cc1] |
-continued
| Cmpd No. | Structure |
|---|---|
| 15 | 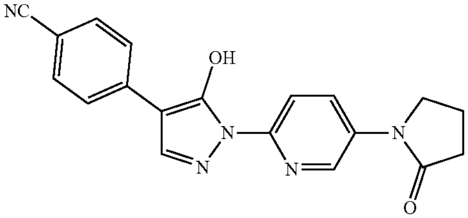 [SMILES: N#Cc1ccc(-c2cnn(-c3ccc(N4CCCC4=O)cn3)c2O)cc1] |
| 16 | 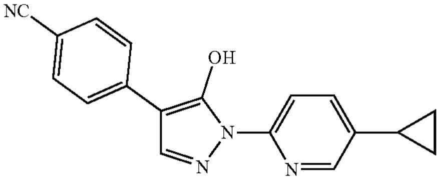 [SMILES: N#Cc1ccc(-c2cnn(-c3ccc(C4CC4)cn3)c2O)cc1] |
| 17 | 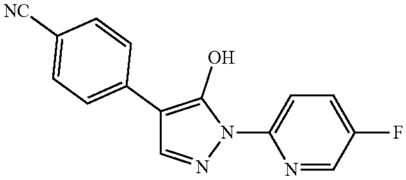 [SMILES: N#Cc1ccc(-c2cnn(-c3ccc(F)cn3)c2O)cc1] |
| 18 | 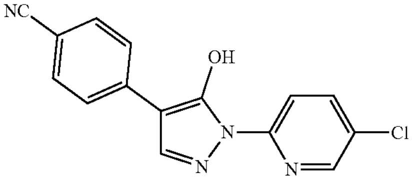 |
| 19 | 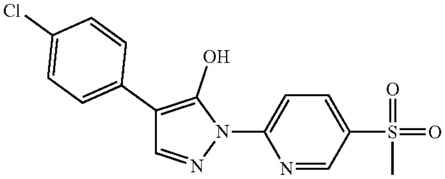 [SMILES: CS(=O)(=O)c1ccc(-n2ncc(-c3ccc(Cl)cc3)c2O)nc1] |
| 20 | 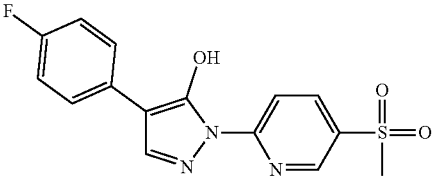 [SMILES: CS(=O)(=O)c1ccc(-n2ncc(-c3ccc(F)cc3)c2O)nc1] |
| 21 | 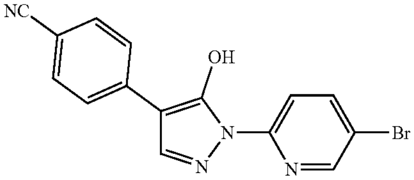 [SMILES: N#Cc1ccc(-c2cnn(-c3ccc(Br)cn3)c2O)cc1] |

-continued

| Cmpd No. | Structure |
|---|---|
| 22 | 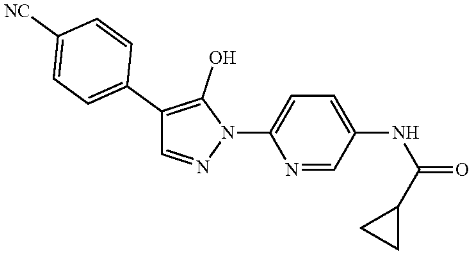 [SMILES: N#Cc1ccc(-c2cnn(-c3ccc(NC(=O)C4CC4)cn3)c2O)cc1] |
| 23 | 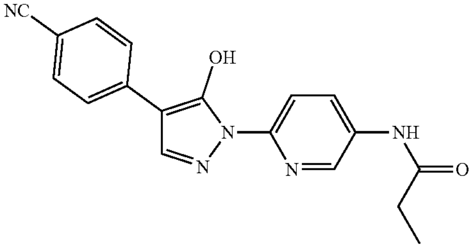 [SMILES: CCC(=O)Nc1ccc(-n2ncc(-c3ccc(C#N)cc3)c2O)nc1] |
| 24 | 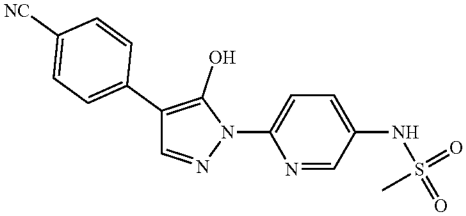 [SMILES: CS(=O)(=O)Nc1ccc(-n2ncc(-c3ccc(C#N)cc3)c2O)nc1] |
| 25 | 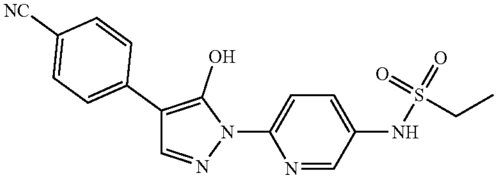 [SMILES: CCS(=O)(=O)Nc1ccc(-n2ncc(-c3ccc(C#N)cc3)c2O)nc1] |
| 26 | 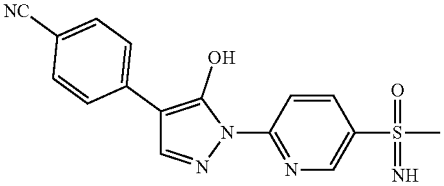 [SMILES: CS(=N)(=O)c1ccc(-n2ncc(-c3ccc(C#N)cc3)c2O)nc1] |
| 27 | 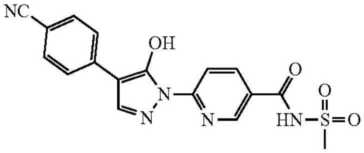 [SMILES: CS(=O)(=O)NC(=O)c1ccc(-n2ncc(-c3ccc(C#N)cc3)c2O)nc1] |
| 28 | 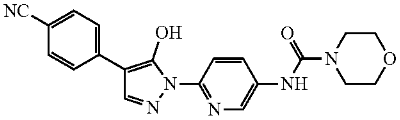 [SMILES: N#Cc1ccc(-c2cnn(-c3ccc(NC(=O)N4CCOCC4)cn3)c2O)cc1] |

-continued

| Cmpd No. | Structure |
|---|---|
| 29 | 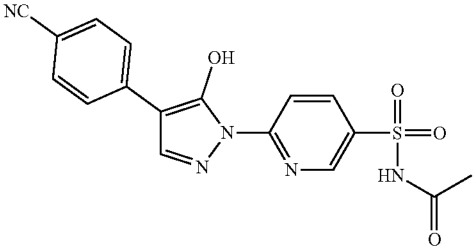 [SMILES: CC(=O)NS(=O)(=O)c1ccc(-n2ncc(-c3ccc(C#N)cc3)c2O)nc1] |
| 30 | 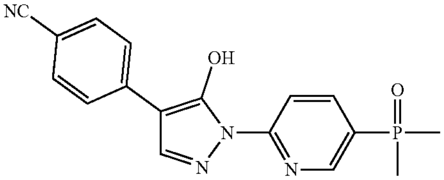 [SMILES: CP(C)(=O)c1ccc(-n2ncc(-c3ccc(C#N)cc3)c2O)nc1] |
| 31 | 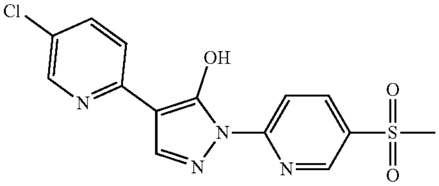 [SMILES: CS(=O)(=O)c1ccc(-n2ncc(-c3ccc(Cl)cn3)c2O)nc1] |
| 32 | 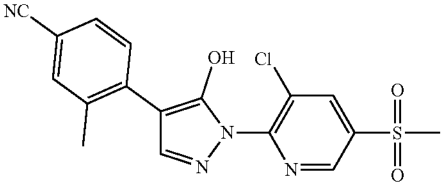 [SMILES: Cc1cc(C#N)ccc1-c1cnn(-c2ncc(S(C)(=O)=O)cc2Cl)c1O] |
| 33 | 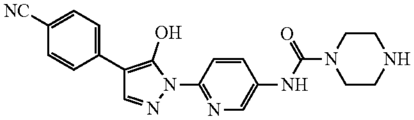 [SMILES: N#Cc1ccc(-c2cnn(-c3ccc(NC(=O)N4CCNCC4)cn3)c2O)cc1] |

In embodiments, a compound of Formulas (A) and (I)-(XIII) such as any one of Compounds 1-33, at least one hydrogen atom is replaced with a deuterium atom.

In another aspect, the invention features a pharmaceutical composition comprising any compound described herein (e.g., a compound of Formulas (A) and (I)-(XIII) such as any one of Compounds 1-33), or a pharmaceutically acceptable salt thereof, and a pharmaceutically acceptable excipient.

In another aspect, the invention features a method for treating a disease mediated by PHD activity comprising administering to a subject any compound described herein (e.g., a compound of Formulas (A) and (I)-(XIII) such as any one of Compounds 1-33), or a pharmaceutically acceptable salt thereof.

In embodiments, a disease mediated by PHD activity is an ischemic reperfusion injury. (e.g., stroke, myocardial infarction, or acute kidney injury).

In embodiments, a disease mediated by PHD activity is inflammatory bowel disease (e.g., ulcerative colitis or Crohn's disease).

In embodiments, a disease mediated by PHD activity is cancer (e.g., colorectal cancer).

In embodiments, a disease mediated by PHD activity is liver disease.

In embodiments, a disease mediated by PHD activity is atherosclerosis.

In embodiments, a disease mediated by PHD activity is cardiovascular disease

In embodiments, a disease mediated by PHD activity is a disease or condition of the eye (e.g., radiation retinopathy, retinopathy of prematurity, diabetic retinopathy, age-related macular degeneration, and ocular ischemia).

In embodiments, a disease mediated by PHD activity is anemia (e.g., anemia associated with chronic kidney disease).

In embodiments, a disease mediated by PHD activity is associated with hyperoxia

In embodiments, a disease mediated by PHD activity is retinopathy of prematurity.

In embodiments, a disease mediated by PHD activity is bronchopulmonary dysplasia (BPD).

In embodiments, a disease mediated by PHD activity is ischemic heart disease, valvular heart disease, congestive heart failure, acute lung injury, pulmonary fibrosis, pulmonary hypertension, chronic obstructive pulmonary disease (COPD), acute liver failure, liver fibrosis, or cirrhosis.

BRIEF DESCRIPTION OF DRAWINGS

FIG. 1 is an exemplary schematic illustration demonstrating the principle of the TR-FRET Assay for PHD enzymes (PHD1, PHD2, and PHD3). In the presence of 2-oxoglutarate and $O_2$, PHD enzyme hydroxylates proline 564 of biotin-tagged HIF-1$\alpha$ peptide resulting in generation of biotin-tagged HIF-1$\alpha$-hydroxyproline, succinate and $CO_2$. The resulting proximity of the donor fluorophore complex, monoclonal antibody anti-6His-Terbium (Tb)-cryptate Gold, bound to the His-tagged VHL protein, EloB, EloC complex (His-VBC) and the acceptor fluorophore, SA-D2 complex, bound to HIF-1$\alpha$-hydroxyproline results in a fluorescence resonance energy transfer signal that can be detected and quantified

DETAILED DESCRIPTION OF THE DISCLOSURE

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, a bovine, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used in the description and the appended claims, the singular forms "a," "an," and "the" include plural referents unless the context clearly dictates otherwise. Thus, for example, reference to "a composition" includes mixtures of two or more such compositions.

Throughout the description and claims of this specification the word "comprise" and other forms of the word, such as "comprising" and "comprises," means including but not limited to, and is not intended to exclude, for example, other additives, components, integers, or steps.

"Optional" or "optionally" means that the subsequently described event or circumstance may or may not occur, and that the description includes instances where the event or circumstance occurs and instances where it does not.

Improve, increase, or reduce: As used herein, the terms "improve," "increase," or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable," as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid, or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4 alkyl)4 salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate, and aryl sulfonate. Further pharmaceutically acceptable salts include salts formed from the quaternization of an amine using an appropriate electrophile, e.g., an alkyl halide, to form a quarternized alkylated amino salt.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Aliphatic: As used herein, the term aliphatic refers to $C_1$-$C_{40}$ hydrocarbons and includes both saturated and unsaturated hydrocarbons. An aliphatic may be linear, branched, or cyclic. For example, $C_1$-$C_{20}$ aliphatics can include $C_1$-$C_{20}$ alkyls (e.g., linear or branched $C_1$-$C_{20}$ saturated alkyls), $C_2$-$C_{20}$ alkenyls (e.g., linear or branched $C_4$-$C_{20}$ dienyls, linear, or branched $C_6$-$C_{20}$ trienyls, and the like), and $C_2$-$C_{20}$ alkynyls (e.g., linear or branched $C_2$-$C_{20}$ alkynyls). $C_1$-$C_{20}$ aliphatics can include $C_3$-$C_{20}$ cyclic aliphatics (e.g., $C_3$-$C_{20}$ cycloalkyls, $C_4$-$C_{20}$ cycloalkenyls, or C5-C20 cycloalkynyls). In certain embodiments, the aliphatic may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. An aliphatic group is unsubstituted or substituted with one or more substituent groups as described herein. For example, an aliphatic may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —$N(R')_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In some embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In some embodiments, R' independently is unsubstituted $C_1$-$C_3$ alkyl. In some embodiments, the aliphatic is unsubstituted. In some embodiments, the aliphatic does not include any heteroatoms.

Alkyl: As used herein, the term "alkyl" means acyclic linear and branched hydrocarbon groups, e.g. "$C_1$-$C_{20}$ alkyl" refers to alkyl groups having 1-20 carbons. An alkyl group may be linear or branched. Examples of alkyl groups include, but are not limited to, methyl, ethyl, n-propyl, isopropyl, butyl, isobutyl, sec-butyl, tert-butyl, pentyl, isopentyl tert-pentylhexyl, isohexyl, etc. The term "lower alkyl" means an alkyl group straight chain or branched alkyl having 1 to 6 carbon atoms. Other alkyl groups will be readily apparent to those of skill in the art given the benefit of the present disclosure. An alkyl group may be unsubstituted or substituted with one or more substituent groups as described herein. For example, an alkyl group may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —$N(R')_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In some embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In some embodiments, R' independently is unsubstituted $C_1$-$C_3$ alkyl. In some embodiments, the alkyl is substituted (e.g., with 1, 2, 3, 4, 5, or 6 substituent groups as described herein). In some embodiments, an alkyl group is substituted with a —OH group and may also be referred to herein as a "hydroxyalkyl" group, where the prefix denotes the —OH group and "alkyl" is as described herein. In some embodiments, the alkyl is substituted with a —OR' group and may also be referred to herein as "alkoxy" group.

Affixing the suffix "-ene" to a group indicates the group is a divalent moiety, e.g., arylene is the divalent moiety of aryl, and heteroarylene is the divalent moiety of heteroaryl.

Alkylene: The term “alkylene,” as used herein, represents a saturated divalent straight or branched chain hydrocarbon group and is exemplified by methylene, ethylene, isopropylene and the like. Likewise, the term “alkenylene” as used herein represents an unsaturated divalent straight or branched chain hydrocarbon group having one or more unsaturated carbon-carbon double bonds that may occur in any stable point along the chain, and the term “alkynylene” herein represents an unsaturated divalent straight or branched chain hydrocarbon group having one or more unsaturated carbon-carbon triple bonds that may occur in any stable point along the chain. In certain embodiments, an alkylene, alkenylene, or alkynylene group may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. For example, an alkylene, alkenylene, or alkynylene may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —$N(R')_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In some embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In some embodiments, R' independently is unsubstituted $C_1$-$C_3$ alkyl. In certain embodiments, an alkylene, alkenylene, or alkynylene is unsubstituted. In certain embodiments, an alkylene, alkenylene, or alkynylene does not include any heteroatoms.

Alkenyl: As used herein, “alkenyl” means any linear or branched hydrocarbon chains having one or more unsaturated carbon-carbon double bonds that may occur in any stable point along the chain, e.g. “$C_2$-$C_{20}$ alkenyl” refers to an alkenyl group having 2-20 carbons. For example, an alkenyl group includes prop-2-enyl, but-2-enyl, but-3-enyl, 2-methylprop-2-enyl, hex-2-enyl, hex-5-enyl, 2,3-dimethylbut-2-enyl, and the like. In some embodiments, the alkenyl comprises 1, 2, or 3 carbon-carbon double bond. In some embodiments, the alkenyl comprises a single carbon-carbon double bond. In some embodiments, multiple double bonds (e.g., 2 or 3) are conjugated. An alkenyl group may be unsubstituted or substituted with one or more substituent groups as described herein. For example, an alkenyl group may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —$N(R')_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In some embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In some embodiments, R' independently is unsubstituted $C_1$-$C_3$ alkyl. In some embodiments, the alkenyl is unsubstituted. In some embodiments, the alkenyl is substituted (e.g., with 1, 2, 3, 4, 5, or 6 substituent groups as described herein). In some embodiments, an alkenyl group is substituted with a —OH group and may also be referred to herein as a “hydroxyalkenyl” group, where the prefix denotes the —OH group and “alkenyl” is as described herein.

Alkynyl: As used herein, “alkynyl” means any hydrocarbon chain of either linear or branched configuration, having one or more carbon-carbon triple bonds occurring in any stable point along the chain, e.g. “$C_2$-$C_{20}$ alkynyl” refers to an alkynyl group having 2-20 carbons. Examples of an alkynyl group include prop-2-ynyl, but-2-ynyl, but-3-ynyl, pent-2-ynyl, 3-methylpent-4-ynyl, hex-2-ynyl, hex-5-ynyl, etc. In some embodiments, an alkynyl comprises one carbon-carbon triple bond. An alkynyl group may be unsubstituted or substituted with one or more substituent groups as described herein. For example, an alkynyl group may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —$N(R')_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In some embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In some embodiments, R' independently is unsubstituted $C_1$-$C_3$ alkyl. In some embodiments, the alkynyl is unsubstituted. In some embodiments, the alkynyl is substituted (e.g., with 1, 2, 3, 4, 5, or 6 substituent groups as described herein).

Aryl: The term “aryl” used alone or as part of a larger moiety as in “aralkyl,” refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 4 to 7 ring members. In some embodiments, an aryl group has 6 ring carbon atoms (“C6 aryl,” e.g., phenyl). In some embodiments, an aryl group has 10 ring carbon atoms (“$C_{10}$ aryl,” e.g., naphthyl such as 1-naphthyl and 2-naphthyl). In some embodiments, an aryl group has 14 ring carbon atoms (“C14 aryl,” e.g., anthracyl). “Aryl” also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Exemplary aryls include phenyl, naphthyl, and anthracene.

Arylene: The term “arylene” as used herein refers to an aryl group that is divalent (that is, having two points of attachment to the molecule). Exemplary arylenes include phenylene (e.g., unsubstituted phenylene or substituted phenylene).

Halogen or Halo: As used herein, the term “halogen” or “halo” means fluorine, chlorine, bromine, or iodine.

Amide: The term “amide” or “amido” refers to a chemical moiety with formula —$C(O)N(R')_2$, —C(O)N(R')—, —NR'C(O)R', —NR'C(O)$N(R')_2$—, or —NR'C(O)—, where each R' is independently selected from hydrogen, alkyl, alkenyl, alkynyl, heteroalkyl (bonded through a chain carbon), cycloalkyl, aryl, arylalkyl, heteroaryl (bonded through a ring carbon), heteroarylalkyl, or heterocycloalkyl (bonded through a ring carbon), unless stated other-wise in the specification, each of which moiety can itself be optionally substituted as described herein, or two R' can combine with the nitrogen atom to form a 3-, 4-, 5-, 6-, or 7-membered ring.

Amino: The term “amino” or “amine” refers to a —$N(R')_2$ group, where each R' is independently selected from hydrogen, alkyl, alkenyl, alkynyl, heteroalkyl (bonded through a chain carbon), cycloalkyl, aryl, arylalkyl, heteroaryl (bonded through a ring carbon), heteroarylalkyl, heterocycloalkyl (bonded through a ring carbon), sulfonyl, amide or carbonyl group, unless stated other-wise in the specification, each of which moiety can itself be optionally substituted as described herein, or two R' can combine with the nitrogen atom to form a 3-, 4-, 5-, 6-, or 7-membered ring. In embodiments, an amino group is —NHR', where R' is aryl ("arylamino"), heteroaryl ("heteroarylamino"), amide or alkyl ("alkylamino").

Sulfonyl: The term "sulfonyl" refers to a —S(=O)$_2$R', or —S(=O)$_2$— group, where R' is selected from hydrogen, alkyl, alkenyl, alkynyl, heteroalkyl (bonded through a chain carbon), amino, cycloalkyl, aryl, arylalkyl, heteroaryl (bonded through a ring carbon), heteroarylalkyl, heterocycloalkyl (bonded through a ring carbon), unless stated otherwise in the specification, each of which moiety can itself be optionally substituted as described herein. For example, in one embodiment, the sulfonyl group is —SO$_2$R', where R' is alkyl substituted with a carbonyl group.

Sulfinyl: The term "sulfinyl" refers to a chemical moiety with formula —S(=O)R', —S(=O)—, or —S(=O)(=NR')—, where R' is selected from hydrogen, alkyl, alkenyl, alkynyl, heteroalkyl (bonded through a chain carbon), cycloalkyl, aryl, arylalkyl, heteroaryl (bonded through a ring carbon), heteroarylalkyl, heterocycloalkyl (bonded through a ring carbon), unless stated other-wise in the specification, each of which moiety can itself be optionally substituted as described herein.

Carbonyl: The term "carbonyl" refers to a —C(=O)R', or —C(=O)— group, where R' is selected from hydrogen, alkyl, alkenyl, alkynyl, heteroalkyl (bonded through a chain carbon), cycloalkyl, aryl, arylalkyl, amino, hydroxyl, heteroaryl (bonded through a ring carbon), heteroarylalkyl, heterocycloalkyl (bonded through a ring carbon), unless stated other-wise in the specification, each of which moiety can itself be optionally substituted as described herein.

Phosphoryl: The term "phosphoryl" refers to a —P(=O)(R')$_2$, or —P(=O)(R')— group, where R' is selected from hydrogen, alkyl, alkenyl, alkynyl, heteroalkyl (bonded through a chain carbon or through the heteroatom), cycloalkyl, aryl, arylalkyl, heteroaryl (bonded through a ring carbon), heteroarylalkyl, or heterocycloalkyl (bonded through a ring carbon) group, unless stated other-wise in the specification, each of which moiety can itself be optionally substituted as described herein, or two R' can combine with the nitrogen atom to form a 3-, 4-, 5-, 6-, or 7-membered ring.

Heteroalkyl: The term "heteroalkyl" is meant a branched or unbranched alkyl, alkenyl, or alkynyl group having from 1 to 14 carbon atoms in addition to 1, 2, 3 or 4 heteroatoms independently selected from the group consisting of N, O, S, and P. Heteroalkyls include tertiary amines, secondary amines, ethers, thioethers, amides, thioamides, carbamates, thiocarbamates, hydrazones, imines, phosphodiesters, phosphoramidates, sulfonamides, and disulfides. A heteroalkyl group may optionally include monocyclic, bicyclic, or tricyclic rings, in which each ring desirably has three to six members. Examples of heteroalkyls include polyethers, such as methoxymethyl and ethoxyethyl.

Heteroalkylene: The term "heteroalkylene," as used herein, represents a divalent form of a heteroalkyl group as described herein.

Heteroaryl: The term "heteroaryl," as used herein, refers to a monocyclic, bicyclic, or tricyclic carbocyclic ring system having a total of six to fourteen ring members, wherein said ring system has a single point of attachment to the rest of the molecule, wherein at least one ring in the system is aromatic, wherein each ring in the system contains 4 to 7 ring members, and wherein at least one ring atom is a heteroatom such as, but not limited to, nitrogen and oxygen.

Heterocycloalkyl: The term "heterocycloalkyl," as used herein, is a non-aromatic ring wherein at least one atom is a heteroatom such as, but not limited to, nitrogen, oxygen, sulfur, or phosphorus, and the remaining atoms are carbon. The heterocycloalkyl group can be substituted or unsubstituted.

Deuterium: The term "deuterium" ("D" or "$^2$H") is also called heavy hydrogen. Deuterium is isotope of hydrogen with a nucleus consisting of one proton and one neutron, which is double the mass of the nucleus of ordinary hydrogen (one proton).

Isotope: The term "isotope" refers to a variant of a particular chemical element which differs in neutron number, and consequently in nucleon number. All isotopes of a given element have the same number of protons but different numbers of neutrons in each atom.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system, e.g., the substitution results in a stable compound (e.g., a compound which does not spontaneously undergo transformation such as by rearrangement, cyclization, elimination, or other reaction). In cases where a specified moiety or group is not expressly noted as being optionally substituted or substituted with any specified substituent, it is understood that such a moiety or group is intended to be unsubstituted.

When a ring system (e.g., cycloalkyl, heterocyclyl, aryl, or heteroaryl) is substituted with a number of substituents varying within an expressly defined range, it is understood that the total number of substituents does not exceed the normal available valencies under the existing conditions. It is also understood that hydrogen atoms are presumed present to fill the remaining valence of a ring system. The substituted group encompasses only those combinations of substituents and variables that result in a stable or chemically feasible compound. A stable compound or chemically feasible compound is one that, among other factors, has stability sufficient to permit its preparation and detection.

A wide variety of substituents are well known, and methods for their formation and introduction into a variety of parent groups are also well known. Representative substituents include but are not limited to alkyl, cycloalkyl, alkenyl, cycloalkenyl, alkynyl, arylalkyl, alkylaryl, aryl, arylalkoxy, arylamino, heteroarylamino, heteroaryl, heteroarylalkoxy, heterocycloalkyl, hydroxyalkyl, aminoalkyl, haloalkyl, thioalkyl, alkylthioalkyl, carboxyalkyl, imidazolylalkyl, indolylalkyl, mono-, di- and trihaloalkyl, mono-, di- and trihaloalkoxy, amino, alkylamino, dialkylamino, amide, cyano, alkoxy, hydroxy, sulfonamide, halo (e.g., —Cl and —Br), nitro, oximino, —COOR$^{50}$, —COR$^{50}$, —S$_{0-2}$R$^{50}$, —SO$_2$NR$^{50}$R$^{51}$, NR$^{52}$SO$_2$R$^{50}$, =C(R$^{50}$R$^{51}$), =N—OR$^{50}$, =N—CN, =C(halo)$_2$, =S, =O, —CON(R$^{50}$R$^{51}$), —OCOR$^{50}$, —OCON(R$^{50}$R$^{51}$), —N(R$^{52}$)CO(R$^{50}$), —N(R$^{52}$)COOR$^{50}$ and —N(R$^{52}$)CON(R$^{50}$(R$^{51}$), wherein R$^{50}$, R$^{51}$ and R$^{52}$ may be independently selected from the following: a hydrogen atom and a branched or straight-chain, C$_{1-6}$-alkyl, C$_{3-6}$-cycloalkyl, C$_{4-6}$-heterocycloalkyl, heteroaryl and aryl group, with or without substituents. When permissible, R$^{50}$ and R$^{51}$ can be joined together to form a carbocyclic or heterocyclic ring system.

In preferred embodiments, the substituent is selected from halogen, —COR', —CO$_2$H, —CO$_2$R', —CN, —OH, —OR', —OCOR', —OCO$_2$R', —NH$_2$, —NHR', —N(R')$_2$, —SR', and -SO$_2$R', wherein each instance of R' independently is C$_1$-C$_{20}$ aliphatic (e.g., C$_1$-C$_{20}$ alkyl, C$_1$-C$_{15}$ alkyl, C$_1$-C$_{10}$ alkyl, or $C_1$-$C_3$ alkyl). In certain embodiments thereof, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). Preferably, R' independently is unsubstituted $C_1$-$C_3$ alkyl.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Compound of the Invention

Disclosed herein are compounds that are potent inhibitors of PHD. In some embodiments, the compounds of the present invention have enzymatic half maximal inhibitory concentration ($IC_{50}$) values of less than 100 μM against any one of PHD1, PHD2, and PHD3. In some embodiments, the compounds of the present invention have an $IC_{50}$ value of less than 50 μM against any one of PHD1, PHD2, and PHD3. In some embodiments, the compounds of the present invention have an $IC_{50}$ value of less than 25 μM against any one of PHD1, PHD2, and PHD3. In some embodiments, the compounds of the present invention have an $IC_{50}$ value of less than 20 μM against any one of PHD1, PHD2, and PHD3. In some embodiments, the compounds of the present invention have an $IC_{50}$ value of less than 15 μM against any one of PHD1, PHD2, and PHD3. In some embodiments, the compounds of the present invention have an $IC_{50}$ value of less than 10 μM against any one of PHD1, PHD2, and PHD3. In some embodiments, the compounds of the present invention have an $IC_{50}$ value of less than 5 μM against any one of PHD1, PHD2, and PHD3. In some embodiments, the compounds of the present invention have an $IC_{50}$ value of less than 1 μM against any one of PHD1, PHD2, and PHD3. In some embodiments, the compounds of the present invention have an $IC_{50}$ value of about 3 nM to about 5 nM against any one of PHD1, PHD2, and PHD3. In some embodiments, the compounds of the present invention have an $IC_{50}$ value of about 5 nM to about 10 nM against any one of PHD1, PHD2, and PHD3. In some embodiments, the compounds of the present invention have an $IC_{50}$ value of about 10 nM to about 20 nM against any one of PHD1, PHD2, and PHD3. In some embodiments, the compounds of the present invention have an $IC_{50}$ value of about 20 nM to about 50 nM against any one of PHD1, PHD2, and PHD3. In some embodiments, the compounds of the present invention have an $IC_{50}$ value of about 50 nM to about 100 nM against any one of PHD1, PHD2, and PHD3. In some embodiments, the compounds of the present invention have an $IC_{50}$ value of about 100 nM to about 200 nM against any one of PHD1, PHD2, and PHD3. In some embodiments, the compounds of the present invention have an $IC_{50}$ value of about 200 nM to about 500 nM against any one of PHD1, PHD2, and PHD3. In some embodiments, the compounds of the present invention have an $IC_{50}$ value of about 500 nM to about 1000 nM against any one of PHD1, PHD2, and PHD3.

Representative examples from this class show inhibitory activity for PHD1, PHD2 and PHD3 in vitro.

Exemplary compounds are described herein. In particular, these selective inhibitors can feature a pyrazole moiety (e.g., a 5-hydroxy substituted pyrazole) linking the two aromatic moieties.

Compounds of Formulas (A) and (I)-(XIII)

In an aspect, provided herein are compounds having a structure according to Formula (A):

(A)

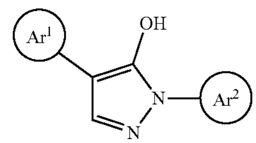

or a pharmaceutically acceptable salt thereof, wherein:

$Ar^1$ is aryl or heteroaryl, optionally substituted with one or more groups selected from halogen, CN, OH, $C_{1-3}$ alkyl optionally substituted with CN or one or more halogens, and $C_{1-3}$ alkoxy; and $Ar^2$ is pyrid-2-yl, optionally substituted with one or more groups selected from halogen; amino; amide; OH; a sulfonyl group; a sulfinyl group; a carbonyl group; a phosphoryl group; $C_{3-6}$ cycloalkyl; $C_{3-6}$ heterocycloalkyl optionally substituted with a sulfonyl group or =O; $C_{1-3}$ alkyl optionally substituted with carbonyl or one or more halogens; and heteroaryl optionally substituted with $C_{1-3}$ alkyl or phenyl.

In embodiments, $Ar^1$ is an unsubstituted aryl. In embodiments, $Ar^1$ is a substituted aryl. In embodiments, $Ar^1$ is a substituted phenyl.

In embodiments, $Ar^1$ is an unsubstituted 6-membered heteroaryl. In embodiments, $Ar^1$ is a substituted 6-membered heteroaryl.

In embodiments, $Ar^1$ is substituted with one or more groups selected from halogen, CN, OH, $C_{1-3}$ alkyl optionally substituted with CN or one or more halogens, and $C_{1-3}$ alkoxy. In some embodiments, $Ar^1$ is substituted with 1 substituent group. In some embodiments, $Ar^1$ is substituted with 2 substituent groups. In some embodiments, $Ar^1$ is substituted with 3 substituent groups. In some embodiments, $Ar^1$ is substituted with 4 substituent groups.

In embodiments, $Ar^1$ comprises one or more $R^1$ groups, wherein each $R^1$ is selected independently from hydrogen, halogen, CN, OH, $C_{1-3}$ alkyl optionally substituted with one or more halogens, and $C_{1-3}$ alkoxy. In embodiments, $Ar^1$ comprises a quantity of $R^1$ groups that is represented by m, wherein m is 1, 2, 3, or 4. When $R^1$ is present, $R^1$ can replace a hydrogen in the parent molecular structure. In embodiments, when $R^1$ is present and is a non-hydrogen moiety, $R^1$ represents a substituent group. In embodiments, $R^1$ is selected independently from halogen, CN, OH, $C_{1-3}$ alkyl optionally substituted with one or more halogens, and $C_{1-3}$ alkoxy.

Accordingly, it is also understood that for any value of m described herein, hydrogens are present as appropriate in order to complete valency requirements at constituent atoms of $Ar^1$ such that the molecule is a stable compound (e.g., the molecule is a compound which does not spontaneously undergo transformation such as by rearrangement, cyclization, elimination, or other reaction). Exemplary embodiments of $Ar^1$, $R^1$, and m are described herein.

In embodiments, $Ar^1$ is

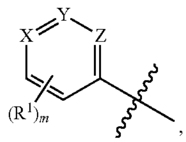

wherein

X is N or $CR^{1a}$;

Y and Z are independently CH or N; and m is 1, 2, 3 or 4.

In embodiments, $R^1$ is not a hydrogen. In embodiments, when $R^1$ is present and is a non-hydrogen moiety, $R^1$ represents a substituent group.

In embodiments, the value of m is based on the number of nitrogen atoms present in the ring. In embodiments, when one and only one of Y and Z is N, m is 1, 2, or 3. In embodiments, when each of Y and Z are N, m is 1 or 2.

In embodiments, X is N. In embodiments, X is $CR^{1a}$.

In embodiments, Y is CH. In embodiments, Z is N.

In embodiments, m is 1. In embodiments, m is 2. In embodiments, m is 3. In embodiments, m is 4.

In embodiments, Y and Z are both N, m is 1 or 2. In embodiments, m is 1, and any remaining unsubstituted carbon ring atoms are assumed bonded to hydrogen in order to fill the valence. In embodiments, m is 2.

In embodiments, Y and Z are both CH, and m is 1, 2, 3, or 4. In embodiments, m is 1, and any remaining unsubstituted carbon ring atoms are assumed bonded to hydrogen in order to fill the valence. In embodiments, m is 2, and any remaining unsubstituted carbon ring atoms are assumed bonded to hydrogen in order to fill the valence. In embodiments, m is 3, and any remaining unsubstituted carbon ring atoms are assumed bonded to hydrogen in order to fill the valence. In embodiments, m is 4.

In embodiments, one of Y and Z is CH and the other is N, and m is 1, 2, or 3. In embodiments, m is 1, and any remaining unsubstituted carbon ring atoms are assumed bonded to hydrogen in order to fill the valence. In embodiments, m is 2, and any remaining unsubstituted carbon ring atoms are assumed bonded to hydrogen in order to fill the valence. In embodiments, m is 3.

In embodiments, $Ar^1$ is

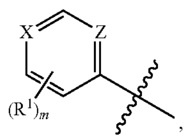

wherein

X is N or $CR^{1a}$;

Z is CH or N; and m is 1, 2, 3 or 4.

In embodiments, Z is N, and m is 1, 2 or 3. In embodiments, m is 1, and any remaining unsubstituted carbon ring atoms are assumed bonded to hydrogen in order to fill the valence. In embodiments, m is 2, and any remaining unsubstituted carbon ring atoms are assumed bonded to hydrogen in order to fill the valence. In embodiments, m is 3.

In embodiments, Z is CH, and m is 1, 2, 3, or 4. In embodiments, m is 1, and any remaining unsubstituted carbon ring atoms are assumed bonded to hydrogen in order to fill the valence. In embodiments, m is 2, and any remaining unsubstituted carbon ring atoms are assumed bonded to hydrogen in order to fill the valence. In embodiments, m is 3, and any remaining unsubstituted carbon ring atoms are assumed bonded to hydrogen in order to fill the valence. In embodiments, m is 4.

In embodiments, X is N. In embodiments, X is $CR^{1a}$.

In embodiments, $Ar^1$ is

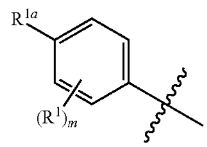

wherein m is 1, 2, 3 or 4.

In embodiments, m is 1, and any remaining unsubstituted carbon ring atoms are assumed bonded to hydrogen in order to fill the valence. In embodiments, m is 2, and any remaining unsubstituted carbon ring atoms are assumed bonded to hydrogen in order to fill the valence. In embodiments, m is 3, and any remaining unsubstituted carbon ring atoms are assumed bonded to hydrogen in order to fill the valence. In embodiments, m is 4.

In embodiments, $R^{1a}$ is H.

In embodiments, $R^{1a}$ is CN.

In embodiments, $R^{1a}$ is OH.

In embodiments, $R^{1a}$ is halogen. In embodiments, $R^{1a}$ is F. In embodiments, $R^{1a}$ is Cl. In embodiments, $R^{1a}$ is Br. In embodiments, $R^{1a}$ is I.

In embodiments, $R^{1a}$ is $C_{1-3}$ alkoxy. In embodiments, $R^{1a}$ is methoxy. In embodiments, $R^{1a}$ is ethoxy. In embodiments, $R^{1a}$ is propoxy.

In embodiments, $R^{1a}$ is $C_{1-3}$ alkyl.

In embodiments, $R^{1a}$ is unsubstituted $C_{1-3}$ alkyl. In embodiments, $R^{1a}$ is $CH_3$.

In embodiments, $R^{1a}$ is substituted $C_{1-3}$ alkyl. In embodiments, $R^{1a}$ is $C_{1-3}$ alkyl substituted with CN group. In embodiments, $R^{1a}$ is $CH_2CN$.

In embodiments, $R^1$, each time taken, is hydrogen.

In embodiments, $R^1$, each time taken, is CN.

In embodiments, $R^1$, each time taken, is OH.

In embodiments, $R^1$, each time taken, is halogen. In embodiments, a halogen is Cl. In embodiments, a halogen is Br. In embodiments, a halogen is I.

In embodiments, $R^1$, each time taken, is $C_{1-3}$ alkyl.

In embodiments, $R^1$, each time taken, is unsubstituted $C_{1-3}$ alkyl. In embodiments, $R^1$, each time taken, is $CH_3$.

In embodiments, $R^1$, each time taken, is substituted $C_{1-3}$ alkyl. In embodiments, $R^1$, each time taken, is $C_{1-3}$ alkyl substituted with one or more halogens. In embodiments, a halogen is F. In embodiments, a halogen is Cl. In embodiments, a halogen is Br. In embodiments, a halogen is I.

In embodiments, $R^1$, each time taken, is $CF_3$.

In embodiments, $R^1$, each time taken, is $C_{1-3}$ alkoxy. In embodiments, $R^1$, each time taken, is OMe.

In embodiments, $Ar^2$ is pyrid-2-yl, optionally substituted with one or more groups selected from halogen; amino; amide; OH; a sulfonyl group (e.g. $SO_2R^6$); a sulfinyl group (e.g. $SOR^7R^8$ or $SOR^9$); a carbonyl group (e.g. $COR^{10}$); a phosphoryl group (e.g. $POR^{12}R^{13}$); $C_{3-6}$ cycloalkyl; $C_{3-6}$ heterocycloalkyl optionally substituted with a sulfonyl group or =O; $C_{1-3}$ alkyl optionally substituted with carbonyl or one or more halogens; and heteroaryl optionally substituted with $C_{1-3}$ alkyl or phenyl. In embodiments, $Ar^2$ is unsubstituted pyrid-2-yl. In embodiments, $Ar^2$ is substituted pyrid-2-yl. In embodiments, $Ar^2$ is pyrid-2-yl substituted by 1 or 2 substituents as described herein. In embodiments, $Ar^2$ is pyrid-2-yl substituted by 3 substituents as described herein.

In embodiments, $Ar^2$ is

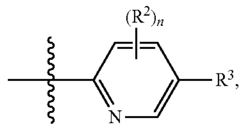

wherein $R^2$, each time taken, is independently selected from the group consisting of hydrogen, halogen, $NR^4R^5$, OH, $C_{1-3}$ alkyl, and $C_{3-6}$ cycloalkyl;

$R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens;

$R^6$ is $C_{1-3}$ alkyl, $NHCOR^{15}$, $NR^{16}R^{17}$, or phenyl;

$R^7$ is $C_{1-3}$ alkyl, $C_{3-5}$ cycloalkyl, phenyl, or $NR^{18}R^{19}$.

$R^8$ is NH or $NCH_3$;

$R^{10}$ is $C_{1-3}$ alkyl or $NHSO_2R^{20}$;

$R^{11}$ is $COR^{21}$ or $SO_2R^{22}$;

$R^9$, $R^{12}$, $R^{13}$ $R^{14}$, $R^{15}$, and $R^{20}$ are each independently $C_{1-3}$ alkyl;

$R^{21}$ is heterocycloalkyl, cycloalkyl, or $C_{1-3}$ alkyl;

$R^{22}$ is $NR^{23}R^{24}$ or $C_{1-3}$ alkyl optionally substituted with carboxyl;

$R^4$, $R^5$, $R^{16}$, $R^{17}$, $R^{18}$, $R^{19}$, $R^{23}$ and $R^{24}$ are each independently H or $C_{1-3}$ alkyl;

p is 1, 2, or 3; and n is 0, 1, 2 or 3.

In embodiments, n is 0. In embodiments, n is 1. In embodiments, n is 2. In embodiments, n is 3.

In embodiments, n is 0, and any remaining unsubstituted carbon ring atoms are assumed bonded to hydrogen in order to fill the valence.

In embodiments, n is 1, and any remaining unsubstituted carbon ring atoms are assumed bonded to hydrogen in order to fill the valence. In embodiments, n is 2, and any remaining unsubstituted carbon ring atoms are assumed bonded to hydrogen in order to fill the valence. In embodiments, n is 3.

In embodiments, $R^2$, each time taken, is hydrogen.

In embodiments, $R^2$, each time taken, is OH.

In embodiments, $R^2$, each time taken, is halogen. In embodiments, a halogen is Cl. In embodiments, a halogen is Br. In embodiments, a halogen is I.

In embodiments, $R^2$, each time taken, is $NR^4R^5$, wherein $R^4$ and $R^5$ are each independently H or $C_{1-3}$ alkyl.

In embodiments, $R^4$ and $R^5$ are both H.

In embodiments, one of $R^4$ and $R^5$ is H, and the other is $C_{1-3}$ alkyl. In embodiments, the $C_{1-3}$ alkyl is $CH_3$.

In embodiments, $R^2$, each time taken, is $C_{1-3}$ alkyl.

In embodiments, $R^2$, each time taken, is $C_{3-6}$ cycloalkyl.

In embodiments, $R^3$ is $SO_2R^6$, wherein $R^6$ is $C_{1-3}$ alkyl, $NHCOR^{15}$, $NR^{16}R^{17}$, or phenyl.

In embodiments, $R^3$ is $SOR^7R^8$, wherein $R^7$ is $C_{1-3}$ alkyl, $C_{3-5}$ cycloalkyl, phenyl, or $NR^{18}R^{19}$, and wherein $R^8$ is NH or $NCH_3$;

In embodiments, $R^3$ is $SOR^9$, wherein $R^9$ is $C_{1-3}$ alkyl.

In embodiments, $R^3$ is $COR^{10}$, wherein $R^{10}$ is $C_{1-3}$ alkyl or $NHSO_2R^{20}$, and wherein $R^{20}$ is $C_{1-3}$ alkyl.

In embodiments, $R^3$ is $(CH_2)_pCOOH$.

In embodiments, p is 1, 2, or 3. In embodiments, p is 1. In embodiments, p is 2. In embodiments, p is 3.

In embodiments, $R^3$ is $NHR^{11}$, wherein $R^{11}$ is $COR^{21}$ or $SO_2R^{22}$, wherein $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; and wherein $R^{23}$ and $R^{24}$ are each independently H or $C_{1-3}$ alkyl.

In embodiments, $R^3$ is $POR^{12}R^{13}$, wherein $R^{12}$ and $R^{13}$ are $C_{1-3}$ alkyl.

In embodiments, $R^3$ is halogen.

In embodiments, $R^3$ is cycloalkyl or heterocycloalkyl. In embodiments, the cycloalkyl or heterocycloalkyl is unsubstituted. In embodiments, the cycloalkyl or heterocycloalkyl is substituted.

In embodiments, $R^3$ is heteroaryl. In embodiments, the heteroaryl is unsubstituted. In embodiments, the heteroaryl is substituted.

In embodiments, $R^3$ is $C_{1-3}$ alkyl. In embodiments, the $C_{1-3}$ alkyl is unsubstituted. In embodiments, the $C_{1-3}$ alkyl is substituted with one or more halogens.

In embodiments, a compound of Formula (A) has the following structure, (I)

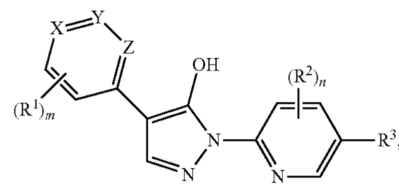

or a pharmaceutically acceptable salt thereof, wherein X, Y, Z, $R^1$, $R^2$, and $R^3$ are as defined anywhere herein.

In embodiments, a compound of Formula (A) or Formula (I) has the following structure, (II)

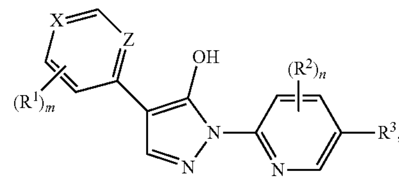

or a pharmaceutically acceptable salt thereof, wherein X, Z, $R^1$, $R^2$, and $R^3$ are as defined anywhere herein.

In embodiments, a compound of Formula (A), Formula (I), or Formula (II) has the following structure, (III)

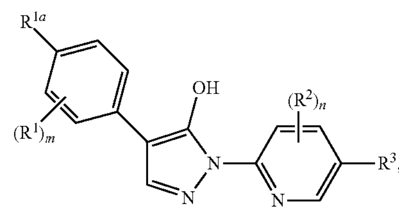

or a pharmaceutically acceptable salt thereof, wherein $R^{1a}$, $R^1$, $R^2$, and $R^3$ are as defined anywhere herein.

In embodiments, a compound of Formula (A), Formula (I), Formula (II), or Formula (III) has the following structure, (IV)

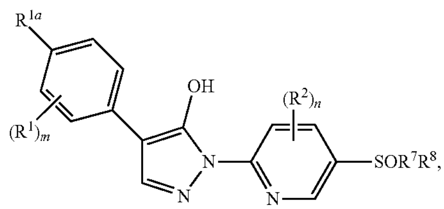

or a pharmaceutically acceptable salt thereof, wherein $R^{1a}$, $R^1$, and $R^2$ are as defined anywhere herein.

In embodiments, a compound of Formula (A), Formula (I), Formula (II), Formula (III) or Formula (IV) has the following structure, (IVa)

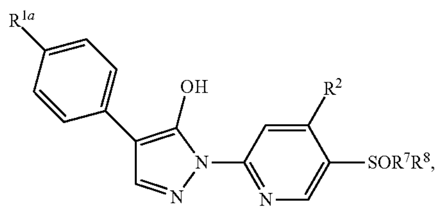

or a pharmaceutically acceptable salt thereof, wherein A, $R^{1a}$, and $R^2$ are as defined anywhere herein.

In embodiments, $R^7$ is $C_{1-3}$ alkyl.

In embodiments, $R^7$ is $C_{3-5}$ cycloalkyl.

In embodiments, $R^7$ is phenyl.

In embodiments, $R^7$ is $NR^{18}R^{19}$, wherein $R^{18}$ and $R^{19}$ are each independently H or $C_{1-3}$ alkyl.

In embodiments, $R^{18}$ and $R^{19}$ are both H.

In embodiments, $R^{18}$ and $R^{19}$ are both $C_{1-3}$ alkyl. In embodiments, $R^{18}$ and $R^{19}$ are both $CH_3$.

In embodiments, $R^{18}$ is H and $R^{19}$ is $C_{1-3}$ alkyl. In embodiments, $R^{19}$ is $CH_3$.

In embodiments, $R^8$ is NH.

In embodiments, $R^8$ is $NCH_3$.

In embodiments, a compound of Formula (A), Formula (I), Formula (II), or Formula (III) has the following structure, (V)

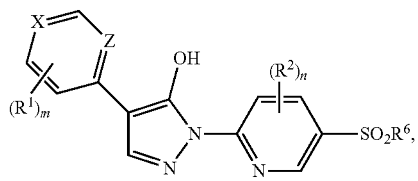

or a pharmaceutically acceptable salt thereof, wherein X, Z, $R^1$, and $R^2$ are as defined anywhere herein.

In embodiments, $R^6$ is $C_{1-3}$ alkyl. In embodiments, $R^6$ is $CH_3$.

In embodiments, $R^6$ is $NHCOR^5$, wherein $R^{15}$ is $C_{1-3}$ alkyl. In embodiments, $R^6$ is $NHCOCH_3$.

In embodiments, $R^6$ is $NR^{16}R^{17}$, wherein $R^{16}$ and $R^{17}$ are each independently H or $C_{1-3}$ alkyl.

In embodiments, $R^{16}$ and $R^{17}$ are both H.

In embodiments, $R^{16}$ and $R^{17}$ are both $C_{1-3}$ alkyl. In embodiments, $R^{16}$ and $R^{17}$ are both $CH_3$.

In embodiments, $R^{16}$ is H and $R^{17}$ is $C_{1-3}$ alkyl. In embodiments, $R^{17}$ is $CH_3$.

In embodiments, $R^6$ is phenyl.

In embodiments, a compound of Formula (A), Formula (I), Formula (II), or Formula (III) has the following structure, (VI)

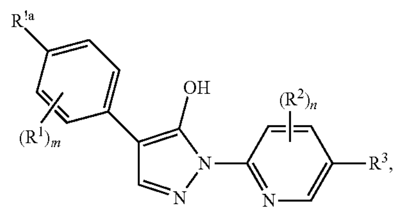

or a pharmaceutically acceptable salt thereof, wherein $R^{1a}$, $R^1$, and $R^2$ are as defined anywhere herein.

In embodiments, a compound of Formula (A), Formula (I), Formula (II), Formula (III) or Formula (VI) has the following structure, (VIa)

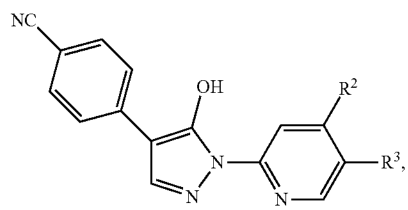

or a pharmaceutically acceptable salt thereof, wherein $R^2$ is as defined anywhere herein.

In embodiments, $R^3$ is cycloalkyl.

In embodiments, $R^3$ is unsubstituted cycloalkyl. In embodiments, $R^3$ is

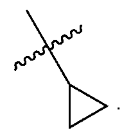 [SMILES: *C1CC1]

In embodiments, $R^3$ is substituted cycloalkyl. In embodiments, $R^3$ is cycloalkyl substituted with $SO_2R^{14}$ or =O, wherein $R^{14}$ is $C_{1-3}$ alkyl.

In embodiments, $R^3$ is heterocycloalkyl.

In embodiments, $R^3$ is unsubstituted heterocycloalkyl. In embodiments, $R^3$ is

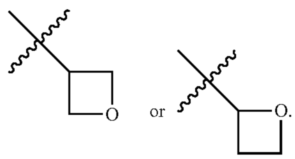 [SMILES: *C1COC1 ; *C1CCO1]

In embodiments, $R^3$ is substituted heterocycloalkyl. In embodiments, $R^3$ is heterocycloalkyl substituted with $SO_2R^{14}$ or =O, wherein $R^{14}$ is $C_{1-3}$ alkyl. In embodiments, $R^3$ is

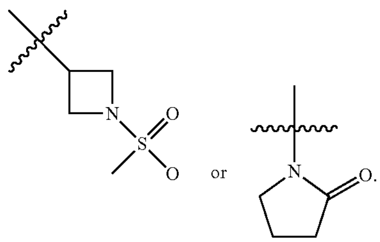

In embodiments, a compound of Formula (A), Formula (I), Formula (II), or Formula (III) has the following structure, (VII)

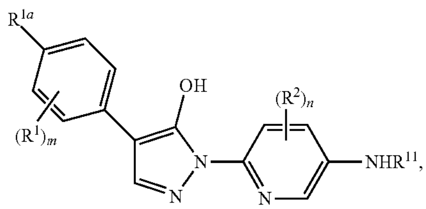

or a pharmaceutically acceptable salt thereof, wherein $R^{1a}$, $R^1$, and $R^2$ are as defined anywhere herein.

In embodiments, a compound of Formula (A), Formula (I), Formula (II), Formula (III) or Formula (VII) has the following structure, (VIIa)

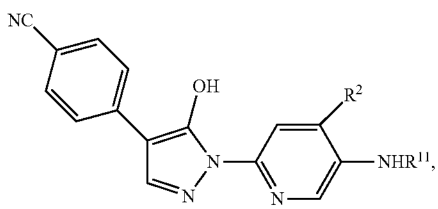

or a pharmaceutically acceptable salt thereof, wherein $R^2$ is as defined anywhere herein.

In embodiments, $R^{11}$ is $COR^{21}$, wherein $R^{21}$ is heterocycloalkyl, cycloalkyl, or $C_{1-3}$ alkyl.

In embodiments, $R^{21}$ is cycloalkyl. In embodiments, $R^{21}$ is

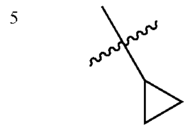

In embodiments, $R^{21}$ is heterocycloalkyl. In embodiments, $R^{21}$ is

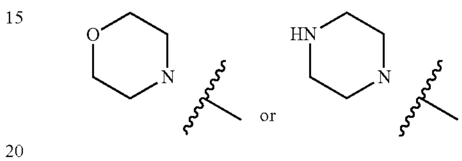

In embodiments, $R^{21}$ is $C_{1-3}$ alkyl. In embodiments, $R^{21}$ is $CH_2CH_3$.

In embodiments, $R^{11}$ is $SO_2R^{22}$, wherein $R^{22}$ is $NR^{23}R^{24}$ or $C_{1-3}$ alkyl optionally substituted with carboxyl, and wherein $R^{23}$ and $R^{24}$ are each independently H or $C_{1-3}$ alkyl.

In embodiments, $R^{22}$ is $C_{1-3}$ alkyl. In embodiments, $R^{22}$ is unsubstituted $C_{1-3}$ alkyl. In embodiments, $R^{22}$ is $C_{1-3}$ alkyl substituted with carboxyl group. In embodiments, $R^{22}$ is $CH_2COOH$.

In embodiments, $R^{22}$ is $NR^{23}R^{24}$, wherein $R^{23}$ and $R^{24}$ are independently H or $C_{1-3}$ alkyl.

In embodiments, $R^{23}$ and $R^{24}$ are both H.

In embodiments, $R^{23}$ and $R^{24}$ are both $C_{1-3}$ alkyl. In embodiments, $R^{23}$ and $R^{24}$ are both $CH_3$.

In embodiments, $R^{23}$ is H and $R^{24}$ is $C_{1-3}$ alkyl. In embodiments, $R^{24}$ is $CH_3$.

In embodiments, a compound of Formula (A), Formula (I), Formula (II), or Formula (III) has the following structure, (VIII)

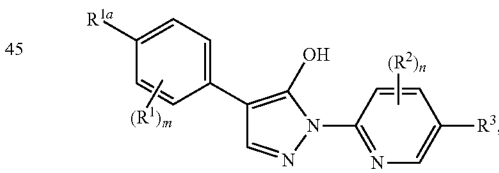

or a pharmaceutically acceptable salt thereof, wherein $R^{1a}$, $R^1$, and $R^2$ are as defined anywhere herein.

In embodiments, a compound of Formula (A), Formula (I), Formula (II), Formula (III) or Formula (VIII) has the following structure, (VIIIa)

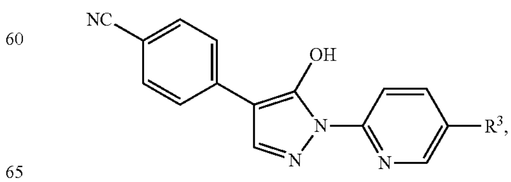

or a pharmaceutically acceptable salt thereof.

In embodiments, $R^3$ is heteroaryl. In embodiments, the heteroaryl is thiazole, oxazole, pyridine, triazole, tetrazole, or pyrazole.

In embodiments, $R^3$ is unsubstituted heteroaryl. In embodiments, $R^3$ is

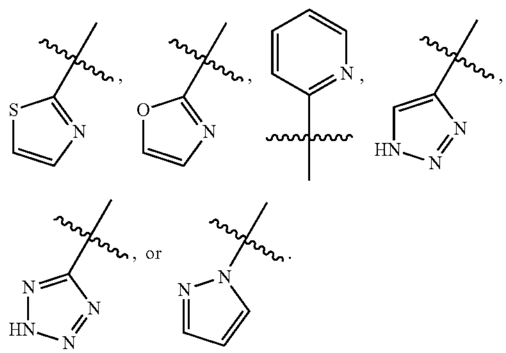

In embodiments, $R^3$ is heteroaryl substituted with $C_{1-3}$ alkyl or phenyl. In embodiments, $R^3$ is

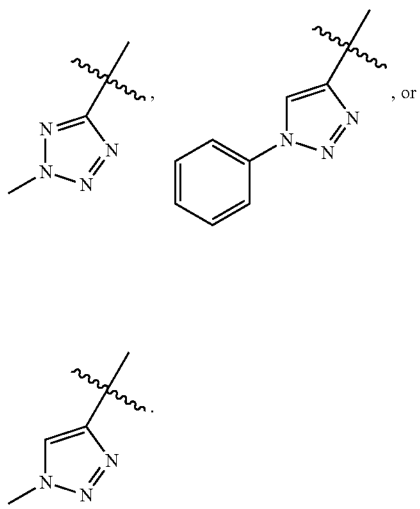

In embodiments, a compound of Formula (A), Formula (I), Formula (II), or Formula (III) has the following structure, (IX)

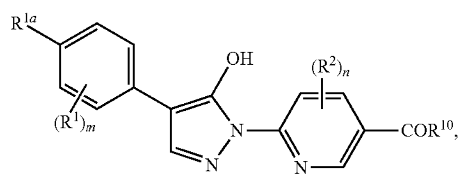

or a pharmaceutically acceptable salt thereof, wherein $R^{1a}$, $R^1$, and $R^2$ are as defined anywhere herein.

In embodiments, a compound of Formula (A), Formula (I), Formula (II), Formula (III) or Formula (IX) has the following structure, (IXa)

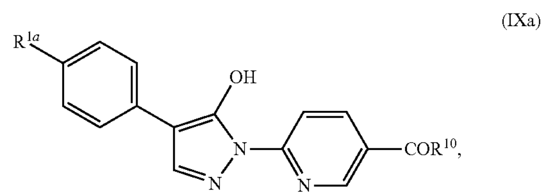

or a pharmaceutically acceptable salt thereof, wherein $R^{1a}$ is as defined anywhere herein.

In embodiments, $R^{10}$ is $C_{1-3}$ alkyl.

In embodiments, $R^{10}$ is $NHSO_2R^{20}$, wherein $R^{20}$ is $C_{1-3}$ alkyl. In embodiments, $R^{10}$ is $NHSO_2CH_3$.

In embodiments, a compound of Formula (A), Formula (I), Formula (II), or Formula (III) has the following structure, (X)

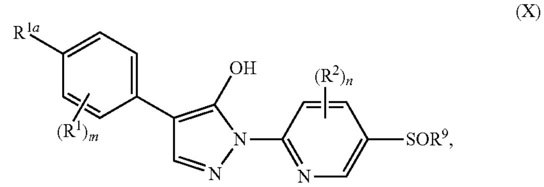

or a pharmaceutically acceptable salt thereof, wherein $R^{1a}$, $R^1$, and $R^2$ are as defined anywhere herein.

In embodiments, $R^9$ is $C_{1-3}$ alkyl.

In embodiments, a compound of Formula (A), Formula (I), Formula (II), or Formula (III) has the following structure, (XI)

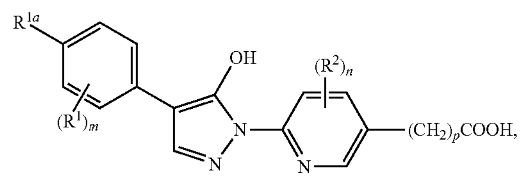

or a pharmaceutically acceptable salt thereof, wherein $R^{1a}$, $R^1$, and $R^2$ are as defined anywhere herein.

In embodiments, p is 1. In embodiments, p is 2. In embodiments, p is 3.

In embodiments, a compound of Formula (A), Formula (I), Formula (II), or Formula (III) has the following structure, (XII)

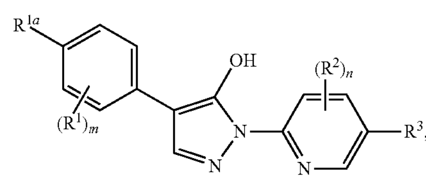

or a pharmaceutically acceptable salt thereof, wherein $R^{1a}$, $R^1$, and $R^2$ are as defined anywhere herein.

In embodiments, $R^3$ is halogen. In embodiments, $R^3$ is F. In embodiments, $R^3$ is Cl. In embodiments, $R^3$ is Br. In embodiments, $R^3$ is I.

In embodiments, a compound of Formula (A), Formula (I), Formula (II), or Formula (III) has the following structure, (XIII)

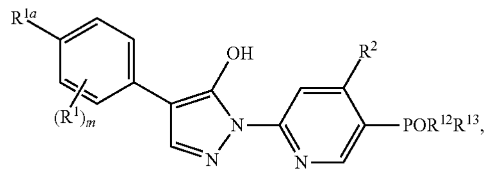

or a pharmaceutically acceptable salt thereof, wherein $R^{1a}$, $R^1$, and $R^2$ are as defined anywhere herein.

In embodiments, $R^{12}$ and $R^{13}$ are both $C_{1-3}$ alkyl. In embodiments, $R^{12}$ and $R^{13}$ are both $CH_3$.

Exemplary Compounds

In some embodiments, the PHD inhibitor compounds is any one of Compounds 1-33 or a pharmaceutically acceptable salt thereof.

| Cmpd No. | Structure |
|---|---|
| 1 | 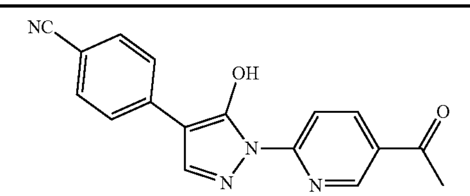 |
| 2 | 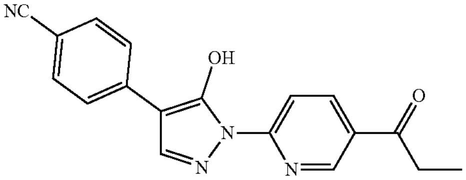 [SMILES: CCC(=O)c1ccc(-n2ncc(-c3ccc(C#N)cc3)c2O)nc1] |
| 3 | 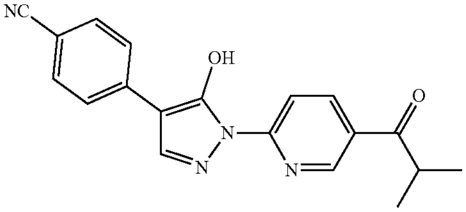 [SMILES: CC(C)C(=O)c1ccc(-n2ncc(-c3ccc(C#N)cc3)c2O)nc1] |
| 4 | 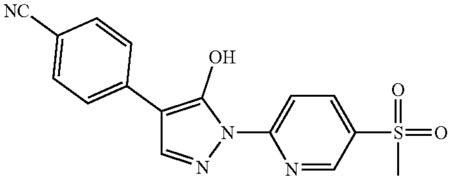 [SMILES: CS(=O)(=O)c1ccc(-n2ncc(-c3ccc(C#N)cc3)c2O)nc1] |
| 5 | 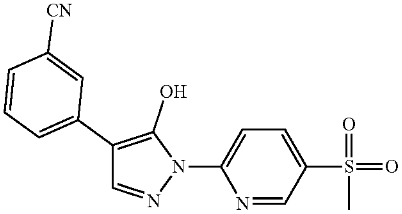 [SMILES: CS(=O)(=O)c1ccc(-n2ncc(-c3cccc(C#N)c3)c2O)nc1] |

-continued

| Cmpd No. | Structure |
|---|---|
| 6 | 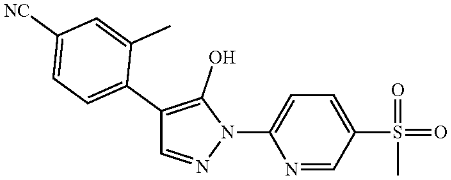 [SMILES: Cc1cc(C#N)ccc1-c1cnn(-c2ccc(S(C)(=O)=O)cn2)c1O] |
| 7 | 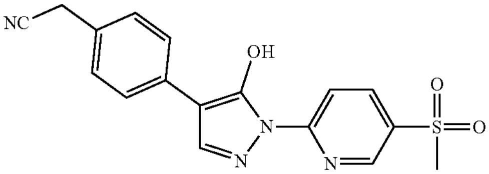 [SMILES: CS(=O)(=O)c1ccc(-n2ncc(-c3ccc(CC#N)cc3)c2O)nc1] |
| 8 | 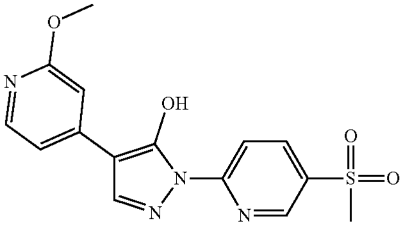 [SMILES: COc1cc(-c2cnn(-c3ccc(S(C)(=O)=O)cn3)c2O)ccn1] |
| 9 | 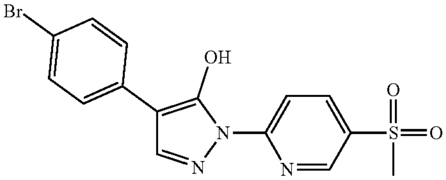 |
| 10 | 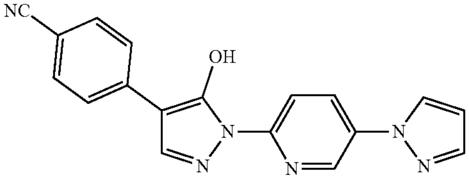 [SMILES: N#Cc1ccc(-c2cnn(-c3ccc(-n4cccn4)cn3)c2O)cc1] |
| 11 | 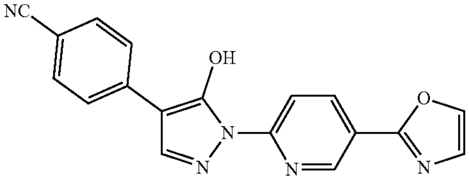 |
| 12 | 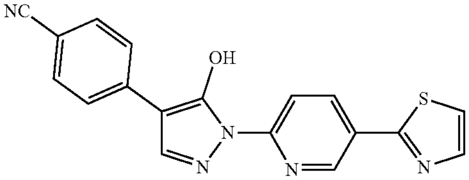 |

-continued
| Cmpd No. | Structure |
|---|---|
| 13 | 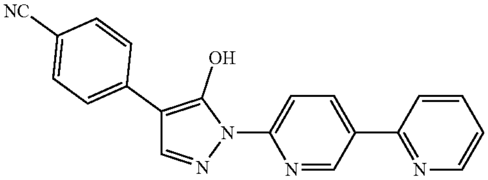 [SMILES: N#Cc1ccc(-c2cnn(-c3ccc(-c4ccccn4)cn3)c2O)cc1] |
| 14 | 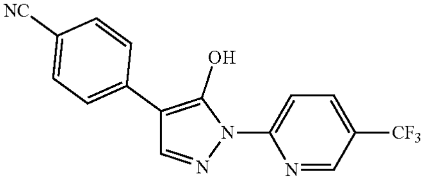 [SMILES: N#Cc1ccc(-c2cnn(-c3ccc(C(F)(F)F)cn3)c2O)cc1] |
| 15 | 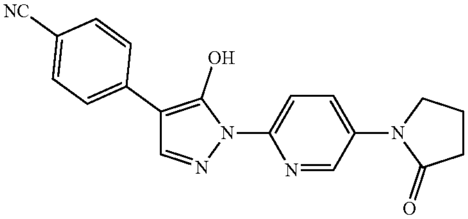 [SMILES: N#Cc1ccc(-c2cnn(-c3ccc(N4CCCC4=O)cn3)c2O)cc1] |
| 16 | 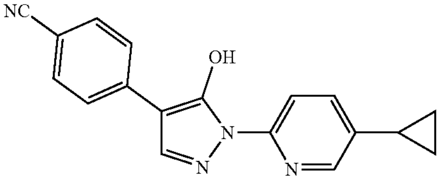 [SMILES: N#Cc1ccc(-c2cnn(-c3ccc(C4CC4)cn3)c2O)cc1] |
| 17 | 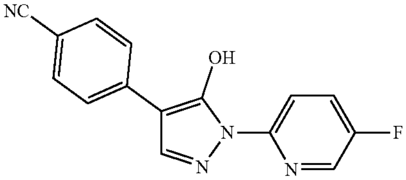 [SMILES: N#Cc1ccc(-c2cnn(-c3ccc(F)cn3)c2O)cc1] |
| 18 | 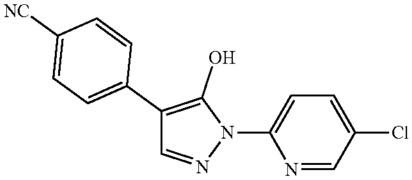 [SMILES: N#Cc1ccc(-c2cnn(-c3ccc(Cl)cn3)c2O)cc1] |
| 19 | 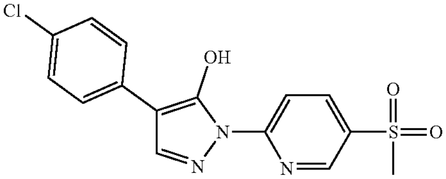 [SMILES: CS(=O)(=O)c1ccc(-n2ncc(-c3ccc(Cl)cc3)c2O)nc1] |
| 20 | 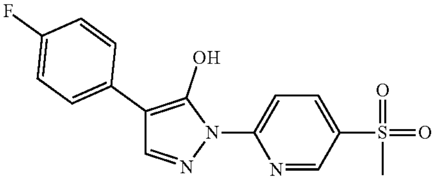 [SMILES: CS(=O)(=O)c1ccc(-n2ncc(-c3ccc(F)cc3)c2O)nc1] |
-continued
| Cmpd No. | Structure |
|---|---|
| 21 | 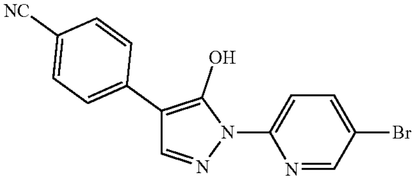 [SMILES: N#Cc1ccc(-c2cnn(-c3ccc(Br)cn3)c2O)cc1] |
| 22 | 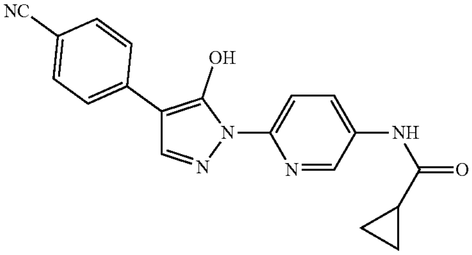 [SMILES: N#Cc1ccc(-c2cnn(-c3ccc(NC(=O)C4CC4)cn3)c2O)cc1] |
| 23 | 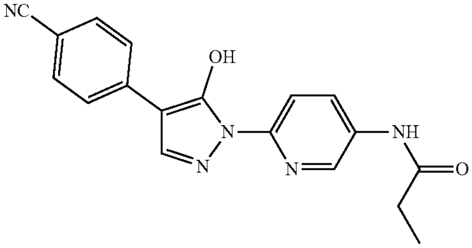 [SMILES: CCC(=O)Nc1ccc(-n2ncc(-c3ccc(C#N)cc3)c2O)nc1] |
| 24 | 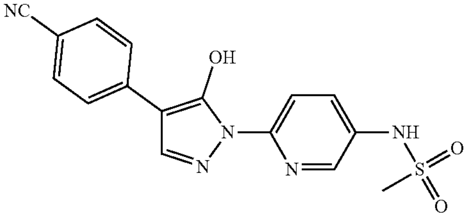 [SMILES: CS(=O)(=O)Nc1ccc(-n2ncc(-c3ccc(C#N)cc3)c2O)nc1] |
| 25 | 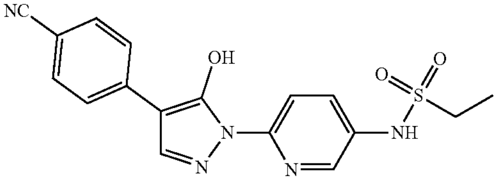 [SMILES: CCS(=O)(=O)Nc1ccc(-n2ncc(-c3ccc(C#N)cc3)c2O)nc1] |
| 26 | 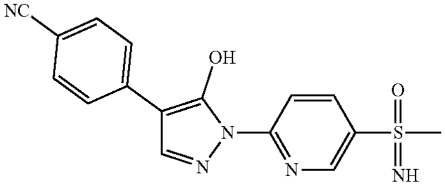 [SMILES: CS(=N)(=O)c1ccc(-n2ncc(-c3ccc(C#N)cc3)c2O)nc1] |
| 27 | 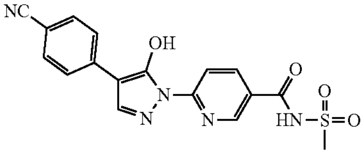 [SMILES: CS(=O)(=O)NC(=O)c1ccc(-n2ncc(-c3ccc(C#N)cc3)c2O)nc1] |

-continued

| Cmpd No. | Structure |
|---|---|
| 28 | 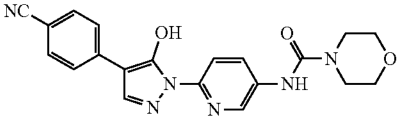 [SMILES: N#Cc1ccc(-c2cnn(-c3ccc(NC(=O)N4CCOCC4)cn3)c2O)cc1] |
| 29 | 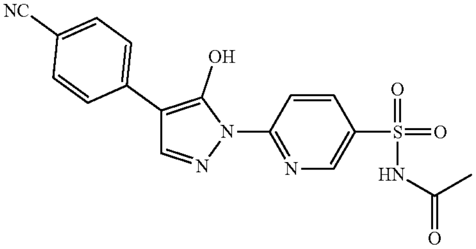 [SMILES: CC(=O)NS(=O)(=O)c1ccc(-n2ncc(-c3ccc(C#N)cc3)c2O)nc1] |
| 30 | 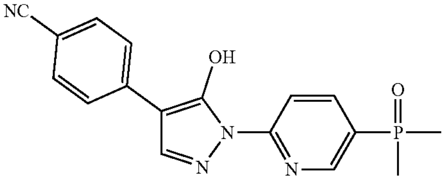 [SMILES: CP(C)(=O)c1ccc(-n2ncc(-c3ccc(C#N)cc3)c2O)nc1] |
| 31 | 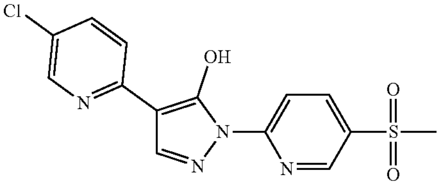 [SMILES: CS(=O)(=O)c1ccc(-n2ncc(-c3ccc(Cl)cn3)c2O)nc1] |
| 32 | 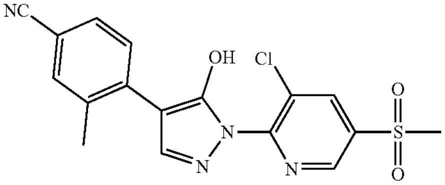 [SMILES: Cc1cc(C#N)ccc1-c1cnn(-c2ncc(S(C)(=O)=O)cc2Cl)c1O] |
| 33 | 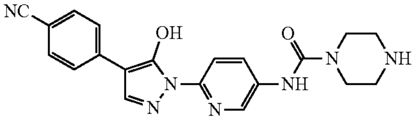 [SMILES: N#Cc1ccc(-c2cnn(-c3ccc(NC(=O)N4CCNCC4)cn3)c2O)cc1] |

Isotopologues

It should be understood that in the compounds described herein (e.g., a compound of any one of Formulas (A) and (I)-(XIII) such as any one of compounds 1-33), the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of the compounds described herein (e.g., a compound of any one of Formulas (A) and (I)-(XIII) such as any one of compounds 1-33). For example, different isotopic forms of hydrogen (H) include protium ($^1H$), deuterium ($^2H$), and tritium ($^3H$). Protium is the predominant hydrogen isotope found in nature.

In some embodiments, one or more of the hydrogens of the compounds described herein (e.g., a compound of any one of Formulas (A) and (I)-(XIII) such as any one of compounds 1-33) is replaced by a deuterium. Enriching for deuterium may afford certain therapeutic advantages, such as increasing in vivo half-life or reducing dosage requirements, or may provide a compound useful as a standard for characterization of biological samples. In some embodiments, one or more of the hydrogens of the compounds described herein (e.g., a compound of any one of Formulas (A) and (I)-(XIII) such as any one of compounds 1-33) is replaced by tritium. Tritium is radioactive and may therefore provide for a radiolabeled compound, useful as a tracer in metabolic or kinetic studies.

Isotopic-enrichment of compounds disclosed herein (e.g., a compound of any one of Formulas (A) and (I)-(XIII) such as any one of compounds 1-33), may be achieved without undue experimentation by conventional techniques well known to those skilled in the art or by processes analogous to those described in the Schemes and Examples herein using appropriate isotopically-enriched reagents and/or intermediates.

The term "isotopologue" refers to a species that has the same chemical structure and formula as a specific compound provided herein, with the exception of the positions of isotopic substitution and/or level of isotopic enrichment at one or more positions, e.g., hydrogen vs. deuterium. Thus, the term "compound," as used herein, encompasses a collection of molecules having identical chemical structure, but also having isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound provided depends upon a number of factors including, but not limited to, the isotopic purity of deuterated reagents used to make the compound and the efficiency of incorporation of deuterium in the various synthesis steps used to prepare the compound.

When a position is designated as "H" or "hydrogen", the position is understood to have hydrogen at its natural abundance isotopic composition. When a position is designated as "D" or "deuterium", the position is understood to have deuterium at an abundance that is at least 3340 times greater than the natural abundance of deuterium, which is 0.015% (i.e., the term "D" or "deuterium" indicates at least 50.1% incorporation of deuterium).

In embodiments, a compound provided herein may have an isotopic enrichment factor for each deuterium present at a site designated as a potential site of deuteration on the compound of at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Synthesis of Compounds of the Inventions

The compounds described herein (e.g., a compound of any one of Formulas (A) and (I)-(XIII) such as any one of compounds 1-33) can be prepared according to methods known in the art, including the exemplary syntheses of the Examples provided herein.

Abbreviations and Acronyms Used Herein Including the Following

| Term | Acronym |
|---|---|
| 4-Dimethylaminopyridine | DMAP |
| Acetyl | Ac |
| Aqueous | aq. |
| Benzyl | Bn |
| tert-Butyloxy carbonyl | Boc |
| Broad singlet | brs |
| Dichloromethane | DCM |
| Dimethylsulfoxide | DMSO |
| Doublet | d |
| Electrospray ionization | ESI |
| Equivalent | eq |
| Ethyl acetate | EtOAc |
| Gram | g |
| Hexanes | Hex |
| High performance liquid chromatography | HPLC |
| Hour | hr |
| Isopropyl | i-Pr |
| Liquid chromatography-mass spectrometry | LCMS |
| Megahertz | MHz |
| meta-Chloroperoxybenzoic acid | m-CPBA |
| Methanol | MeOH |
| Milligram | mg |
| Milliliter | mL |
| Minute | min |
| Molarity | M |
| Multiplet | m |
| N,N-Diisopropylethylamine | DIPEA |
| N,N-Dimethylformamide | DMF |
| N,N-dimethylformamide dimethyl acetal | DMF-DMA |
| Normal | N |
| Nuclear magnetic resonance | NMR |
| Palladium on carbon | Pd/C |
| Pentet | p |
| Petroleum ether | PE |
| Phenyl | Ph |
| Quartet | q |
| Room temperature | RT |
| Singlet | s |
| Tetrahydrofuran | THF |
| Thin layer chromatography | TLC |
| Triethylamine | TEA |
| Trifluoroacetic acid | TFA |
| Triplet | t |

Compositions and Methods

The invention provides for use of a compound of any one of Formulas (A) and (I)-(XIII), or a pharmaceutically acceptable salt thereof, for the manufacture of a medicament for use in treating various conditions or disorders as described herein. In one embodiment, a pharmaceutical composition is provided comprising at least one compound of any one of Formulas (A) and (I)-(XIII), or a pharmaceutically acceptable salt thereof, and a pharmaceutically acceptable excipient or carrier. In various embodiments, the medicament or pharmaceutical composition can further comprise or be used in combination with at least one additional therapeutic agent.

The compounds of the present invention, or medicaments or compositions comprising the compounds, can be used to inhibit the activity of PHD. Inhibition of PHD may be of particular benefit in treating diseases including heart (e.g. ischemic heart disease, congestive heart failure, and valvular heart disease), lung (e.g., acute lung injury, pulmonary hypertension, pulmonary fibrosis, and chronic obstructive pulmonary disease), liver (e.g. acute liver failure and liver fibrosis and cirrhosis), and kidney (e.g. acute kidney injury and chronic kidney disease) disease.

In one embodiment, the method of the invention comprises administering to a patient in need a therapeutically effective amount of a compound of any one of Formulas (A) and (I)-(XIII), or a pharmaceutically acceptable salt thereof, or a pharmaceutical composition comprising one or more compounds of any one of Formulas (A) and (I)-(XIII).

The invention is also directed to a method of inhibiting the activity of PHD. In one embodiment, the method comprises contacting PHD with an effective amount of one or more compounds selected from the group comprising compounds of any one of Formulas (A) and (I)-(XIII), or a pharmaceutically acceptable salt thereof.

In still other embodiments, the compounds disclosed herein (e.g., a compound of any one of Formulas (A) and (I)-(XIII) such as any one of compounds 1-33), or a pharmaceutically acceptable salt thereof, are useful for the treatment or prevention of anemia comprising treatment of anemic conditions associated with chronic kidney disease, polycystic kidney disease, aplastic anemia, autoimmune hemolytic anemia, bone marrow transplantation anemia, Churg-Strauss syndrome, Diamond Blackfan anemia, Fanconi's anemia, Felty syndrome, graft versus host disease, hematopoietic stem cell transplantation, hemolytic uremic syndrome, myelodysplastic syndrome, nocturnal paroxysmal hemoglobinuria, osteomyelofibrosis, pancytopenia, pure red-cell aplasia, purpura Schoenlein-Henoch, refractory anemia with excess of blasts, rheumatoid arthritis, Shwachman syndrome, sickle cell disease, thalassemia major, thalassemia minor, thrombocytopenic purpura, anemic or non-anemic patients undergoing surgery, anemia associated with or secondary to trauma, sideroblastic anemia, anemic secondary to other treatment including: reverse transcriptase inhibitors to treat HIV, corticosteroid hormones, cyclic cisplatin or non-cisplatin-containing chemotherapeutics, vinca alkaloids, mitotic inhibitors, topoisomerase II inhibitors, anthracyclines, alkylating agents, particularly anemia secondary to inflammatory, aging and/or chronic diseases. PHD1 inhibition may also be used to treat symptoms of anemia including chronic fatigue, pallor, and dizziness.

In other embodiments, the compounds disclosed herein (e.g., a compound of Formulas (A) and (I)-(XIII) such as any one of compounds 1-33), or a pharmaceutically acceptable salt thereof, are useful for the treatment or prevention of diseases of metabolic disorders, including but not limited to diabetes and obesity.

In yet other embodiments, the compounds disclosed herein (e.g., a compound of Formulas (A) and (I)-(XIII) such as any one of compounds 1-33), or a pharmaceutically acceptable salt thereof, are useful for the treatment or prevention of vascular disorders. These include but are not limited to hypoxic or wound healing related diseases requiring pro-angiogenic mediators for vasculogenesis, angiogenesis, and arteriogenesis In still other embodiments, the compounds disclosed herein (e.g., a compound of Formulas (A) and (I)-(XIII) such as any one of compounds 1-33), or a pharmaceutically acceptable salt thereof, are useful for the treatment or prevention of ischemia reperfusion injury. These include but are not limited to stroke, myocardial infarction, and acute kidney injury).

In other embodiments, the compounds disclosed herein (e.g., a compound of Formulas (A) and (I)-(XIII) such as any one of compounds 1-33), or a pharmaceutically acceptable salt thereof, are useful in the treatment of inflammatory bowel disease. These include but are not limited to ulcerative colitis, and Crohn's disease.

In other embodiments, the compounds disclosed herein (e.g., a compound of Formulas (A) and (I)-(XIII) such as any one of compounds 1-33), or a pharmaceutically acceptable salt thereof, are useful in the treatment of cancers, such as colorectal cancer.

In other embodiments, the compounds disclosed herein (e.g., a compound of Formulas (A) and (I)-(XIII) such as any one of compounds 1-33), or a pharmaceutically acceptable salt thereof, are useful in the treatment of atherosclerosis.

In other embodiments, the compounds disclosed herein (e.g., a compound of Formulas (A) and (I)-(XIII) such as any one of compounds 1-33), or a pharmaceutically acceptable salt thereof, are useful in the treatment of cardiovascular disease.

In other embodiments, the compounds disclosed herein (e.g., a compound of Formulas (A) and (I)-(XIII) such as any one of compounds 1-33), or a pharmaceutically acceptable salt thereof, are useful in the treatment of a disease or condition of the eye. These include but are not limited to radiation retinopathy, retinopathy of prematurity, diabetic retinopathy, age-related macular degeneration, and ocular ischemia.

In other embodiments, the compounds disclosed herein (e.g., a compound of Formulas (A) and (I)-(XIII) such as any one of compounds 1-33), or a pharmaceutically acceptable salt thereof, are useful in the treatment of a disease that is associated with hyperoxia.

In other embodiments, the compounds disclosed herein (e.g., a compound of Formulas (A) and (I)-(XIII) such as any one of compounds 1-33), or a pharmaceutically acceptable salt thereof, are useful in the treatment of bronchopulmonary dysplasia (BPD).

In yet other embodiments, the compounds disclosed herein (e.g., a compound of Formulas (A) and (I)-(XIII) such as any one of compounds 1-33), or a pharmaceutically acceptable salt thereof, are useful in the treatment of heart diseases. The conditions include but are not limited to postoperative myocardial ischemia in pancreatic surgery, myocardial injury after percutaneous coronary intervention (PCI), myocardial injury after non-cardiac surgery, perioperative myocardial ischemia in elective operation of abdominal aortic aneurysm, myocardial injury after PCI, myocardial damage in patients undergoing coronary artery bypass graft (CABG) surgery, Minimally invasive mitral valve (MIMV) repair or replacement, adult patient undergoing open heart surgery, chronic heart failure, NYHA class II-IV.

In other embodiments, the compounds disclosed herein (e.g., a compound of Formulas (A) and (I)-(XIII) such as any one of compounds 1-33), or a pharmaceutically acceptable salt thereof, are useful in the treatment of lung diseases. The conditions include but are not limited to lung injury during elective lung lobectomy, lung injury during CABG surgery, lung transplantation.

In other embodiments, the compounds disclosed herein (e.g., a compound of Formulas (A) and (I)-(XIII) such as any one of compounds 1-33), or a pharmaceutically acceptable salt thereof, are useful in the treatment of liver disease. The conditions include but are not limited to non-alcoholic steatohepatitis (NASH).

In other embodiments, the compounds disclosed herein (e.g., a compound of Formulas (A) and (I)-(XIII) such as any one of compounds 1-33), or a pharmaceutically acceptable salt thereof, are useful in the treatment of kidney disease. The conditions include but are not limited to contrast-induced acute kidney injury, stage III-IV chronic kidney disease undergoing planned coronary angiography, acute kidney injury in patients undergoing valvular heart surgery, non-dialysis dependent chronic kidney disease, chronic kidney disease patients initiating dialysis, non-dialysis dependent chronic kidney disease.

In addition, the compounds disclosed herein (e.g., a compound of any one of Formulas (A) and (I)-(XIII) such as any one of compounds 1-33), or a pharmaceutically acceptable salt thereof, may be used in combination with additional active ingredients in the treatment of the above conditions. The additional compounds may be co-administered separately with the compounds disclosed herein (e.g., a compound of any one of Formulas (A) and (I)-(XIII) such as any one of compounds 1-33), or a pharmaceutically acceptable salt thereof, or included with an additional active ingredient in a pharmaceutical composition according to the invention. In an exemplary embodiment, additional active ingredients are those that are known or discovered to be effective in the treatment of conditions, disorders, or diseases mediated by PHD enzyme or that are active against another targets associated with the particular condition, disorder, or disease, such as an alternate PHD modulator. The combination may serve to increase efficacy (e.g., by including in the combination a compound potentiating the potency or effectiveness of a compound according to the invention), decrease one or more side effects, or decrease the required dose of the compound according to the invention.

The compounds of the invention are used, alone or in combination with one or more other active ingredients, to formulate pharmaceutical compositions of the invention. A pharmaceutical composition of the invention comprises: (a) an effective amount of the compounds disclosed herein (e.g., a compound of any one of Formulas (A) and (I)-(XIII) such as any one of compounds 1-33), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable excipients may also include antioxidants. Such antioxidants may be used in a pharmaceutical composition or in a storage medium to prolong the shelf-life of the drug product.

Pharmaceutical Formulations and Routes of Administration

The compounds and compositions of the present invention can be delivered directly or in pharmaceutical compositions or medicaments along with suitable carriers or excipients, as is well known in the art. Present methods of treatment can comprise administration of an effective amount of a compound of the invention to a subject in need. In a preferred embodiment, the subject is a mammalian subject, and in a most preferred embodiment, the subject is a human subject.

An effective amount of such compound, composition, or medicament can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. See, e.g., the U.S. Pharmacopeia (USP), Japanese Pharmacopoeia (JP), European Pharmacopoeia (EP), and British pharmacopeia (BP); the U.S. Food and Drug.

Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott NY; etc.) [0149] Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art.

For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherents, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compounds and compositions formulated for parenteral administration by injection are usually sterile and can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the compounds of the invention are well-known in the art and include water-based solutions containing a base, such as, for example, sodium hydroxide, to form an ionized compound; sucrose or sodium chloride as a tonicity agent; and a buffer, for example, a buffer that contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays. In certain some embodiments, a compound of the disclosure is formulated for oral administration. An exemplary dose of a compound of the disclosure in a pharmaceutical formulation for oral administration is from about 0.5 to about 10 mg/kg body weight of subject. In some embodiments, a pharmaceutical formulation comprises from about 0.7 to about 5.0 mg/kg body weight of subject, or alternatively, from about 1.0 to about 2.5 mg/kg body weight of subject. A typical dosing regimen for oral administration would be administration of the pharmaceutical formulation for oral administration three times per week, two times per week, once per week or daily.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of compound or composition administered may be dependent on a variety of factors, including the sex, age, and weight of the subject being treated, the severity of the affliction, the manner of administration, and the judgment of the prescribing physician.

The present compounds and compositions may, if desired, be presented in a pack or dispenser device containing one or more unit dosage forms containing the active ingredient. Such a pack or device may, for example, comprise metal or plastic foil, such as a blister pack; or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein and are specifically contemplated.

EXEMPLIFICATION

Purity Determination with HPLC

Purity of the compounds and their synthetic intermediates were determined with reverse phase HPLC using either one of the methods described below:

Method A: Mobile Phase: A: Water (0.01% TFA) B: Acetonitrile (0.01% TFA); Gradient Phase: 5% B increase to 95% B within 1.4 min, 95% B with 1.6 min (total run time:3 min); Flow Rate: 2.3 mL/min. Column: SunFire C18, 4.6*50 mm, 3.5 μm; Column Temperature: 50° C. Detectors: ADC ELSD, DAD (214 nm and 254 nm), ES-API.

Method B: Mobile Phase: A: Water (10 mM NH4HCO3) B: Acetonitrile; Gradient Phase: 5% to 95% B within 1.5 min, 95% B with 1.5 min (total run time:3 min); Flow Rate: 2.0 mL/min; Column: XBridge C18, 4.6*50 mm, 3.5 μm; Column Temperature: 40° C. Detectors: ADC ELSD, DAD (214 nm and 254 nm), MSD (ES-API).

Synthesis for Exemplary Compounds

Example 1: Preparation of Compound 1 tert-butyl 6-chloronicotinate

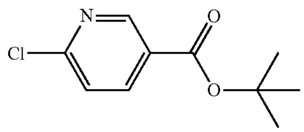

To a solution of 6-chloronicotinic acid (5.0 g, 6.37 mmol) and 4-dimethylaminopyridine (0.39 g, 0.64 mmol) in tetrahydrofuran (50.0 mL) was added di-tert-butyl dicarbonate (10.41 g, 47.77 mmol). The reaction mixture was refluxed for 4 hr and concentrated. The residue was purified by flash chromatography (petroleum ether/ethyl acetate=10/1) to afford tert-butyl 6-chloronicotinate (5.5 g, 5.17 mmol, 81.12% yield) as yellow solid. LCMS: m/z=214.0 $(M+H)^+$, retention time 1.83 min (Method A).

tert-butyl 6-hydrazineylnicotinate

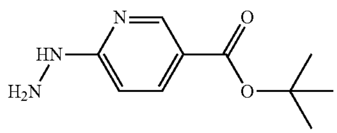

To a solution of tert-butyl 6-chloronicotinate (5.5 g, 25.82 mmol) in ethanol (25.0 mL) was added hydrazine hydrate (6.46 g, 129.11 mmol, 85% in water). The mixture was stirred at 100° C. for 2 h. The mixture was cooled and concentrated to dryness. The residue was partitioned between ethyl acetate and water. The organic phase was washed with brine, dried over sodium sulfate and concentrated. The residue was triturated with petroleum ether and filtered to afford tert-butyl 6-hydrazineylnicotinate (5.0 g, 23.9 mmol, 92.76% yield) as yellow solid. LCMS: m/z=210.0 $(M+H)^+$, retention time 1.19 min (Method A).

tert-butyl 6-(4-(4-cyanophenyl)-5-hydroxy-1H-pyrazol-1-yl)nicotinate

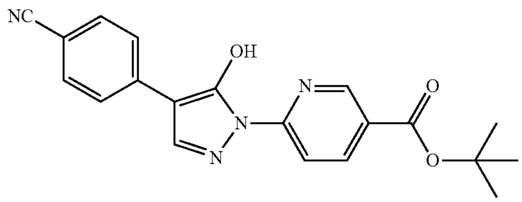 [SMILES: CC(C)(C)OC(=O)c1ccc(-n2ncc(-c3ccc(C#N)cc3)c2O)nc1]

To a solution of ethyl (E)-2-(4-cyanophenyl)-3-(dimethylamino)acrylate (2.5 g, 10.86 mmol) and tert-butyl 6-hydrazineylnicotinate (2.27 g, 10.86 mmol) in ethanol (25.0 mL) was added p-toluenesulfonic acid monohydrate (410 mg, 2.17 mmol). The mixture was stirred at 80° C. for 12 hr and concentrated to dryness. The residue was purified by flash chromatography (methanol/dichloromethane=1/8) to afford tert-butyl 6-(4-(4-cyanophenyl)-5-hydroxy-1H-pyrazol-1-yl)nicotinate (3.0 g, 8.35 mmol, 76.92% yield) as yellow solid. LCMS: m/z=363.1 $(M+H)^+$, retention time 1.98 min (Method A).

6-(4-(4-cyanophenyl)-5-hydroxy-1H-pyrazol-1-yl) nicotinic acid

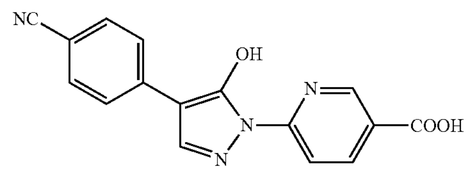 [SMILES: N#Cc1ccc(-c2cnn(-c3ccc(C(=O)O)cn3)c2O)cc1]

To a solution of tert-butyl 6-(4-(4-cyanophenyl)-5-hydroxy-1H-pyrazol-1-yl)nicotinate (1.00 g, 2.76 mmol) in dichloromethane (10.0 mL) was added trifluoroacetic acid (5.0 mL). The mixture was stirred at 40° C. for 2 hr and concentrated. The residue was triturated with ethyl acetate and filtered to afford 6-(4-(4-cyanophenyl)-5-hydroxy-1H-pyrazol-1-yl)nicotinic acid (900 mg, crude) as yellow solid. LCMS: m/z=307.0 $(M+H)^+$, retention time 1.77 min (Method A).

6-(4-(4-cyanophenyl)-5-hydroxy-1H-pyrazol-1-yl) nicotinoyl chloride

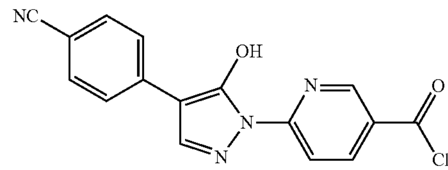 [SMILES: N#Cc1ccc(-c2cnn(-c3ccc(C(=O)Cl)cn3)c2O)cc1]

To a solution of 6-(4-(4-cyanophenyl)-5-hydroxy-1H-pyrazol-1-yl)nicotinic acid (900 mg, 2.94 mmol) in dichloromethane (10.0 mL) was added thionyl chloride (10.0 mL). The mixture was stirred at 40° C. for 3 hr and concentrated to dryness. The crude product (900 mg) was obtained and used to the next step. LCMS: m/z=325.1 $(M+H)^+$, retention time 1.96 min (Method A).

6-(4-(4-cyanophenyl)-5-hydroxy-1H-pyrazol-1-yl)-N-methoxy-N-methylnicotinamide

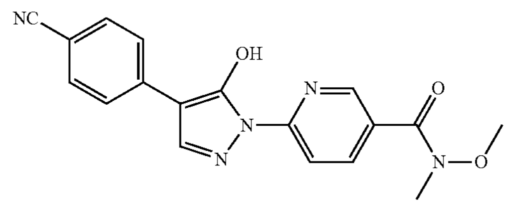 [SMILES: CON(C)C(=O)c1ccc(-n2ncc(-c3ccc(C#N)cc3)c2O)nc1]

To a solution of N, O-dimethylhydroxylamine hydrochloride (407.43 mg, 4.16 mmol) and N,N-diisopropylethylamine (1.07 g, 8.31 mmol) in dichloromethane (5.0 mL) was added 6-(4-(4-cyanophenyl)-5-hydroxy-1H-pyrazol-1-yl) nicotinoyl chloride (900 mg, 2.77 mmol) at 0° C. The mixture was stirred at 0° C. for 3 hr and concentrated to give dryness. The residue was purified by flash chromatography (dichloromethane/methanol=10/1) to obtain 6-(4-(4-cyanophenyl)-5-hydroxy-1H-pyrazol-1-yl)-N-methoxy-N-methylnicotinamide (900 mg, 2.58 mmol, 93.17% yield) as yellow solid. LCMS: m/z=350.1 $[M+H]^+$, retention time 1.63 min (Method A).

4-(1-(5-acetylpyridin-2-yl)-5-hydroxy-1H-pyrazol-4-yl)benzonitrile

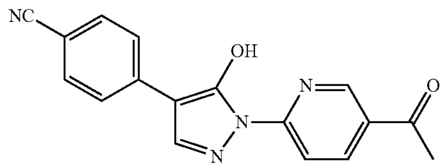 [SMILES: CC(=O)c1ccc(-n2ncc(-c3ccc(C#N)cc3)c2O)nc1]

To a solution of methylmagnesium bromide (0.76 mL, 2.29 mmol, 3M in ether) in anhydrous tetrahydrofuran (5.0 mL) was added 6-(4-(4-cyanophenyl)-5-hydroxy-1H-pyrazol-1-yl)-N-methoxy-N-methylnicotinamide (200 mg, 0.57 mmol) at −20° C. The mixture was allowed to warm up to 0° C. and left stirring for another one hour. The reaction was quenched with water and extracted twice with ethyl acetate. The organic layer was washed with brine, dried over sodium sulfate and concentrated under reduced pressure. The crude product was purified by flash chromatography (petroleum ether/ethyl acetate=1/1) to give 4-(1-(5-acetylpyridin-2-yl)-5-hydroxy-1H-pyrazol-4-yl)benzonitrile (35 mg, 0.11 mmol, 20.23% yield) as white solid. LCMS: m/z=305.0 $(M+H)^+$, retention time 4.504 min (Method A). $^1H$ NMR (400 MHz, DMSO-$d_6$) δ 9.00 (s, 1H), 8.58-8.43 (m, 3H), 8.18-8.09 (m, 3H), 7.73-7.69 (m, 2H), 2.63 (s, 3H).

Example 2: Preparation of Compound 2

4-(5-hydroxy-1-(5-propionylpyridin-2-yl)-1H-pyrazol-4-yl)benzonitrile

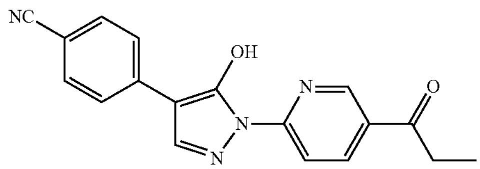 [SMILES: CCC(=O)c1ccc(-n2ncc(-c3ccc(C#N)cc3)c2O)nc1]

To a solution of ethylmagnesium bromide (0.76 mL, 2.29 mmol, 3M in ether) in anhydrous tetrahydrofuran (5.0 mL) was added 6-(4-(4-cyanophenyl)-5-hydroxy-TH-pyrazol-1-yl)-N-methoxy-N-methylnicotinamide (Intermediate from Example 1) (200 mg, 0.57 mmol) at −20° C. The mixture was allowed to warm up to 0° C. and left stirring for another one hour. The reaction was quenched with water and extracted twice with ethyl acetate. The organic layer was washed with brine, dried over sodium sulfate and concentrated under reduced pressure. The crude product was purified by flash chromatography (petroleum ether/ethyl acetate=1/1) to give 4-(5-hydroxy-1-(5-propionylpyridin-2-yl)-1H-pyrazol-4-yl)benzonitrile (25 mg, 0.08 mmol, 13.81% yield) as white solid. LCMS: m/z=319.0 $(M+H)^+$, retention time 5.01 min (Method A). $^1H$ NMR (400 MHz, DMSO-$d_6$) δ 13.56 (s, 1H), 9.02 (s, 1H), 8.67 (s, 1H), 8.49 (d, J=8.2 Hz, 2H), 8.15-8.10 (m, 2H), 7.79 (d, J=4.2 Hz, 2H), 3.14-3.02 (m, 2H), 1.18-1.09 (m, 3H).

Example 3: Preparation of Compound 3

4-(5-hydroxy-1-(5-isobutyrylpyridin-2-yl)-1H-pyrazol-4-yl)benzonitrile

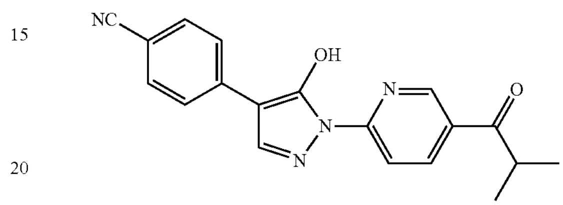

To a solution of ethylmagnesium bromide isopropylmagnesium chlorid (2.29 mL, 2.29 mmol, 1M in tetrahydrofuran) in anhydrous tetrahydrofuran (5.0 mL) was added 6-(4-(4-cyanophenyl)-5-hydroxy-1H-pyrazol-1-yl)-N-methoxy-N-methylnicotinamide (Intermediate from Example 1) (200 mg, 0.57 mmol) at −20° C. The mixture was allowed to warm up to 0° C. and left stirring for another one hour. The reaction was quenched with water and extracted twice with ethyl acetate. The organic layer was washed with brine, dried over sodium sulfate and concentrated under reduced pressure. The crude product was purified by reverse Prep-HPLC to give 4-(5-hydroxy-1-(5-isobutyrylpyridin-2-yl)-1H-pyrazol-4-yl)benzonitrile (16.5 mg, 0.05 mmol, 9.5% yield) as white solid. LCMS: m/z=333.1 $(M+H)^+$, retention time 5.10 min (Method A). $^1H$ NMR (400 MHz, DMSO-$d_6$) δ 9.01 (s, 1H), 8.54 (s, 1H), 8.40 (d, J=7.8 Hz, 1H), 8.27 (s, 1H), 8.14 (s, 1H), 8.05 (d, J=8.5 Hz, 2H), 7.63 (d, J=8.5 Hz, 2H), 3.63 (s, 1H), 1.12 (d, J=6.7 Hz, 6H).

Example 4: Preparation of Compound 4 methyl 2-(4-cyanophenyl)acetate

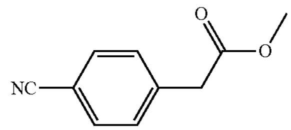

To a mixture of 2-(4-cyanophenyl)acetic acid (5.0 g, 31.0 mmol) in methanol (10.0 mL) was added hydrochloric acid in methanol (20.0 mL, 3.0 N) at 0° C. The mixture was stirred at 70° C. for 3 hr and cooled to precipitate solid. The solid was filtered, washed with methanol and dried to give methyl 2-(4-cyanophenyl)acetate (5.0 g, 28.4 mmol, 92% yield) as yellow solid. LCMS: m/z=176.0 $[M+H]^+$, retention time 1.54 min (Method A).

methyl (E)-2-(4-cyanophenyl)-3-(dimethylamino) acrylate

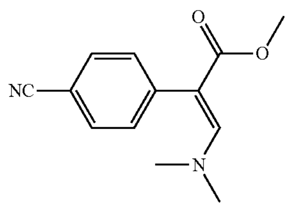 [SMILES: COC(=O)/C(=C/N(C)C)c1ccc(C#N)cc1]

To a solution of methyl 2-(4-cyanophenyl)acetate (5.0 g, 28.5 mmol) in N,N-dimethylformamide (25.0 mL) was added N,N-dimethylformamide diethyl acetal (14.0 g, 114.16 mmol). The mixture was stirred at 100° C. for 16 hr and cooled. Ethyl acetate and water were added to the solution, and the layers were separated. The organic layer was washed with brine, dried over sodium sulfate and concentrated to give methyl (E)-2-(4-cyanophenyl)-3-(dimethylamino)acrylate (5.20 g, 25.4 mmol, 89% yield) as yellow solid. LCMS: m/z=231.0 $[M+H]^+$, retention time 1.70 min (Method A). The product was pure enough and used directly to the next step.

2-bromo-5-(methylsulfonyl)pyridine

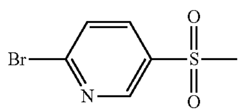

To a solution of 3,6-dibromopyridine (2.5 g, 12.7 mmol) in anhydrous tetrahydrofuran (10.0 mL) was added isopropylmagnesium chloride (8.25 mL, 16.5 mmol, 2.0 N in hexane) at 0° C. under nitrogen. The mixture was stirred at 0° C. for 45 min and then a solution of methanesulfonyl chloride (1.89 g, 16.5 mmol) in anhydrous tetrahydrofuran (5.0 mL) was added. The mixture was allowed to warm up to room temperature and left stirring for another one hour. The reaction was quenched with water and extracted twice with ethyl acetate. The organic layer was separated, washed with brine, dried over sodium sulfate and concentrated under reduced pressure. The crude product was purified by flash chromatography (petroleum ether/ethyl acetate=3/1) to obtain 2-bromo-5-(methylsulfonyl)pyridine (1.4 g, 5.98 mmol, 47.1% yield) as yellow solid. LCMS: m/z=236.0 $(M+H)^+$, retention time 1.54 min (Method A).

2-hydrazineyl-5-(methylsulfonyl)pyridine

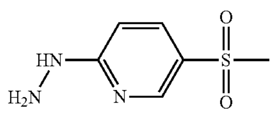

To a solution of 2-bromo-5-(methanesulfonyl)-pyridine (1.0 g, 4.25 mmol) in ethanol (10.0 mL) was added hydrazine hydrate (1.0 g, 17.0 mmol, 85% in water). The mixture was stirred at 80° C. for 4 h. The mixture was cooled and concentrated to dryness. The residue was partitioned between ethyl acetate and water. The organic phase was washed with brine, dried over sodium sulfate and concentrated. The residue was triturated with petroleum ether and filtered to afford 2-hydrazineyl-5-(methylsulfonyl)pyridine (1.2 g, 6.4 mmol, 75% yield) as white solid. LCMS: m/z=188.0 $(M+H)^+$, retention time 0.43 min (Method A).

4-(5-hydroxy-1-(5-(methylsulfonyl)pyridin-2-yl)-1H-pyrazol-4-yl)benzonitrile

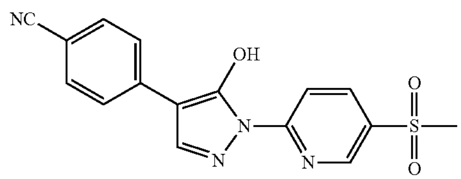 [SMILES: CS(=O)(=O)c1ccc(-n2ncc(-c3ccc(C#N)cc3)c2O)nc1]

To a solution of methyl (E)-2-(4-cyanophenyl)-3-(dimethylamino)acrylate (230 mg, 1.0 mmol) and 2-hydrazineyl-5-(methylsulfonyl)pyridine (187 mg, 1.0 mmol) in ethanol (3.0 mL) was added p-toluenesulfonic acid monohydrate (38 mg, 0.2 mmol). The mixture was stirred at reflux for 12 hr and cooled to precipitate solid. The solid was filtered, washed with ethanol and dried to give 4-(5-hydroxy-1-(5-(methylsulfonyl)pyridin-2-yl)-1H-pyrazol-4-yl)benzonitrile (58 mg, 0.17 mmol, 17.0% yield) as white solid. LCMS: m/z=341.0 $(M+H)^+$, retention time 3.93 min (Method A). $^1H$ NMR (400 MHz, DMSO-$d_6$) δ 13.68 (s, 1H), 8.93 (s, 1H), 8.68-8.76 (m, 2H), 8.49-8.51 (m, 2H), 8.15-8.17 (d, J=6.5 Hz, 2H), 7.78-7.80 (d, J=6.9 Hz, 2H), 3.35 (s, 3H).

Example 5: Preparation of Compound 5 ethyl 2-(3-cyanophenyl)acetate

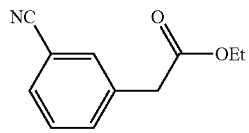 [SMILES: CCOC(=O)Cc1cccc(C#N)c1]

To a mixture of ethyl 2-(3-bromophenyl)acetate (2.5 g, 10.3 mmol) and zinc cyanide (1.20 g, 10.3 mmol) in N,N-dimethylformamide (30.0 mL) was added tetrakis(triphenylphosphine)palladium (1.16 g, 1.0 mmol). The mixture was stirred at 90° C. for 18.0 h under nitrogen and cooled to rt. The mixture was diluted with water and extracted with ethyl acetate. The organic layer was washed with brine, dried over sodium sulfate and concentrated under reduced pressure. The crude product was purified by flash chromatography (petroleum ether/ethyl acetate=9/1) to obtain ethyl 2-(3-cyanophenyl)acetate (1.72 g, 9.1 mmol, 88.3% yield) as yellow oil. LC-MS: m/z=190.0 $(M+H)^+$, retention time 1.65 min (Method A).

ethyl (E)-2-(3-cyanophenyl)-3-(dimethylamino)acrylate

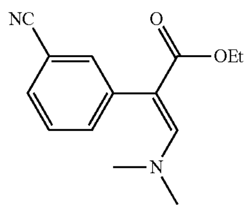 [SMILES: CCOC(=O)/C(=C/N(C)C)c1cccc(C#N)c1]

To a solution of ethyl 2-(3-cyanophenyl)acetate (1.2 g, 6.35 mmol) in N,N-dimethylformamide (8.0 mL) was added N,N-dimethylformamide diethyl acetal (4.7 g, 31.74 mmol). The mixture was stirred at 100° C. for 16.0 h and cooled. Ethyl acetate and water were added to the solution, and the layers were separated. The organic layer was washed with brine, dried over sodium sulfate and concentrated to give ethyl (E)-2-(3-cyanophenyl)-3-(dimethylamino)acrylate (1.34 g, 5.49 mmol, 86.5% yield) as yellow solid. LC-MS: m/z=245.0 $[M+H]^+$, retention time 1.50 min (Method A).

3-(5-hydroxy-1-(5-(methylsulfonyl)pyridin-2-yl)-1H-pyrazol-4-yl)benzonitrile

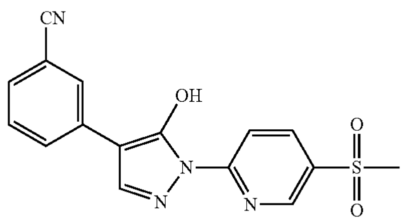 [SMILES: CS(=O)(=O)c1ccc(-n2ncc(-c3cccc(C#N)c3)c2O)nc1]

To a solution of ethyl (E)-2-(3-cyanophenyl)-3-(dimethylamino)acrylate (200 mg, 0.82 mmol) and 2-hydrazineyl-5-(methylsulfonyl)pyridine (Intermediate from Example 4) (153 mg, 0.82 mmol) in ethanol (3.0 mL) was added p-toluenesulfonic acid monohydrate (38 mg, 0.2 mmol). The mixture was stirred at 90° C. in a sealed tube for 12.0 h and cooled to precipitate solid. The solid was filtered, washed with ethanol and dried to give 3-(5-hydroxy-1-(5-(methylsulfonyl)pyridin-2-yl)-1H-pyrazol-4-yl)benzonitrile (60 mg, 0.17 mmol, 21.5% yield) as white solid. LC-MS: m/z=341.1 $(M+H)^+$, retention time 1.57 min (Method A). $^1$HNMR (400 MHz, DMSO-$d_6$) δ 13.43 (s, 1H), 8.94 (s, 1H), 8.66-8.73 (m, 2H), 8.49-8.52 (d, J=10.8 Hz, 2H), 8.41 (s, 1H), 8.30-8.31 (d, J=6.5 Hz, 1H), 7.55-7.62 (m, 2H), 3.36 (s, 3H).

Example 6: Preparation of Compound 6 ethyl 2-(4-cyano-2-methylphenyl) acetate

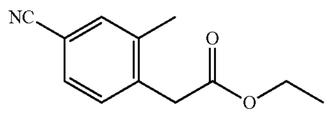

A mixture of 4-bromo-3-methylbenzonitrile (5.0 g, 25.6 mmol), diethyl malonate (27 g 168 mmol), tris(dibenzylideneacetone)dipalladium(0) (0.24 g, 0.26 mmol), tri-tert-butylphosphine tetrafluoroborate (0.08 g, 0.26 mmol), potassium carbonate (5.3 g, 38.4 mmol) and potassium hydrogen carbonate (3.84 g, 38.4 mmol) was stirred at 160° C. for 12.0 h. After cooling to room temperature, the reaction mixture was diluted with ethyl acetate and water. The organic layer was washed with brine, dried over sodium sulfate and concentrated. The residue was purified by flash chromatography (petroleum ether/ethyl acetate=1/1) to afford ethyl 2-(4-cyano-2-methylphenyl)acetate (2.0 g, 8.11 mmol, 31.7% yield) as yellow oil. LC-MS: m/z=204.1 $(M+H)^+$, retention time 1.87 min (Method A).

ethyl (E)-2-(4-cyano-2-methylphenyl)-3-(dimethylamino)acrylate

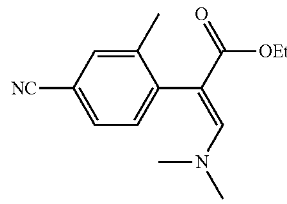 [SMILES: CCOC(=O)/C(=C/N(C)C)c1ccc(C#N)cc1C]

To a solution of ethyl 2-(4-cyano-2-methylphenyl)acetate (1.0 g, 5.0 mmol) in N,N-dimethylformamide (10.0 mL) was added N,N-dimethylformamide diethyl acetal (2.9 g, 25.0 mmol). The mixture was stirred at 100° C. overnight and cooled to room temperature. Ethyl acetate and water were added to the solution, and the layers were separated. The organic layer was washed with brine, dried over sodium sulfate and concentrated. The residue was purified by flash chromatography (dichloromethane/methanol=98/2) to give ethyl (E)-2-(4-cyano-2-methylphenyl)-3-(dimethylamino) acrylate (600 mg, 2.36 mmol, 47.2% yield) as yellow oil. LC-MS: m/z=259.0 $[M+H]^+$, retention time 1.68 min (Method B).

4-(5-hydroxy-1-(5-(methylsulfonyl)pyridin-2-yl)-1H-pyrazol-4-yl)-3-methylbenzonitrile

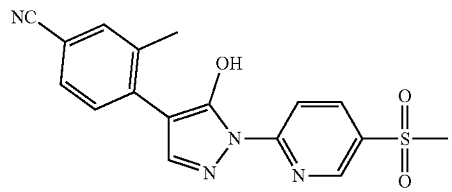 [SMILES: Cc1cc(C#N)ccc1-c1cnn(-c2ccc(S(C)(=O)=O)cn2)c1O]

To a solution of ethyl (E)-2-(4-cyano-2-methylphenyl)-3-(dimethylamino)acrylate (391 mg, 1.60 mmol) and 2-hydrazineyl-5-(methylsulfonyl)pyridine (Intermediate from Example 4) (300 mg, 1.60 mmol) in ethanol (10.0 mL) was added 4-methylbenzenesulfonic acid (34.4 mg, 0.2 mmol). The mixture was stirred at 90° C. for 12.0 h and cooled to precipitated solid. The solid was filtered, washed with ethanol and dried to give 4-(5-hydroxy-1-(5-(methylsulfonyl) pyridin-2-yl)-1H-pyrazol-4-yl)-3-methylbenzonitrile (77 mg, 0.21 mmol, 13.6% yield) as white solid. LC-MS: m/z=355.1.0 $(M+H)^+$, retention time 1.79 min (Method A).

$^1$HNMR (400 MHz, DMSO-$d_6$) δ 13.19 (s, 1H), 8.95 (s, 1H), 8.64-8.68 (m, 1H), 8.48-8.51 (d, J=8.1 Hz, 1H), 8.28 (s, 1H), 7.60-7.80 (m, 3H), 3.35 (s, 3H), 2.36 (s, 3H).

Example 7: Preparation of Compound 7 ethyl 5-hydroxy-1-(5-(methylsulfonyl)pyridin-2-yl)-1H-pyrazole-4-carboxylate

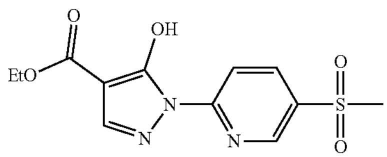 [SMILES: CCOC(=O)c1cnn(-c2ccc(S(C)(=O)=O)cn2)c1O]

A mixture of 2-hydrazineyl-5-(methylsulfonyl)pyridine (Intermediate from Example 4) (0.4 g, 2.1 mmol), diethyl 2-(ethoxymethylene)malonate (1.15 g, 5.3 mmol) and potassium carbonate (0.73 g, 5.3 mmol) in water/ethanol (30.0 mL/10.0 mL) was stirred at 60° C. overnight. Aqueous hydrochloric acid (10.0 mL, 3N) was added to the solution and a solid was precipitated. The solid was filtered, washed with water and dried to obtain ethyl 5-hydroxy-1-(5-(methylsulfonyl)pyridin-2-yl)-1H-pyrazole-4-carboxylate (0.4 g, 1.3 mmol, 61.5% yield) as yellow solid. LCMS: m/z=312.0 $(M+H)^+$, retention time 1.63 min (Method A).

ethyl 5-methoxy-1-(5-(methylsulfonyl)pyridin-2-yl)-1H-pyrazole-4-carboxylate

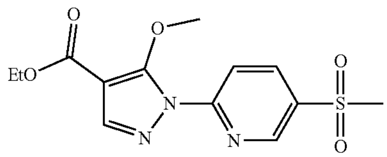 [SMILES: CCOC(=O)c1cnn(-c2ccc(S(C)(=O)=O)cn2)c1OC]

To a solution of ethyl 5-hydroxy-1-(5-(methylsulfonyl)pyridin-2-yl)-1H-pyrazole-4-carboxylate (373 mg, 1.2 mmol) in dichloromethane/methanol (10.0 mL/1.0 mL) was added (diazomethyl)trimethylsilane (1.61 mL, 3.23 mmol, 2N in hexanes). The mixture was stirred at 25° C. overnight and concentrated to give dryness. The residue was purified by flash chromatography (dichloromethane/methanol=100/2) to obtain ethyl 5-methoxy-1-(5-(methylsulfonyl)pyridin-2-yl)-1H-pyrazole-4-carboxylate (0.3 g, 0.92 mmol, 76.9% yield) as yellow solid. LCMS: m/z=326.0 $[M+H]^+$, retention time 1.75 min (Method A).

5-methoxy-1-(5-(methylsulfonyl)pyridin-2-yl)-1H-pyrazole-4-carboxylic acid

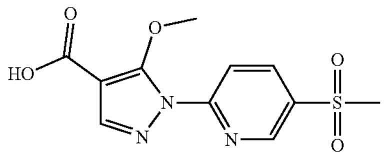 [SMILES: COc1c(C(=O)O)cnn1-c1ccc(S(C)(=O)=O)cn1]

To a solution of ethyl 5-methoxy-1-(5-(methylsulfonyl)pyridin-2-yl)-1H-pyrazole-4-carboxylate (0.3 g, 0.92 mmol) in 1,4-dioxane (10.0 mL) was added aqueous lithium hydroxide (3.0 mL, 3.0 mmol, 1.0 N) at 0° C. The mixture was allowed to warm up to room temperature and left stirring for 18 h. The solution was acidified with 1N hydrochloric acid and extracted with dichloromethane. The organic layer was separated, washed with brine, dried over sodium sulfate and concentrated under reduced pressure to give 5-methoxy-1-(5-(methylsulfonyl)pyridin-2-yl)-1H-pyrazole-4-carboxylic acid (0.2 g, 0.61 mmol, 66.8% yield) as yellow solid. LCMS: m/z=326.0 $(M+H)^+$, retention time 1.25 min (Method A).

2-(4-bromo-5-methoxy-1H-pyrazol-1-yl)-5-(methylsulfonyl)pyridine

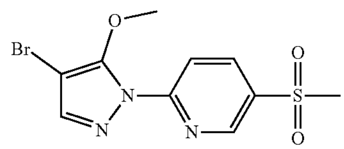 [SMILES: COc1c(Br)cnn1-c1ccc(S(C)(=O)=O)cn1]

A mixture of 5-methoxy-1-(5-(methylsulfonyl)pyridin-2-yl)-1H-pyrazole-4-carboxylic acid (0.2 g, 0.61 mmol), N-bromosuccinimide (0.18 g, 1.0 mmol) and sodium hydrogen carbonate (0.17 g, 2.0 mmol) in N,N-dimethylformamide (10.0 mL) was stirred at 25° C. for 2 h. The reaction was diluted with water and extracted with ethyl acetate. The organic layer was washed with brine, dried over sodium sulfate and concentrated under reduced pressure. The crude product was purified by flash chromatography (petroleum ether/ethyl acetate=10/1) to obtain 2-(4-bromo-5-methoxy-1H-pyrazol-1-yl)-5-(methylsulfonyl)pyridine (0.16 g, 0.47 mmol 78% yield) as yellow solid. LCMS: m/z=332.0 $(M+H)^+$, retention time 1.55 min (Method A).

2-(4-(5-methoxy-1-(5-(methylsulfonyl)pyridin-2-yl)-1H-pyrazol-4-yl)phenyl)acetonitrile

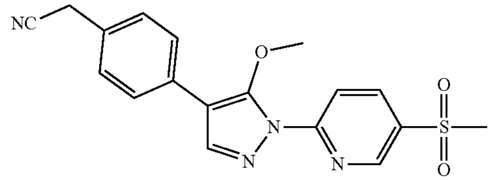 [SMILES: COc1c(-c2ccc(CC#N)cc2)cnn1-c1ccc(S(C)(=O)=O)cn1]

A mixture of 2-(4-bromo-5-methoxy-1H-pyrazol-1-yl)-5-(methylsulfonyl)pyridine (0.1 g, 0.3 mmol), 2-(4-(4,4,5,5-tetramethyl-1,3,2-dioxaborolan-2-yl)phenyl)acetonitrile (0.15 g, 0.6 mmol), sodium carbonate (64 mg, 0.60 mmol), tetrakis(triphenylphosphine)palladium (35 mg, 0.03 mmol) in 1.4-dioxane/water (10.0 mL/1.0 mL) was stirred at 110° C. overnight. The mixture was cooled and concentrated to dryness. The residue was purified by flash chromatography (petroleum ether/ethyl acetate=1/1) to afford 2-(4-(5-methoxy-1-(5-(methylsulfonyl)pyridin-2-yl)-1H-pyrazol-4-yl)phenyl)acetonitrile (0.1 g, 0.27 mmol, 90% yield) as yellow solid. LCMS: m/z=369.0 $[M+H]^+$, retention time 1.55 min (Method B).

2-(4-(5-hydroxy-1-(5-(methylsulfonyl)pyridin-2-yl)-1H-pyrazol-4-yl)phenyl)acetonitrile

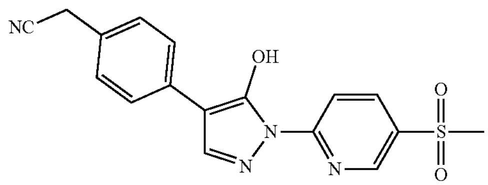 [SMILES: CS(=O)(=O)c1ccc(-n2ncc(-c3ccc(CC#N)cc3)c2O)nc1]

A mixture of 2-(4-(5-methoxy-1-(5-(methylsulfonyl)pyridin-2-yl)-1H-pyrazol-4-yl) phenyl)acetonitrile (0.1 g, 0.3 mmol) and lithium chloride (0.04 g, 0.90 mmol) in N,N-dimethylformamide (5.0 mL) was stirred at 60° C. overnight. The solution was diluted with ethyl acetate and water. The organic layer was washed with brine, dried over sodium sulfate and evaporated to dryness. The residue was purified by reverse Prep-HPLC to give 2-(4-(5-hydroxy-1-(5-(methylsulfonyl)pyridin-2-yl)-1H-pyrazol-4-yl)phenyl) acetonitrile (55 mg, 0.15 mmol, 51.8% yield) as white solid. LCMS: m/z=355.0 $(M+H)^+$, retention time 3.42 min (Method B). $^1H$ NMR (400 MHz, DMSO-$d_6$) δ 13.18 (s, 1H), 8.94 (s, 1H), 8.47-8.55 (m, 3H), 7.95-7.97 (d, J=6.5 Hz, 2H), 7.32-7.34 (d, J=6.5 Hz, 2H), 4.01 (s, 2H), 3.29 (s, 3H).

Example 8: Preparation of Compound 8 ethyl 2-(2-methoxypyridin-4-yl)acetate

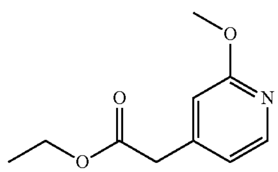

To a solution of 2-methoxy-4-methylpyridine (2.0 g, 16.2 mmol) in anhydrous tetrahydrofuran (50.0 mL) was added lithium diisopropylamide (16.0 mL, 32.0 mmol, 2.0 N in n-heptane) at −78° C. under nitrogen. The mixture was stirred at −78° C. for 10 min and diethyl carbonate (3.78 g, 32.0 mmol) was added. The mixture was allowed to warm up to room temperature and stirred for 2 h. The reaction was quenched with water and extracted twice with ethyl acetate. The organic layer was washed with brine, dried over sodium sulfate and concentrated under reduced pressure. The crude product was purified by flash chromatography (petroleum ether/ethyl acetate=10/1) to obtain ethyl 2-(4-cyano-2-methylphenyl)-3-oxobutanoate (2.0 g, 10.2 mmol, 63.4% yield) as yellow oil. LCMS: m/z=196.1 $(M+H)^+$, retention time 1.97 min (Method A).

ethyl (E)-3-(dimethylamino)-2-(2-methoxypyridin-4-yl)acrylate

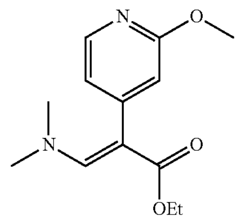

To a solution of ethyl 2-(2-methoxypyridin-4-yl)acetate (1.95 g, 10 mmol) in N,N-dimethylformamide (3.0 mL) was added N,N-dimethylformamide diethyl acetal (5.95 g, 50 mmol). The mixture was stirred at 100° C. for 12 hr and cooled. Ethyl acetate and water were added to the solution, and the layers were separated. The organic layer was washed with brine, dried over sodium sulfate and concentrated under reduced pressure. The crude product was purified by flash chromatography (dichloromethane/methanol=98/2) to obtain ethyl (E)-3-(dimethylamino)-2-(2-methoxypyridin-4-yl)acrylate (1.1 g, 4.4 mmol, 44% yield) as colorless oil. LCMS: m/z=251.0 $[M+H]^+$, retention time 1.68 min (Method B).

4-(2-methoxypyridin-4-yl)-1-(5-(methylsulfonyl)pyridin-2-yl)-1H-pyrazol-5-ol

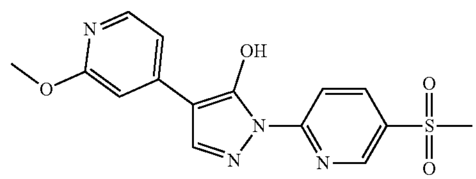

To a solution of ethyl (E)-3-(dimethylamino)-2-(2-methoxypyridin-4-yl)acrylate (0.25 g, 1.0 mmol) and 2-hydrazineyl-5-(methylsulfonyl)pyridine (Intermediate from Example 4) (0.2 g, 1.0 mmol) in ethanol (3.0 mL) was added p-toluenesulfonic acid monohydrate (0.19 g, 1.0 mmol). The mixture was stirred at reflux for 12 hr and cooled to precipitate solid. The solid was filtered, washed with ethanol and dried to give 4-(2-methoxypyridin-4-yl)-1-(5-(methylsulfonyl)pyridin-2-yl)-1H-pyrazol-5-ol (90 mg, 0.26 mmol, 26% yield) as white solid. LCMS: m/z=347.0 $(M+H)^+$, retention time 2.28 min (Method A). $^1H$ NMR (400 MHz, DMSO-$d_6$) δ 8.94-8.97 (d, J=8.5 Hz, 2H), 8.67-8.70 (d, J=8.5 Hz, 1H), 8.49-8.52 (d, J=7.5 Hz, 1H), 8.18-8.19 (d, J=7.6 Hz, 1H), 7.77-7.83 (m, 2H), 4.03 (s, 3H), 3.36 (s, 3H).

Example 9: Preparation of Compound 9 ethyl (E)-2-(4-bromophenyl)-3-(dimethylamino) acrylate

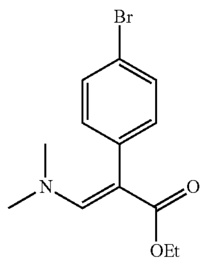 [SMILES: CCOC(=O)/C(=C/N(C)C)c1ccc(Br)cc1]

To a solution of ethyl 2-(4-bromophenyl)acetate (1.5 g, 6.2 mmol) in N,N-dimethylformamide (3.0 mL) was added N,N-dimethylformamide diethyl acetal (3.7 g, 31 mmol). The mixture was stirred at 100° C. for 12 hr and cooled. Ethyl acetate and water were added to the solution, and the layers were separated. The organic layer was washed with brine, dried over sodium sulfate and concentrated to give (E)-2-(4-bromophenyl)-3-(dimethylamino)acrylate (1.1 g, 3.7 mmol, 59.5% yield) as yellow oil. LCMS: m/z=298.0 $[M+H]^+$, retention time 2.08 min (Method A). The product was pure enough and used directly to the next step 4-(4-bromophenyl)-1-(5-(methylsulfonyl)pyridin-2-yl)-1H-pyrazol-5-ol

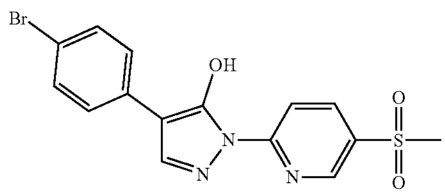 [SMILES: CS(=O)(=O)c1ccc(-n2ncc(-c3ccc(Br)cc3)c2O)nc1]

To a solution of ethyl (E)-2-(4-bromophenyl)-3-(dimethylamino)acrylate (0.5 g, 1.7 mmol) and 2-hydrazineyl-5-(methylsulfonyl)pyridine (Intermediate from Example 4) (0.31 g, 1.7 mmol) in ethanol (10.0 mL) was added p-toluenesulfonic acid monohydrate (64 mg, 0.34 mmol). The mixture was stirred at reflux for 12 hr and cooled to precipitate solid. The solid was filtered, washed with ethanol and dried to give 4-(4-bromophenyl)-1-(5-(methylsulfonyl) pyridin-2-yl)-1H-pyrazol-5-ol (0.3 g, 0.76 mmol, 44.9% yield) as white solid. LCMS: m/z=394.0 $(M+H)^+$, retention time 1.88 min (Method A). $^1H$ NMR (400 MHz, DMSO-$d_6$) δ 13.28 (s, 1H), 8.93 (s, 1H), 8.50-8.53 (m, 3H), 7.91-7.93 (d, J=8.5 Hz, 2H), 7.53-7.55 (d, J=8.9 Hz, 2H), 3.35 (s, 3H).

Example 10: Preparation of Compound 10

2-bromo-5-(1H-pyrazol-1-yl)pyridine

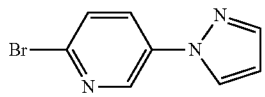 [SMILES: Brc1ccc(-n2cccn2)cn1]

A mixture of 2-bromo-5-iodopyridine (1.00 g, 3.52 mmol), 1H-pyrazole (239.8 mg, 3.52 mmol), cuprous iodide (67.09 mg, 0.35 mmol), potassium phosphate (1.87 g, 8.81 mmol) and (1R,2R)-cyclohexane-1,2-diamine (45.6 mg, 0.4 mmol) in 1,4-dioxane (10.0 mL) was stirred at room temperature for 12 h. The reaction solution was diluted with ethyl acetate and water. The organic layer was washed with brine, dried over sodium sulfate and concentrated. The residue was purified by flash chromatography (petroleum ether/ethyl acetate=6/1) to afford 2-bromo-5-(1H-pyrazol-1-yl)pyridine (220 mg, 2.85 mmol, 81.12% yield) as yellow oil. LCMS: m/z=224.1 $(M+H)^+$, retention time 1.55 min (Method A).

2-hydrazineyl-5-(1H-pyrazol-1-yl)pyridine

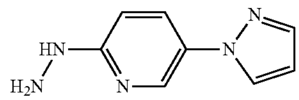

To a solution of 2-bromo-5-(1H-pyrazol-1-yl)pyridine (200 mg, 0.89 mmol) in ethanol (2.0 mL) was added hydrazine hydrate (223.2 mg, 4.46 mmol, 85% in water). The mixture was stirred at 100° C. for 2 hr in a sealed tube. The mixture was cooled and concentrated to dryness. The residue was partitioned between ethyl acetate and water. The organic layer was separated, washed with brine, dried over sodium sulfate and concentrated. The residue was triturated with petroleum ether and filtered to afford 2-hydrazineyl-5-(1H-pyrazol-1-yl)pyridine (140 mg, 0.80 mmol, 90.32% yield) as yellow solid. LCMS: m/z=176.1 $(M+H)^+$, retention time 1.01 min (Method B).

4-(1-(5-(1H-pyrazol-1-yl)pyridin-2-yl)-5-hydroxy-TH-pyrazol-4-yl)benzonitrile

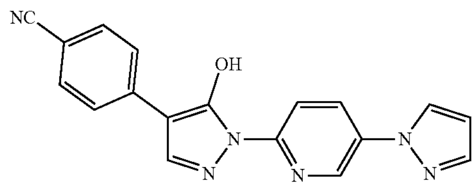 [SMILES: N#Cc1ccc(-c2cnn(-c3ccc(-n4cccn4)cn3)c2O)cc1]

To a solution of methyl (E)-2-(4-cyanophenyl)-3-(dimethylamino)acrylate (210.29 mg, 0.91 mmol) and 2-hydrazineyl-5-(1H-pyrazol-1-yl)pyridine (160.00 mg, 0.91 mmol) in ethanol (5.0 mL) was added p-toluenesulfonic acid monohydrate (34 mg, 0.18 mmol). The mixture was stirred at reflux for 12 hr and cooled to precipitate solid. The solid was filtered, washed with ethanol and dried to give 4-(1-(5-(1H-pyrazol-1-yl)pyridin-2-yl)-5-hydroxy-1H-pyrazol-4-yl)benzonitrile (74 mg, 0.22 mmol, 24.8% yield) as white solid. LCMS: m/z=329.1 $(M+H)^+$, retention time 4.50 min (Method A). $^1H$ NMR (400 MHz, DMSO-$d_6$) δ 13.44 (s, 1H), 8.99 (t, J=1.2 Hz, 1H), 8.62 (d, J=6.6 Hz, 2H), 8.50-8.48 (m, 2H), 8.16 (d, J=4.0 Hz, 2H), 7.85-7.79 (m, 3H), 6.64 (t, J=2.0 Hz, 1H).

Example 11: Preparation of Compound 11

2-(6-chloropyridin-3-yl)oxazole

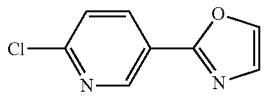

To a solution of 2-chloro-5-iodopyridine (1.5 g, 6.26 mmol) in anhydrous tetrahydrofuran (5.0 mL) was added n-butyllithium (4.26 mL, 10.65 mmol, 2.5 N in hexane) at −78° C. under nitrogen. The mixture was stirred at −78° C. for 30 min and then zinc chloride (18.79 mg, 18.79 mmol, 1.0 N in dichloromethane) was added. The mixture was allowed to warm up to room temperature and a solution of tetrakis(triphenylphosphine)palladium (361.78 mg, 0.31 mmol) and oxazole (605.65 mg, 8.77 mmol) in anhydrous tetrahydrofuran (10.0 mL) was added. The mixture was stirred at 60° C. for 4 hr and concentrated. The residue was partitioned between ethyl acetate and water. The organic layer was washed with brine, dried over sodium sulfate and concentrated under reduced pressure. The crude product was purified by flash chromatography (petroleum ether/ethyl acetate=5/1) to give 2-(6-chloropyridin-3-yl)oxazole (900 mg, 4.94 mmol, 79.93% yield) as white solid. LCMS: m/z=181.1 $(M+H)^+$, retention time 1.51 min (Method A).

2-(6-hydrazineylpyridin-3-yl)oxazole

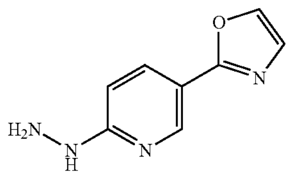 [SMILES: NNc1ccc(-c2ncco2)cn1]

To a solution of 2-(6-chloropyridin-3-yl)oxazole (700 mg, 3.13 mmol) in ethanol (5.0 mL) was added hydrazine hydrate (781.25 mg, 15.63 mmol, 85% in water). The mixture was stirred at 100° C. for 2 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford 2-(6-hydrazineylpyridin-3-yl) oxazole (400 mg, 2.25 mmol, 72.72% yield) as yellow solid. LCMS: m/z=176.1 $(M+H)^+$, retention time 0.99 min (Method B).

4-(5-hydroxy-1-(5-(oxazol-2-yl)pyridin-2-yl)-1H-pyrazol-4-yl)benzonitrile

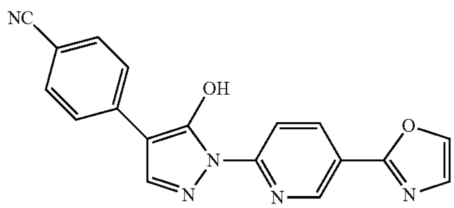 [SMILES: N#Cc1ccc(-c2cnn(-c3ccc(-c4ncco4)cn3)c2O)cc1]

To a solution of methyl (E)-2-(4-cyanophenyl)-3-(dimethylamino)acrylate (328.57 mg, 1.43 mmol) and 2-(6-hydrazineylpyridin-3-yl)oxazole (250.00 mg, 1.43 mmol) in ethanol (5.0 mL) was added p-toluenesulfonic acid monohydrate (55 mg, 0.29 mmol). The mixture was stirred at reflux for 12 hr and cooled to precipitate solid. The solid was filtered, washed with ethanol and dried to give 4-(5-hydroxy-1-(5-(oxazol-2-yl)pyridin-2-yl)-1H-pyrazol-4-yl) benzonitrile (150 mg, 0.46 mmol, 31.91% yield) as white solid. LCMS: m/z=330.0 $(M+H)^+$, retention time 1.74 min (Method B). $^1H$ NMR (400 MHz, DMSO-$d_6$) δ 13.54 (s, 1H), 9.04 (s, 1H), 8.64 (s, 1H), 8.61-8.46 (m, 2H), 8.32 (d, J=0.7 Hz, 1H), 8.14 (d, J=8.4 Hz, 2H), 7.78 (d, J=8.6 Hz, 2H), 7.46 (d, J=0.7 Hz, 1H).

Example 12: Preparation of Compound 12

2-(6-chloropyridin-3-yl)thiazole

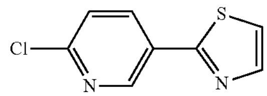 [SMILES: Clc1ccc(-c2nccs2)cn1]

To a solution of 5-bromo-2-chloropyridine (500.0 mg, 2.60 mmol) and 2-(tributylstannyl) thiazole (1458.2 mg, 3.90 mmol) in N,N-dimethylformamide (10.0 mL) was added bis(triphenylphosphine)palladium(II) dichloride (182.37 mg, 0.26 mmol). The reaction was stirred at 100° C. for 3 hr in a sealed tube. The mixture was cooled to room temperature and concentrated to dryness. The residue was purified by flash chromatography (petroleum ether/ethyl acetate=20/1) to give 2-(6-chloropyridin-3-yl)thiazole (350 mg, 1.77 mmol, 68% yield). LCMS: m/z=197.0 $[M+H]^+$, retention time 1.719 min (Method A).

2-(6-hydrazineylpyridin-3-yl)thiazole

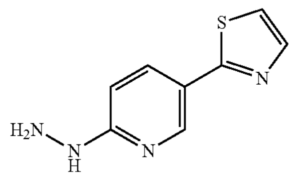

A mixture of 2-(6-chloropyridin-3-yl)thiazole (300.0 mg, 1.53 mmol) in ethanol (3.0 mL) and hydrazine hydrate (3.0 mL, 85% in water) was stirred at 110° C. for 3 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford 2-(6-hydrazineylpyridin-3-yl)thiazole (185 mg, 0.96 mmol, 63% yield). LCMS: m/z=193.0 $[M+H]^+$, retention time 1.120 min (Method B). The product was pure enough and used directly to the next step.

4-(5-hydroxy-1-(5-(thiazol-2-yl)pyridin-2-yl)-1H-pyrazol-4-yl)benzonitrile

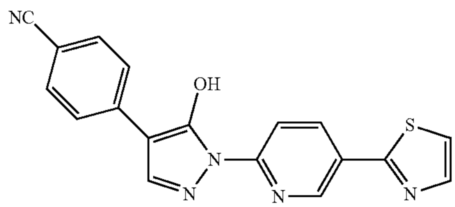 [SMILES: N#Cc1ccc(-c2cnn(-c3ccc(-c4nccs4)cn3)c2O)cc1]

To a solution of methyl (E)-2-(4-cyanophenyl)-3-(dimethylamino)acrylate (200.0 mg, 0.87 mmol) in ethanol (8 mL) was added 2-(6-hydrazineylpyridin-3-yl)thiazole (166.97 mg, 0.87 mmol) and p-toluenesulfonic acid monohydrate (17 mg, 0.09 mmol). The reaction was stirred at 90° C. for 16 hr and cooled to precipitate solid. The solid was filtered, washed with ethanol and dried to give 4-(5-hydroxy-1-(5-(thiazol-2-yl)pyridin-2-yl)-1H-pyrazol-4-yl) benzonitrile (80 mg, 0.23 mmol, 27% yield) as yellow solid. LCMS: m/z=346.0 $[M+H]^+$, retention time 1.893 min (Method B). $^1H$ NMR (400 MHz, DMSO-$d_6$) δ 13.51 (br, 1H), 9.05 (s, 1H), 8.65 (s, 1H), 8.53 (s, 2H), 8.14 (d, J=7.5 Hz, 2H), 8.01 (d, J=2.5 Hz, 1H), 7.90 (d, J=3.0 Hz, 1H), 7.79 (d, J=8.0 Hz, 2H).

Example 13: Preparation of Compound 13

6'-chloro-2,3'-bipyridine

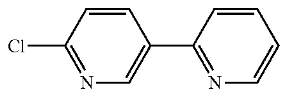 [SMILES: Clc1ccc(-c2ccccn2)cn1]

A mixture of 2-bromopyridine (390 mg, 2.5 mmol), (6-chloropyridin-3-yl)boronic acid (470 mg 3.0 mmol), potassium carbonate (828 mg, 6.0 mmol), palladium (II) acetate (56 mg, 0.6 mmol) in 1,2-dimethoxyethane/water (10.0 mL/2.0 mL) was stirred at 90° C. overnight. The mixture was cooled and concentrated to dryness. The residue was purified by flash chromatography (petroleum ether/ethyl acetate=3/1) to afford 6'-chloro-2,3'-bipyridine (380 mg, 2.0 mmol, 80% yield) as yellow solid. LCMS: m/z=191.0 $[M+H]^+$, retention time=2.20 min (Method A).

6'-hydrazineyl-2,3'-bipyridine

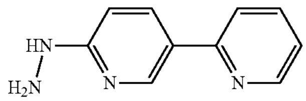 [SMILES: NNc1ccc(-c2ccccn2)cn1]

To a solution of 6'-chloro-2,3'-bipyridine (380 mg, 2.0 mmol) in ethanol (10.0 mL) was added hydrazine hydrate (5.0 mL, 85% in water). The mixture was stirred at 120° C. overnight in a sealed tube. The mixture was cooled and concentrated to dryness. The residue was partitioned between ethyl acetate and water. The organic layer was washed with brine, dried over sodium sulfate and concentrated to give 6'-hydrazineyl-2,3'-bipyridine (200 mg, 1.07 mmol, 54% yield) as yellow oil. LCMS: m/z=187.1 $[M+H]^+$, retention time 0.54 min (Method A). The product was used directly to the next step.

4-(1-([2,3'-bipyridin]-6'-yl)-5-hydroxy-1H-pyrazol-4-yl)benzonitrile

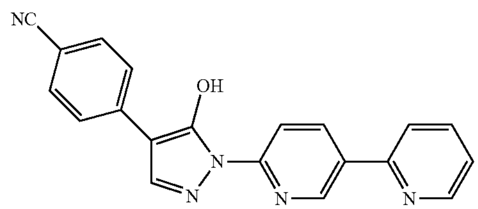 [SMILES: N#Cc1ccc(-c2cnn(-c3ccc(-c4ccccn4)cn3)c2O)cc1]

To a solution of methyl (E)-2-(4-cyanophenyl)-3-(dimethylamino)acrylate (240 mg, 1.07 mmol) and 6'-hydrazineyl-2,3'-bipyridine (200 mg, 1.07 mmol) in ethanol (4.0 mL) was added p-toluenesulfonic acid monohydrate (38.2 mg, 0.20 mmol). The mixture was stirred at reflux for 12 hr and cooled to precipitate solid. The solid was filtered, washed with ethanol and dried to afford 4-(1-([2,3'-bipyridin]-6'-yl)-5-hydroxy-TH-pyrazol-4-yl)benzonitrile (35 mg, 0.10 mmol, 9.64% yield) as white solid. LCMS: m/z=340.2 $(M+H)^+$, retention time 4.71 min (Method A). $^1H$ NMR (500 MHz, DMSO-$d_6$) δ 9.19 (s, 1H), 8.81-8.66 (m, 2H), 8.60 (s, 1H), 8.49 (s, 1H), 8.12 (dd, J=17.7, 7.9 Hz, 3H), 7.96 (t, J=7.6 Hz, 1H), 7.79 (d, J=8.3 Hz, 2H), 7.49-7.38 (m, 1H).

Example 14: Preparation of Compound 14

4-(5-hydroxy-1-(5-(trifluoromethyl)pyridin-2-yl)-1H-pyrazol-4-yl)benzonitrile

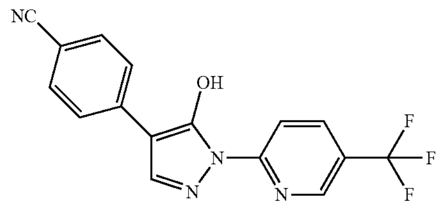 [SMILES: N#Cc1ccc(-c2cnn(-c3ccc(C(F)(F)F)cn3)c2O)cc1]

To a solution of methyl (E)-2-(4-cyanophenyl)-3-(dimethylamino)acrylate (130 mg, 0.56 mmol) and 2-hydrazineyl-5-(trifluoromethyl)pyridine (100 mg, 0.56 mmol) in ethanol (4.0 mL) was added p-toluenesulfonic acid monohydrate (21 mg, 0.11 mmol). The mixture was stirred at reflux for 12 hr and cooled to precipitate solid. The solid was filtered, washed with ethanol and dried to 4-(5-hydroxy-1-(5-(trifluoromethyl)pyridin-2-yl)-1H-pyrazol-4-yl)benzonitrile (70.8 mg, 0.21 mmol, 38% yield) as white solid. LCMS: m/z=331.0 $(M+H)^+$, retention time 5.08 min (Method A). $^1H$ NMR (400 MHz, DMSO-$d_6$) δ 13.54 (s, 1H), 8.86 (s, 1H), 8.73 (s, 1H), 8.65 (d, J=8.6 Hz, 1H), 8.41 (dd, J=8.9, 2.1 Hz, 1H), 8.15 (d, J=8.3 Hz, 2H), 7.78 (d, J=8.4 Hz, 2H).

Example 15: Preparation of Compound 15

1-(6-bromopyridin-3-yl)pyrrolidin-2-one

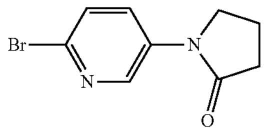 [SMILES: O=C1CCCN1c1ccc(Br)nc1]

A mixture of 2-bromo-5-iodopyridine (2.0 g, 7.04 mmol), potassium phosphate (4.5 g, 21.13 mmol), cuprous iodide (134 mg, 0.70 mmol), pyrrolidin-2-one (1.2 g, 14.09 mmol) and ethylene glycol (44 mg, 0.70 mmol) in isopropyl alcohol (20.0 mL) was stirred at 110° C. for 12 hr in a sealed tube. The mixture was cooled to room temperature and concentrated to dryness. The residue was purified by flash chromatography (petroleum ether/ethyl acetate=1/1) to afford 1-(6-bromopyridin-3-yl)pyrrolidin-2-one (0.8 g, 9.93 mmol, 47% yield) as white solid. LCMS: m/z=241.1 $[M+H]^+$, retention time=1.67 min (Method A).

1-(6-hydrazineylpyridin-3-yl)pyrrolidin-2-one

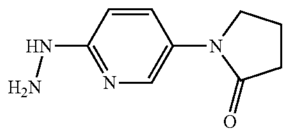 [SMILES: NNc1ccc(N2CCCC2=O)cn1]

To a solution of 1-(6-bromopyridin-3-yl)pyrrolidin-2-one (400 mg, 1.66 mmol) in ethanol (4.0 mL) was added hydrazine hydrate (2.0 mL, 85% in water). The mixture was stirred at 130° C. for 18 hr in a sealed tube. The mixture was cooled and concentrated to dryness. The residue was purified by flash chromatography (petroleum ether/ethyl acetate=1/1) to afford 1-(6-hydrazineylpyridin-3-yl)pyrrolidin-2-one (160 mg, 0.83 mmol, 50% yield) as yellow oil. LCMS: m/z=193.2 $[M+H]^+$, retention time=0.69 min (Method B).

4-(5-hydroxy-1-(5-(2-oxopyrrolidin-1-yl)pyridin-2-yl)-1H-pyrazol-4-yl)benzo-nitrile

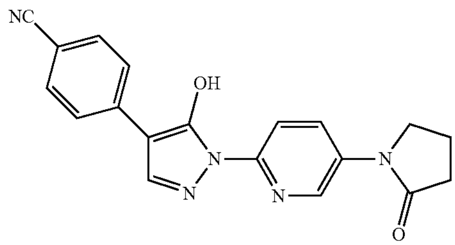 [SMILES: N#Cc1ccc(-c2cnn(-c3ccc(N4CCCC4=O)cn3)c2O)cc1]

To a solution of methyl (E)-2-(4-cyanophenyl)-3-(dimethylamino)acrylate (120 mg, 0.52 mmol) and 1-(6-hydrazineylpyridin-3-yl)pyrrolidin-2-one (100 mg, 0.52 mmol) in ethanol (4.0 mL) was added p-toluenesulfonic acid monohydrate (19 mg, 0.10 mmol). The mixture was stirred at reflux for 12 hr and cooled to precipitate solid. The solid was purified by reverse phase Prep-HPLC to give 4-(5-hydroxy-1-(5-(2-oxopyrrolidin-1-yl)pyridin-2-yl)-1H-pyrazol-4-yl)benzonitrile (9.0 mg, 0.03 mmol, 5.0% yield) as white solid. LCMS: m/z=346.4 $(M+H)^+$, retention time 4.08 min (Method A). $^1$H NMR (400 MHz, DMSO-$d_6$) δ 13.38 (s, 1H), 8.99-8.70 (m, 1H), 8.70-8.41 (m, 1H), 8.31 (d, 2H), 8.11 (d, J=7.2 Hz, 2H), 7.79 (d, J=8.5 Hz, 2H), 3.90 (t, J=7.0 Hz, 2H), 2.56-2.51 (m, 2H), 2.20-2.03 (m, 2H).

Example 16: Preparation of Compound 16

5-cyclopropyl-2-fluoropyridine

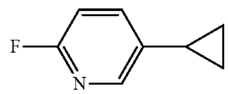

A mixture of 5-bromo-2-fluoropyridine (435 mg, 2.5 mmol), cyclopropylboronic acid (260 mg, 3.0 mmol), potassium phosphate (1.27 g, 6.0 mmol), palladium (II) acetate (56 mg, 0.6 mmol) and tricyclohexyl phosphine (340 mg, 1.2 mmol) in 1,2-dimethoxyethane/water (10.0 mL/2.0 mL) was stirred at 80° C. overnight. The mixture was cooled and concentrated to dryness. The residue was purified by flash chromatography (petroleum ether/ethyl acetate=3/1) to afford 5-cyclopropyl-2-fluoropyridine (246 mg, 1.8 mmol, 72% yield) as yellow solid. LCMS: m/z=138.1 $[M+H]^+$, retention time=2.25 min (Method A).

5-cyclopropyl-2-hydrazineylpyridine

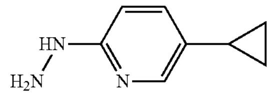

To a solution of 5-cyclopropyl-2-fluoropyridine (246 mg, 1.8 mmol) in ethanol (10.0 mL) was added hydrazine hydrate (5.0 mL, 85% in water). The mixture was stirred at 120° C. overnight in a sealed tube. The mixture was cooled and concentrated to dryness. The residue was partitioned between ethyl acetate and water. The organic layer was washed with brine, dried over sodium sulfate and concentrated to give 5-cyclopropyl-2-hydrazineylpyridine (150 mg, 1.00 mmol, 55% yield) as yellow oil. LCMS: m/z=150.1 $[M+H]^+$, retention time 0.50 min (Method A). The product was used directly to the next step.

4-(1-(5-cyclopropylpyridin-2-yl)-5-hydroxy-1H-pyrazol-4-yl)benzonitrile

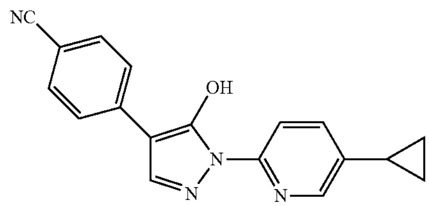 [SMILES: N#Cc1ccc(-c2cnn(-c3ccc(C4CC4)cn3)c2O)cc1]

To a solution of methyl (E)-2-(4-cyanophenyl)-3-(dimethylamino)acrylate (230 mg, 1.00 mmol) and 5-cyclopropyl-2-hydrazineylpyridine (150 mg, 1.00 mmol) in ethanol (4.0 mL) was added p-toluenesulfonic acid monohydrate (38.0 mg, 0.20 mmol). The mixture was stirred at reflux for 12 hr and cooled to precipitate solid. The solid was filtered, washed with ethanol and dried to afford 4-(1-(5-cyclopropylpyridin-2-yl)-5-hydroxy-1H-pyrazol-4-yl)benzonitrile (36 mg, 0.12 mmol, 12% yield) as white solid. LCMS: m/z=303.3 $(M+H)^+$, retention time 5.189 min (Method A). $^1H$ NMR (400 MHz, DMSO-$d_6$) δ 8.30 (s, 1H), 8.15 (s, 1H), 8.14-8.07 (m, 1H), 8.02 (d, J=7.5 Hz, 2H), 7.67-7.53 (m, 3H), 1.96-1.82 (m, 1H), 0.95 (d, J=7.0 Hz, 2H), 0.67 (d, J=7.0 Hz, 2H).

Example 17: Preparation of Compound 17

5-fluoro-2-hydrazineylpyridine

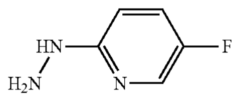

To a solution of 2,5-difluoropyridine (500 mg, 4.34 mmol) in ethanol (2.0 mL) was added hydrazine hydrate (434 mg, 8.69 mmol, 85% in water). The mixture was stirred at 120° C. overnight in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford 5-fluoro-2-hydrazineylpyridine (270 mg, 2.13 mmol, 49% yield) as white solid. LCMS: m/z=128.1 $(M+H)^+$, retention time 0.33 min (Method A).

4-(1-(5-fluoropyridin-2-yl)-5-hydroxy-1H-pyrazol-4-yl)benzonitrile

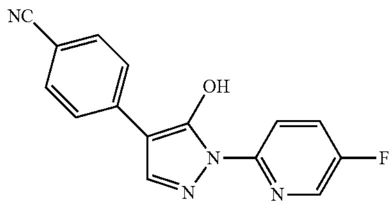 [SMILES: N#Cc1ccc(-c2cnn(-c3ccc(F)cn3)c2O)cc1]

To a solution of methyl (E)-2-(4-cyanophenyl)-3-(dimethylamino)acrylate (181 mg, 0.79 mmol) and 5-fluoro-2-hydrazineylpyridine (100 mg, 0.79 mmol) in ethanol (4.0 mL) was added p-toluenesulfonic acid monohydrate (30.4 mg, 0.16 mmol). The mixture was stirred at reflux for 12 hr and cooled to precipitate solid. The solid was filtered, washed with ethanol and dried to give 4-(1-(5-fluoropyridin-2-yl)-5-hydroxy-1H-pyrazol-4-yl)benzonitrile (94.6 mg, 0.34 mmol, 43% yield) as white solid. LCMS: m/z=281.3 $(M+H)^+$, retention time 4.38 min (Method A). $^1H$ NMR (400 MHz, DMSO-$d_6$) δ 13.30 (s, 1H), 8.61 (s, 1H), 8.52 (d, J=2.7 Hz, 1H), 8.46 (m, 1H), 8.14 (d, J=8.1 Hz, 2H), 8.00 (td, J=8.8, 2.9 Hz, 1H), 7.78 (d, J=8.4 Hz, 2H).

Example 18: Preparation of Compound 18

4-(1-(5-chloropyridin-2-yl)-5-hydroxy-1H-pyrazol-4-yl)benzonitrile

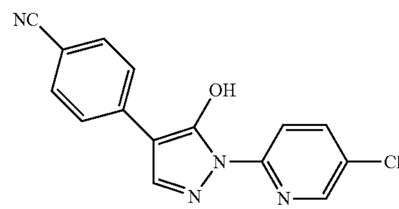 [SMILES: N#Cc1ccc(-c2cnn(-c3ccc(Cl)cn3)c2O)cc1]

To a solution of methyl (E)-2-(4-cyanophenyl)-3-(dimethylamino)acrylate (150.0 mg, 0.65 mmol) in ethanol (3.0 mL) was added 5-chloro-2-hydrazineylpyridine (93.52 mg, 0.65 mmol) and p-toluenesulfonic acid monohydrate (13.3 mg, 0.07 mmol). The reaction was stirred at 90° C. for 16 hr in a sealed tube. The reaction was cooled and concentrated to dryness. The residue was purified by flash chromatography (dichloromethane/ethyl acetate=100/1) to give 4-(1-(5-chloropyridin-2-yl)-5-hydroxy-1H-pyrazol-4-yl)benzonitrile (77 mg, 0.26 mmol, 40% yield) as yellow solid. LCMS: m/z=297.0 $[M+H]^+$, retention time 5.095 min (Method A). $^1H$ NMR (500 MHz, DMSO-$d_6$) δ 13.35 (s, 1H), 8.65 (s, 1H), 8.55 (d, J=2.5 Hz, 1H), 8.46 (s, 1H), 8.16-8.12 (m, 3H), 7.78 (d, J=6.8 Hz, 2H).

Example 19: Preparation of Compound 19

4-(4-chlorophenyl)-1-(5-(methylsulfonyl)pyridin-2-yl)-1H-pyrazol-5-ol

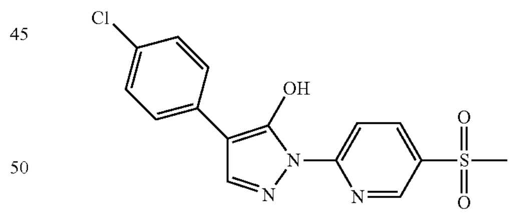

To a solution of ethyl (E)-3-(dimethylamino)-2-(4-chlorophenyl)acrylate (200 mg, 0.79 mmol) and 2-hydrazineyl-5-(methylsulfonyl)pyridine (Intermediate from Example 4) (147.83 mg, 0.79 mmol) in ethanol (5.0 mL) was added p-toluenesulfonic acid monohydrate (30.4 mg, 0.16 mmol). The mixture was stirred at reflux for 12 hr and cooled to precipitate solid. The solid was filtered, washed with ethanol and dried to give 4-(4-chlorophenyl)-1-(5-(methylsulfonyl)pyridin-2-yl)-1H-pyrazol-5-ol (95.00 mg, 0.27 mmol, 34.54% yield) as white solid. LCMS: m/z=350.1 $(M+H)^+$, retention time 1.93 min (Method A). $^1H$ NMR (400 MHz, DMSO-$d_6$) δ 8.94 (d, J=2.8 Hz, 1H), 8.81-8.56 (m, 2H), 8.49 (dd, J=8.9, 2.4 Hz, 1H), 7.98 (d, J=8.1 Hz, 2H), 7.42 (d, J=8.6 Hz, 2H), 3.38 (s, 3H).

Example 20: Preparation of Compound 20

4-(4-fluorophenyl)-1-(5-(methylsulfonyl)pyridin-2-yl)-1H-pyrazol-5-ol

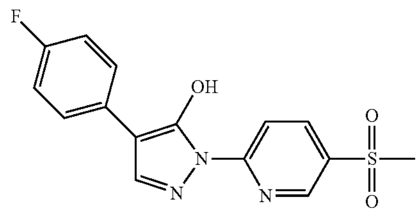 [SMILES: CS(=O)(=O)c1ccc(-n2ncc(-c3ccc(F)cc3)c2O)nc1]

To a solution of ethyl (E)-3-(dimethylamino)-2-(4-fluorophenyl)acrylate (127 mg, 0.53 mmol) and 2-hydrazineyl-5-(methylsulfonyl)pyridine (Intermediate from Example 4) (100 mg, 0.53 mmol) in ethanol (5.0 mL) was added p-toluenesulfonic acid monohydrate (20.9 mg, 0.11 mmol). The mixture was stirred at reflux for 12 hr and cooled to precipitate solid. The solid was filtered, washed with ethanol and dried to give 4-(4-fluorophenyl)-1-(5-(methylsulfonyl)pyridin-2-yl)-1H-pyrazol-5-ol (93.8 mg, 52% yield) as white solid. LCMS: m/z=334.3 $(M+H)^+$, retention time 4.02 min (Method A). $^1$H NMR (400 MHz, DMSO-$d_6$) δ 13.01 (s, 1H), 8.93 (d, J=2.1 Hz, 1H), 8.67 (m, 1H), 8.58-8.37 (m, 2H), 7.98 (dd, J=8.3, 5.7 Hz, 2H), 7.20 (t, J=8.9 Hz, 2H), 3.35 (s, 3H)

Example 21: Preparation of Compound 21

4-(1-(5-bromopyridin-2-yl)-5-hydroxy-1H-pyrazol-4-yl)benzonitrile

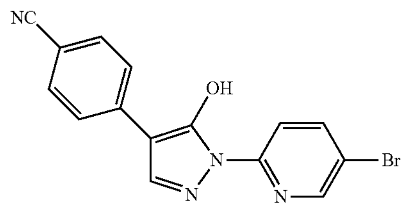 [SMILES: N#Cc1ccc(-c2cnn(-c3ccc(Br)cn3)c2O)cc1]

To a solution of methyl (E)-2-(4-cyanophenyl)-3-(dimethylamino)acrylate (612 mg, 2.66 mmol) and 5-bromo-2-hydrazineylpyridine (500 mg, 2.66 mmol) in ethanol (10.0 mL) was added p-toluenesulfonic acid monohydrate (51 mg, 0.27 mmol). The mixture was stirred at reflux for 12 hr and cooled to precipitate solid. The solid was filtered, washed with ethanol and dried to give 4-(1-(5-bromopyridin-2-yl)-5-hydroxy-1H-pyrazol-4-yl)benzonitrile (680 mg, 1.99 mmol, 75% yield) as white solid. LCMS: m/z=340.9 $(M+H)^+$, retention time 4.99 min (Method A). $^1$H NMR (500 MHz, DMSO-$d_6$) δ 13.35 (s, 1H), 8.69-8.58 (m, 2H), 8.41 (s, 1H), 8.25 (dd, J=8.9, 2.3 Hz, 1H), 8.14 (d, J=8.2 Hz, 2H), 7.78 (d, J=8.4 Hz, 2H).

Example 22: Preparation of Compound 22

N-(6-fluoropyridin-3-yl)cyclopropanecarboxamide

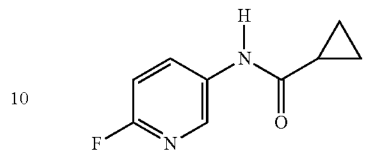

To a solution of 6-fluoropyridin-3-amine (500.0 mg, 4.46 mmol) in dichloromethane (20.0 mL) were added cyclopropanecarbonyl chloride (559.4 mg, 5.35 mmol, 0.48 mL) and triethylamine (902.6 mg, 8.92 mmol, 1.24 mL) at 0° C. The mixture was allowed to warm up to room temperature and left stirring for 2 h. The reaction was diluted with water and extracted twice with dichloromethane. The organic layer was washed with brine, dried over sodium sulfate and concentrated to give N-(6-fluoropyridin-3-yl)cyclopropanecarboxamide (850 mg crude). LCMS: m/z=181.0 $[M+H]^+$, retention time 1.577 min (Method A). The product was pure enough and used directly to the next step.

N-(6-hydrazineylpyridin-3-yl)cyclopropanecarboxamide

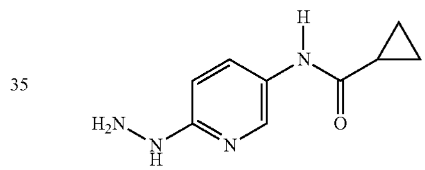

A mixture of N-(6-fluoropyridin-3-yl)cyclopropanecarboxamide (850.0 mg, 4.72 mmol) in ethanol (5.0 mL) and hydrazine hydrate (5.0 mL, 85% in water) was stirred at 110° C. for 3 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford N-(6-hydrazineylpyridin-3-yl)cyclopropane carboxamide (312 mg crude). LCMS: m/z=193.0 $[M+H]^+$, retention time 0.867 min (Method A). The product was pure enough and used directly to the next step.

N-(6-(4-(4-cyanophenyl)-5-hydroxy-1H-pyrazol-1-yl)pyridin-3-yl)cyclopropane carboxamide

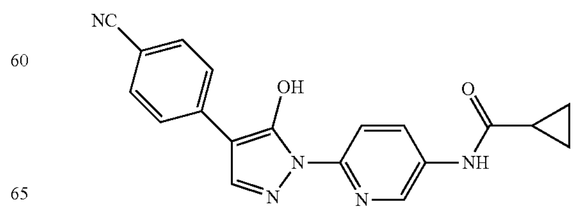

To a solution of methyl (E)-2-(4-cyanophenyl)-3-(dimethylamino)acrylate (200.0 mg, 0.87 mmol) and N-(6-hydrazineylpyridin-3-yl)cyclopropanecarboxamide (166.9 mg, 0.87 mmol) in ethanol (4.0 mL) was added p-toluenesulfonic acid monohydrate (17.1 mg, 0.09 mmol). The mixture was stirred at 90° C. for 3 h, cooled to room temperature and evaporated to dryness. The residue was purified by flash chromatography (dichloromethane/methanol=20/1) to give N-(6-(4-(4-cyanophenyl)-5-hydroxy-1H-pyrazol-1-yl)pyridin-3-yl)-cyclopropanecarboxamide (78 mg, 0.22 mmol, 26% yield) as yellow solid. LCMS: m/z=346.0 [M+H]$^+$, retention time 4.330 min (Method A). $^1$H NMR (400 MHz, DMSO-$d_6$) δ 10.56 (s, 1H), 8.77 (d, J=2.4 Hz, 1H), 8.51-8.44 (m, 1H), 8.27-8.24 (m, 1H), 8.17-8.13 (m, 1H), 8.09 (d, J=8.0 Hz, 2H), 7.78 (d, J=8.4 Hz, 2H), 1.82-1.78 (m, 1H), 0.85 (d, J=6.0 Hz, 4H).

Example 23: Preparation of Compound 23

N-(6-fluoropyridin-3-yl)propionamide

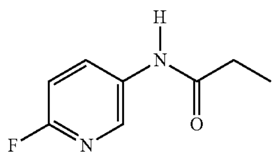

To a solution of 6-fluoropyridin-3-amine (500.0 mg, 4.46 mmol) in dichloromethane (20 mL) was added propionyl chloride (495.16 mg, 5.35 mmol, 0.47 mL) and triethylamine (902.60 mg, 8.92 mmol, 1.24 mL) at 0° C. The mixture was allowed to warm up to room temperature and stirred for 2 h. The reaction was diluted with water and extracted with dichloromethane. The organic layer was washed with brine, dried over sodium sulfate and concentrated to afford N-(6-fluoropyridin-3-yl)propionamide (808 mg crude). LCMS: m/z=169.0 [M+H]$^+$, retention time 1.498 min (Method A). The product was pure enough and used directly to the next step.

N-(6-hydrazineylpyridin-3-yl)propionamide

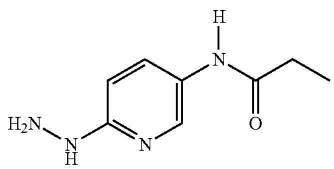

A mixture of N-(6-fluoropyridin-3-yl)propionamide (800.00 mg, 4.76 mmol) in ethanol (5 mL) and hydrazine hydrate (5.0 mL, 85% in water) was stirred at 110° C. for 3 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford N-(6-hydrazineylpyridin-3-yl)propionamide (294 mg crude). LCMS: m/z=181.0 [M+H]$^+$, retention time 0.317 min (Method A). The product was pure enough and used directly to the next step.

N-(6-(4-(4-cyanophenyl)-5-hydroxy-1H-pyrazol-1-yl)pyridin-3-yl)propionamide

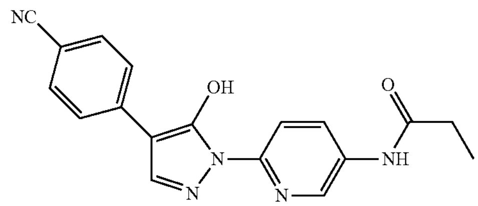 [SMILES: CCC(=O)Nc1ccc(-n2ncc(-c3ccc(C#N)cc3)c2O)nc1]

To a solution of methyl (E)-2-(4-cyanophenyl)-3-(dimethylamino)acrylate (200.0 mg, 0.87 mmol) and N-(6-hydrazineylpyridin-3-yl)propionamide (156.5 mg, 0.87 mmol) in ethanol (4.0 mL) was added p-toluenesulfonic acid monohydrate (14.9 mg, 0.09 mmol). The mixture was stirred at 90° C. for 3 h, cooled to room temperature and evaporated to dryness. The residue was purified by flash chromatography (dichloromethane/methanol=20/1) to give N-(6-(4-(4-cyanophenyl)-5-hydroxy-1H-pyrazol-1-yl)pyridin-3-yl)propionamide (23 mg, 0.07 mmol, 8.0% yield) as yellow solid. LCMS: m/z=334.0 [M+H]$^+$, retention time 4.322 min (Method A). $^1$H NMR (400 MHz, DMSO-$d_6$) δ 10.23 (s, 1H), 8.78 (s, 1H), 8.51-8.44 (m, 1H), 8.26-8.21 (m, 1H), 8.18-8.15 (m, 1H), 8.09 (d, J=8.0 Hz, 2H), 7.78 (d, J=8.4 Hz, 2H), 2.37 (q, J=7.6 Hz, 2H), 1.58 (t, J=7.6 Hz, 3H).

Example 24: Preparation of Compound 24

N-(6-fluoropyridin-3-yl)methanesulfonamide

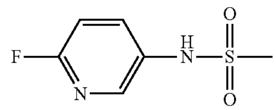

To a solution of 6-fluoropyridin-3-amine (500 mg, 4.46 mmol) in pyridine (2.5 mL) was added methanesulfonyl chloride (0.5 mL) at 0° C. The mixture was allowed to warm up to room temperature and stirred for another one hour. The reaction was diluted with water and extracted twice with ethyl acetate. The organic layer was washed with brine, dried over sodium sulfate and concentrated to give N-(6-fluoropyridin-3-yl)methane sulfonamide (600 mg, 3.12 mmol, 70% yield) as yellow oil. LCMS: m/z=190.9 [M+H]$^+$, retention time 1.38 min (Method A).

N-(6-hydrazineylpyridin-3-yl)methanesulfonamide

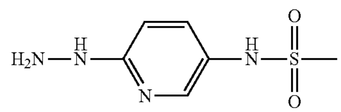

To a solution of N-(6-fluoropyridin-3-yl)methanesulfonamide (600 mg, 3.15 mmol) in ethanol (4.0 mL) was added hydrazine hydrate (2.0 mL, 85% in water). The mixture was stirred at 110° C. overnight in a sealed tube. The mixture was cooled and concentrated to dryness. The residue was partitioned between ethyl acetate and water. The organic layer was washed with brine, dried over sodium sulfate and concentrated to give N-(6-hydrazineylpyridin-3-yl)methanesulfonamide (300 mg, 1.48 mmol, 47% yield) as yellow oil. LCMS: m/z=203.2 $[M+H]^+$, retention time 0.34 min (Method A). The product was pure enough and used directly to the next step N-(6-(4-(4-cyanophenyl)-5-hydroxy-TH-pyrazol-1-yl)pyridin-3-yl)methanesulfonamide

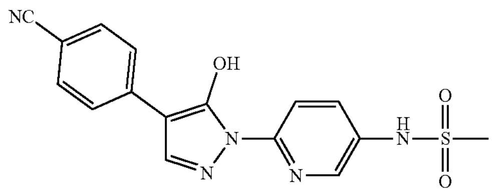 [SMILES: CS(=O)(=O)Nc1ccc(-n2ncc(-c3ccc(C#N)cc3)c2O)nc1]

To a solution of methyl (E)-2-(4-cyanophenyl)-3-(dimethylamino)acrylate (341 mg, 1.48 mmol) and N-(6-hydrazineylpyridin-3-yl)methanesulfonamide (300 mg, 1.48 mmol) in ethanol (4.0 mL) was added p-toluenesulfonic acid monohydrate (28.5 mg, 0.15 mmol). The mixture was stirred at reflux for 12 hr and cooled to precipitate solid. The solid was filtered, washed with ethanol and dried to give N-(6-(4-(4-cyanophenyl)-5-hydroxy-1H-pyrazol-1-yl)pyridin-3-yl)methanesulfonamide (250 mg, 0.72 mmol, 49% yield) as white solid. LCMS: m/z=356.4 $(M+H)^+$, retention time 3.74 min (Method A). $^1$H NMR (500 MHz, DMSO-$d_6$) δ 10.03 (s, 1H), 8.51 (s, 1H), 8.32 (d, J=13.4 Hz, 2H), 8.11 (d, J=7.8 Hz, 2H), 7.86 (d, J=8.1 Hz, 1H), 7.77 (d, J=7.9 Hz, 2H), 3.08 (s, 3H).

Example 25: Preparation of Compound 25

N-(6-fluoropyridin-3-yl)ethanesulfonamide

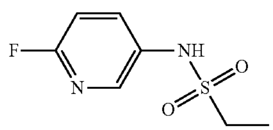

To a solution of 6-fluoropyridin-3-amine (500 mg, 4.46 mmol) in pyridine (5.0 mL) was added ethanesulfonyl chloride (689.71 mg, 5.36 mmol) at 0° C. The mixture was allowed to warm up to room temperature and left stirring for another one hour. The reaction was diluted with water and extracted twice with ethyl acetate. The organic layer was washed with brine, dried over sodium sulfate and concentrated to give N-(6-fluoropyridin-3-yl)ethanesulfonamide (900 mg, 4.38 mmol, 98.26% yield) as white solid. LCMS: m/z=205.1 $[M+H]^+$, retention time 1.32 min (Method A).

N-(6-hydrazineylpyridin-3-yl)ethanesulfonamide

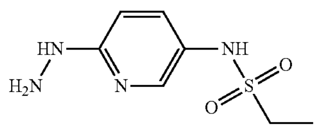

To a solution of N-(6-fluoropyridin-3-yl)ethanesulfonamide (910 mg, 4.46 mmol) in ethanol (5.0 mL) was added hydrazine hydrate (1.05 g, 17.84 mmol, 85% in water). The mixture was stirred at 100° C. for 4 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford N-(6-hydrazineylpyridin-3-yl)ethanesulfonamide (810.0 mg, 3.75 mmol, 84.11%) as white solid. LCMS: m/z=217.0 $(M+H)^+$, retention time 0.36 min (Method A).

N-(6-(4-(4-cyanophenyl)-5-hydroxy-1H-pyrazol-1-yl)pyridin-3-yl)ethanesulfonamide

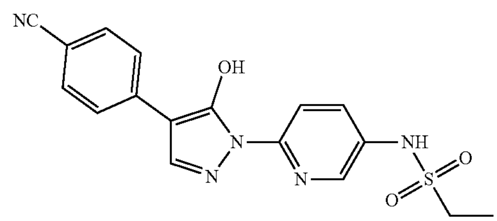 [SMILES: CCS(=O)(=O)Nc1ccc(-n2ncc(-c3ccc(C#N)cc3)c2O)nc1]

To a solution of methyl (E)-2-(4-cyanophenyl)-3-(dimethylamino)acrylate (212.96 mg, 0.93 mmol) and N-(6-hydrazinylpyridin-3-yl)ethanesulfonamide (200.00 mg, 0.93 mmol) in ethanol (5.0 mL) was added p-toluenesulfonic acid monohydrate (36.1 mg, 0.19 mmol). The mixture was stirred at reflux for 12 hr and cooled to precipitate solid. The solid was filtered, washed with ethanol and dried to give N-(6-(4-(4-cyanophenyl)-5-hydroxy-1H-pyrazol-1-yl)pyridin-3-yl)ethanesulfonamide (75 mg, 0.20 mmol, 21.86%) as white solid. LCMS: m/z=370.0 $(M+H)^+$, retention time 4.01 min (Method A). $^1$H NMR (400 MHz, DMSO-$d_6$) δ 10.13 (s, 1H), 8.55 (s, 1H), 8.34 (s, 1H), 8.32-8.18 (m, 1H), 8.11 (d, J=7.5 Hz, 2H), 7.86 (dd, J=9.0, 2.5 Hz, 1H), 7.79 (d, J=8.4 Hz, 2H), 3.18 (dd, J=14.6, 7.3 Hz, 2H), 1.24 (t, J=7.3 Hz, 3H).

Example 26: Preparation of Compound 26

2-chloro-5-(methylthio)pyridine

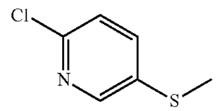

To a solution of 5-bromo-2-chloropyridine (1.92 g, 10.0 mmol) and N,N,N',N'-tetramethylethylenediamine (1.51 g, 13.0 mmol) in anhydrous tetrahydrofuran (15.0 mL) was added n-butyllithium (7.5 mL, 12.0 mmol, 1.6M in hexane) at −78° C. under nitrogen. The mixture was stirred at −78° C. for 50 min and dimethyldisulfide (1.13 g, 12.0 mmol) was added. The mixture was allowed to warm up to 20° C. and left stirring for another one hour. The reaction was quenched with saturated ammonium chloride solution and extracted twice with ethyl acetate. The organic layer was separated, washed with brine, dried over sodium sulfate and concentrated under reduced pressure. The crude product was purified by flash chromatography (petroleum ether/ethyl acetate=50/1) to obtain 2-chloro-5-(methylthio)pyridine (1.0 g, 6.29 mmol, 62.9% yield) as yellow oil. LC-MS: m/z=160 $(M+H)^+$, retention time 0.85 min (Method A).

2-chloro-5-(methylsulfinyl)pyridine

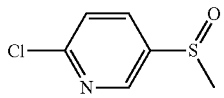

To a solution of 2-chloro-5-(methylthio)pyridine (900 mg, 5.66 mmol) in dichloromethane (10.0 mL) was added 3-chloroperoxybenzoic acid (1.26 g, 6.22 mmol, 85%) at 0° C. The mixture was stirred at this temperature for 1 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=2/1) to obtain 2-chloro-5-(methylsulfinyl)pyridine (700 mg, 4.0 mmol, 70.6% yield) as white solid. LC-MS: m/z=176.1 $(M+H)^+$, retention time 0.55 min (Method A).

2-hydrazineyl-5-(methylsulfinyl)pyridine

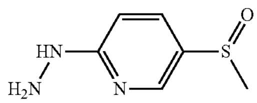

To a solution of 2-chloro-5-(methylsulfinyl)pyridine (700 mg, 4.0 mmol) in ethanol (10.0 mL) was added hydrazine hydrate (1.23 g, 20.0 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford 2-hydrazineyl-5-(methylsulfinyl)pyridine (400 mg, 2.34 mmol, 58.5% yield) as yellow solid. LC-MS: m/z=172.0 $(M+H)^+$, retention time 0.38 min (Method A).

(6-chloropyridin-3-yl)(imino)(methyl)-$\lambda^6$-sulfanone

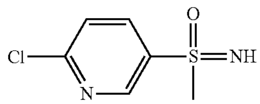

To a mixture of 2-chloro-5-(methylsulfinyl)pyridine (200 mg, 1.14 mmol) (Intermediate for Example 12) and sodium azide (223 mg, 3.43 mmol) in chloroform (5.0 mL) was added concentrated sulfuric acid (1.0 mL) at 0° C. The mixture was stirred at 55° C. for 16.0 h and cooled. The reaction was diluted with ice-water and the organic layer removed. The aqueous phase was made basic by addition of ammonium hydroxide solution whereupon an oil separated, which was extracted with dichloromethane. The organic layer was separated, washed with brine, dried over sodium sulfate and concentrated to afford (6-chloropyridin-3-yl)(imino)(methyl)-$\lambda^6$-sulfanone (120 mg, 0.63 mmol, 55.4% yield) as yellow solid. LC-MS: m/z=191.0 $(M+H)^+$, retention time 1.3 min (Method A).

(6-hydrazineylpyridin-3-yl)(imino)(methyl)-$\kappa^6$-sulfanone

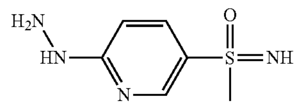

To a solution of (6-chloropyridin-3-yl)(imino)(methyl)-$\lambda^6$-sulfanone (120 mg, 0.63 mmol) in ethanol (10.0 mL) was added hydrazine hydrate (200 mg, 3.15 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (6-hydrazineylpyridin-3-yl)(imino)(methyl)-$\lambda^6$-sulfanone (100 mg, 0.54 mmol, 85.3% yield) as yellow solid. LC-MS: m/z=187.0 $(M+H)^+$, retention time 0.36 min (Method A).

4-(5-hydroxy-1-(5-(S-methylsulfonimidoyl)pyridin-2-yl)-1H-pyrazol-4-yl)benzonitrile

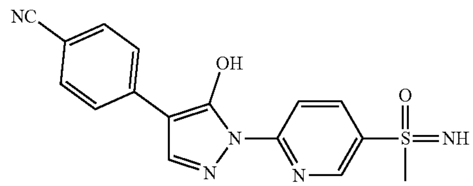 [SMILES: CS(=N)(=O)c1ccc(-n2ncc(-c3ccc(C#N)cc3)c2O)nc1]

To a solution of methyl (E)-2-(4-cyanophenyl)-3-(dimethylamino)acrylate (150 mg, 0.65 mmol) and (6-hydrazineylpyridin-3-yl)(imino)(methyl)-$\lambda^6$-sulfanone (121 mg, 0.65 mmol) in ethanol (6.0 mL) was added p-toluenesulfonic acid monohydrate (24.7 mg, 0.13 mmol). The mixture was stirred at 90° C. in a sealed tube overnight and cooled to precipitate solid. The solid was filtered, washed with ethanol and dried to give 4-(5-hydroxy-1-(5-(S-methylsulfonimidoyl)pyridin-2-yl)-1H-pyrazol-4-yl)benzonitrile (Formate) (14 mg, 0.04 mmol, 5.5% yield) as white solid. LC-MS: m/z=340.0 $(M+H)^+$, retention time 3.50 min (Method A). $^1$HNMR (400 MHz, DMSO-$d_6$) δ 8.90 (s, 1H), 8.61-8.63 (m, 1H), 8.30-8.33 (m, 2H), 8.14 (s, 1H), 8.03-8.05 (d, J=7.4 Hz, 2H), 7.61-7.63 (d, J=8.9 Hz, 2H), 3.13 (s, 3H).

Example 27: Preparation of Compound 27

6-(4-(4-cyanophenyl)-5-hydroxy-1H-pyrazol-1-yl)-N-(methylsulfonyl) nicotinamide

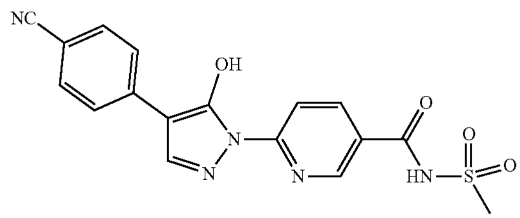 [SMILES: CS(=O)(=O)NC(=O)c1ccc(-n2ncc(-c3ccc(C#N)cc3)c2O)nc1]

To a solution of methanesulfonamide (35.3 mg, 0.37 mmol) and triethylamine (74.9 mg, 0.74 mmol) in dichloromethane (5.0 mL) was added 6-(4-(4-cyanophenyl)-5-hydroxy-1H-pyrazol-1-yl)nicotinoyl chloride (Intermediate for Example 1) (100 mg, 0.31 mmol) at 0° C. The mixture was stirred at room temperature overnight and concentrated to give dryness. The residue was purified by reverse prep-HPLC to obtain 6-(4-(4-cyanophenyl)-5-hydroxy-1H-pyrazol-1-yl)-N-(methylsulfonyl) nicotinamide (17.6 mg, 0.05 mmol, 6.2% yield) as white solid. LC-MS: m/z=384.1 $(M+H)^+$, retention time 4.24 min (Method A). $^1$HNMR (400 MHz, DMSO-$d_6$) δ 8.28-8.20 (m, 3H), 8.01-7.99 (m, 4H), 7.55-7.50 (m, 2H), 2.89 (s, 3H).

Example 28: Preparation of Compound 28 tert-butyl 6-(4-(4-cyanophenyl)-5-methoxy-1H-pyrazol-1-yl)nicotinate

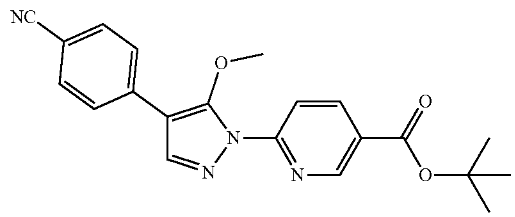 [SMILES: COc1c(-c2ccc(C#N)cc2)cnn1-c1ccc(C(=O)OC(C)(C)C)cn1]

To a solution of tert-butyl 6-(4-(4-cyanophenyl)-5-hydroxy-1H-pyrazol-1-yl)nicotinate (Intermediate for Example 1) (1.0 g, 2.76 mmol) in dichloromethane/methanol (29.0 mL/5.0 mL) was added (diazomethyl)trimethylsilane (2.07 mL, 4.14 mmol, 2M in hexane). The mixture was stirred at 25° C. overnight and concentrated to give dryness. The residue was purified by flash chromatography (petroleum ether/ethyl acetate=3/1) to obtain tert-butyl 6-(4-(4-cyanophenyl)-5-methoxy-1H-pyrazol-1-yl)nicotinate (200 mg, 0.53 mmol, 19.2% yield) as yellow solid. LC-MS: m/z=377.0 $[M+H]^+$, retention time 2.40 min (Method A).

6-(4-(4-cyanophenyl)-5-methoxy-1H-pyrazol-1-yl) nicotinic acid

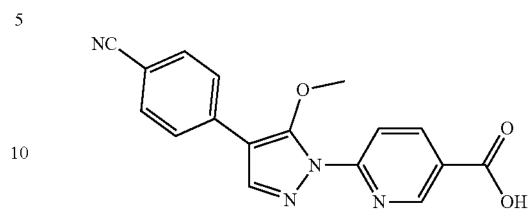

To a solution of tert-butyl 6-(4-(4-cyanophenyl)-5-methoxy-1H-pyrazol-1-yl)nicotinate (200 mg, 0.53 mmol) in dichloromethane (10.0 mL) was added trifluoroacetic acid (5.0 mL). The mixture was stirred at 40° C. for 2.0 h and concentrated. The residue was triturated with ethyl acetate and filtered to afford 6-(4-(4-cyanophenyl)-5-methoxy-1H-pyrazol-1-yl)nicotinic acid (150 mg, 0.47 mmol, 88.4% yield) as yellow solid. LC-MS: m/z=321.0 $(M+H)^+$, retention time 1.98 min (Method A).

4-(1-(5-isocyanatopyridin-2-yl)-5-methoxy-1H-pyrazol-4-yl)benzonitrile

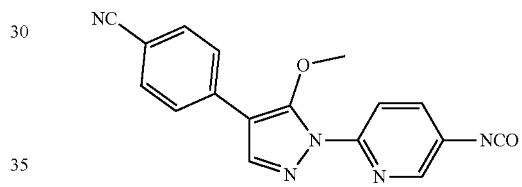

A mixture of 6-(4-(4-cyanophenyl)-5-methoxy-1H-pyrazol-1-yl)nicotinic acid (150 mg, 0.47 mmol), diphenylphosphonic azide (194 mg, 0.71 mmol) and triethylamine (95 mg, 0.94 mmol) in toluene (5.0 mL) was stirred at 110° C. for 3H. The reaction was diluted with water and extracted with ethyl acetate. The organic layer was separated, washed with brine, dried over sodium sulfate and concentrated under reduced pressure. The crude 4-(1-(5-isocyanatopyridin-2-yl)-5-methoxy-1H-pyrazol-4-yl)benzonitrile (150 mg, crude) was obtained as yellow syrup. LC-MS: m/z=345.9 $(M+H)^+$, retention time 2.01 min (Method A). The crude product was used to the next step.

N-(6-(4-(4-cyanophenyl)-5-methoxy-1H-pyrazol-1-yl)pyridin-3-yl)morpholine-4-carboxamide

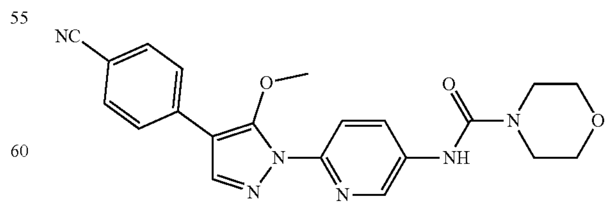

A mixture of 4-(1-(5-isocyanatopyridin-2-yl)-5-methoxy-TH-pyrazol-4-yl)benzonitrile (150 mg, crude) and morpholine (174 mg, 2.0 mmol) in dichloromethane (5.0 mL) was stirred at room temperature overnight. The reaction was diluted with water and extracted with dichloromethane. The organic layer was separated, washed with brine, dried over sodium sulfate and concentrated to give dryness. The residue was purified by flash chromatography (methanol/dichloromethane=1/10) to afford N-(6-(4-(4-cyanophenyl)-5-methoxy-1H-pyrazol-1-yl)pyridin-3-yl)morpholine-4-carboxamide (50 mg, 0.12 mmol, 26.3% yield) as yellow solid. LC-MS: m/z=405.1 $[M+H]^+$, retention time 1.96 min (Method A). The product was used to the next step.

N-(6-(4-(4-cyanophenyl)-5-hydroxy-TH-pyrazol-1-yl)pyridin-3-yl)morpholine-4-carboxamide

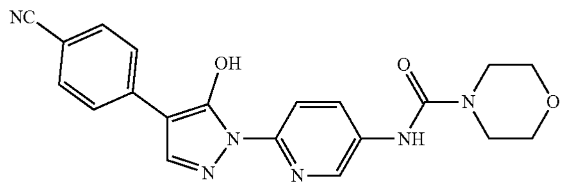 [SMILES: N#Cc1ccc(-c2cnn(-c3ccc(NC(=O)N4CCOCC4)cn3)c2O)cc1]

To a solution of N-(6-(4-(4-cyanophenyl)-5-methoxy-TH-pyrazol-1-yl)pyridin-3-yl)morpholine-4-carboxamide (50 mg, 0.12 mmol) in N,N-dimethylformamide (6.0 mL) was added lithium chloride (50.4 mg, 1.2 mmol). The mixture was stirred at 60° C. overnight. The solution was diluted with ethyl acetate and water. The organic layer was washed with brine, dried over sodium sulfate and evaporated to give dryness. The residue was purified by reverse prep-HPLC to give N-(6-(4-(4-cyanophenyl)-5-hydroxy-TH-pyrazol-1-yl)pyridin-3-yl)morpholine-4-carboxamide (Formate) (9.7 mg, 0.02 mmol, 18.6% yield) as white solid. LC-MS: m/z=391.0 $(M+H)^+$, retention time 4.27 min (Method A). $^1$HNMR (400 MHz, DMSO-$d_6$) δ 8.87 (s, 1H), 8.64 (s, 1H), 8.37 (s, 1H), 8.17 (s, 1H), 8.08-8.03 (m, 3H), 7.74-7.72 (m, 2H), 3.63-3.62 (m, 4H), 3.47-3.45 (m, 4H).

Example 29: Preparation of Compound 29

6-hydrazineylpyridine-3-sulfonamide

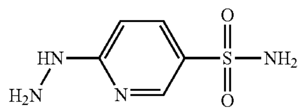 [SMILES: NNc1ccc(S(N)(=O)=O)cn1]

To a solution of 6-chloropyridine-3-sulfonamide (1.63 g, 8.5 mmol) in ethanol (5.0 mL) was added hydrazine hydrate (5.0 mL, 85% in water). The mixture was stirred at 100° C. for 4 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford 6-hydrazineylpyridine-3-sulfonamide (600 mg, 3.20 mmol, 37.7% yield) as yellow solid. LCMS: m/z=189.0 $(M+H)^+$, retention time 0.32 min (Method A).

6-(4-(4-cyanophenyl)-5-hydroxy-1H-pyrazol-1-yl)pyridine-3-sulfonamide

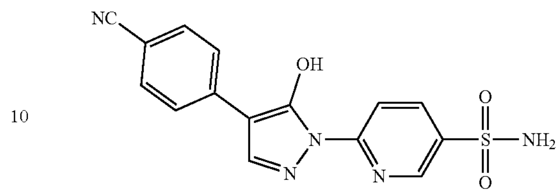

A solution of methyl (E)-2-(4-cyanophenyl)-3-(dimethylamino)acrylate (452 mg, 1.97 mmol) and 6-hydrazineylpyridine-3-sulfonamide (370 mg, 1.97 mmol) in ethanol (8.0 mL) was added p-toluenesulfonic acid monohydrate (76.4 mg, 0.4 mmol). The mixture was stirred at 90° C. for 16.0 h and cooled to precipitate solid. The solid was filtered, washed with ethanol and dried to give 6-(4-(4-cyanophenyl)-5-hydroxy-1H-pyrazol-1-yl)pyridine-3-sulfonamide (340 mg, 1.0 mmol, 50.8% yield) as white solid. LC-MS: m/z=342.0 $(M+H)^+$, retention time 1.76 min (Method A).

6-(4-(4-cyanophenyl)-5-methoxy-1H-pyrazol-1-yl)pyridine-3-sulfonamide & 6-(4-(4-cyano-phenyl)-2-methyl-5-oxo-2,5-dihydro-1H-pyrazol-1-yl)pyridine-3-sulfonamide

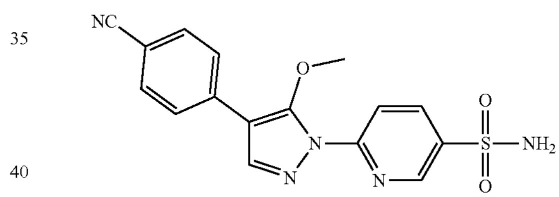

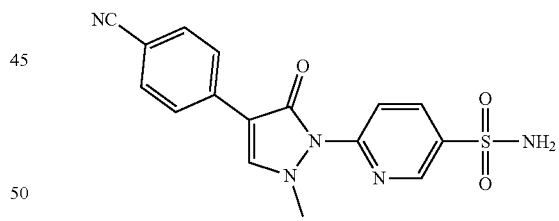

To a solution of 6-(4-(4-cyanophenyl)-5-hydroxy-1H-pyrazol-1-yl)pyridine-3-sulfonamide (340 mg, 1.0 mmol) in dichloromethane/methanol (15.0 mL/3.0 mL) was added (diazomethyl)trimethylsilane (0.75 mL, 1.5 mmol, 2M in hexane). The mixture was stirred at 25° C. overnight and concentrated to give dryness. The residue was purified by flash chromatography (dichloromethane/methanol=100/2) to obtain two isomers of 6-(4-(4-cyanophenyl)-5-methoxy-1H-pyrazol-1-yl)pyridine-3-sulfonamide and 6-(4-(4-cyano-phenyl)-2-methyl-5-oxo-2,5-dihydro-1H-pyrazol-1-yl)pyridine-3-sulfonamid (245 mg, 0.69 mmol, 69% yield) as yellow solid. LC-MS: m/z=356.0 $[M+H]^+$, retention time 1.66 min (Method A). The two isomers were used to the next step without separation.

N-((6-(4-(4-cyanophenyl)-5-methoxy-1H-pyrazol-1-yl)pyridin-3-yl)sulfonyl)acetamide & N-((6-(4-(4-cyanophenyl)-2-methyl-5-oxo-2,5-dihydro-1H-pyrazol-1-yl)pyridin-3-yl)sulfonyl)acetamide

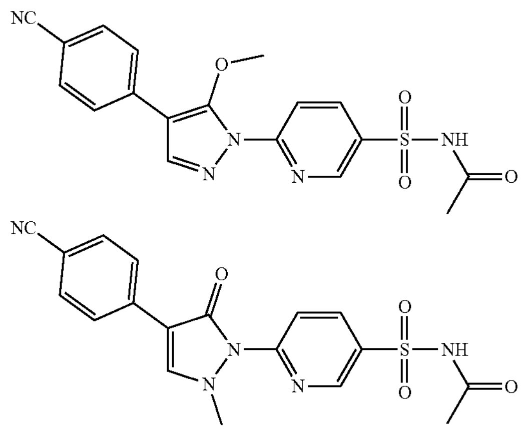

To a solution of 6-(4-(4-cyanophenyl)-5-methoxy-1H-pyrazol-1-yl)pyridine-3-sulfonamide and 6-(4-(4-cyanophenyl)-2-methyl-5-oxo-2,5-dihydro-1H-pyrazol-1-yl)pyridine-3-sulfonamid (245 mg, 0.69 mmol) in anhydrous tetrahydrofuran (10.0 mL) were added triethylamine (140 mg, 1.38 mmol) and acetyl chloride (69 mg, 0.90 mmol) at 0° C. The mixture was stirred at room temperature overnight and concentrated to give dryness. The residue was purified by flash chromatography (dichloromethane/methanol=20/1) to obtain two isomers of N-((6-(4-(4-cyanophenyl)-5-methoxy-1H-pyrazol-1-yl)pyridin-3-yl)sulfonyl)acetamide and N-((6-(4-(4-cyanophenyl)-2-methyl-5-oxo-2,5-dihydro-1H-pyrazol-1-yl)pyridin-3-yl)sulfonyl)acetamide (200 mg, 0.40 mmol, 58.3% yield) as yellow solid. LC-MS: m/z=398.0 $[M+H]^+$, retention time 1.73 min (Method A). The two isomers were used to the next step without separation.

N-((6-(4-(4-cyanophenyl)-5-hydroxy-1H-pyrazol-1-yl)pyridin-3-yl)sulfonyl)acetamide

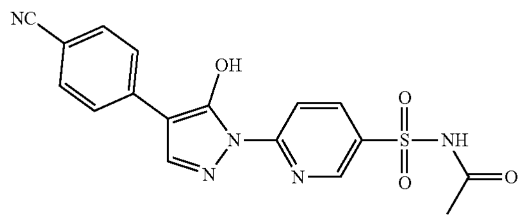 [SMILES: CC(=O)NS(=O)(=O)c1ccc(-n2ncc(-c3ccc(C#N)cc3)c2O)nc1]

To a solution of N-((6-(4-(4-cyanophenyl)-5-methoxy-1H-pyrazol-1-yl)pyridin-3-yl)sulfonyl)acetamide and N-((6-(4-(4-cyanophenyl)-2-methyl-5-oxo-2,5-dihydro-1H-pyrazol-1-yl)pyridin-3-yl)sulfonyl)acetamide (200 mg, 0.40 mmol) in N,N-dimethylformamide (10.0 mL) was added lithium chloride (168 mg, 4.0 mmol). The mixture was stirred at 60° C. overnight. The solution was diluted with ethyl acetate and water. The organic layer was washed with brine, dried over sodium sulfate and evaporated to give dryness. The residue was purified by reverse prep-HPLC to give N-((6-(4-(4-cyanophenyl)-5-hydroxy-1H-pyrazol-1-yl)pyridin-3-yl)sulfonyl)acetamide (Formate) (15.3 mg, 0.04 mmol, 8.92% yield) as white solid. LC-MS: m/z=384.0 $(M+H)^+$, retention time 3.42 min (Method A). $^1$HNMR (500 MHz, DMSO-$d_6$) δ 12.77 (br, 1H), 8.89 (s, 1H), 8.66 (d, J=8.0 Hz, 1H), 8.48 (s, 1H), 8.34 (dd, J=8.5 Hz, J=2.0 Hz, 1H), 8.09 (d, J=8.0 Hz, 2H), 7.69 (d, J=8.5 Hz, 2H), 1.93 (s, 3H).

Example 30: Preparation of Compound 30

(6-bromopyridin-3-yl)dimethylphosphine oxide

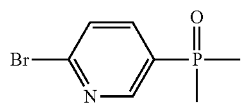

A mixture of 2-bromo-5-iodopyridine (500 mg, 1.76 mmol), dimethylphosphine oxide (275 mg 3.53 mmol), potassium phosphate (1.12 g, 5.28 mmol), 4,5-bis(diphenylphosphino)-9,9-dimethylxanthene (203 mg, 0.35 mmol) and palladium acetate (156 mg, 0.7 mmol) in 1,4-dioxane (15.0 mL) was stirred at 100° C. overnight under nitrogen. The reaction mixture was filtered with celite, and the filtrate was concentrated under reduced pressure. The obtained residue was purified by flash chromatography (petroleum ether/ethyl acetate=1/1) to afford (6-bromopyridin-3-yl)dimethylphosphine oxide (50 mg, 0.21 mmol, 12.1% yield) as yellow oil. LC-MS: m/z=234 $[M+H]^+$, retention time=1.36 min (Method A).

(6-hydrazineylpyridin-3-yl)dimethylphosphine oxide

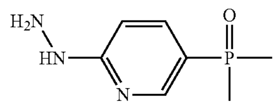

To a solution of (6-bromopyridin-3-yl)dimethylphosphine oxide (120 mg, 0.51 mmol) in ethanol (5.0 mL) was added hydrazine hydrate (160 mg, 2.55 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (6-hydrazineylpyridin-3-yl)dimethylphosphine oxide (80 mg, 0.43 mmol, 80% yield) as yellow solid. LC-MS: m/z=186.0 $(M+H)^+$, retention time 0.36 min (Method A).

4-(1-(5-(dimethylphosphoryl)pyridin-2-yl)-5-hydroxy-1H-pyrazol-4-yl)benzonitrile

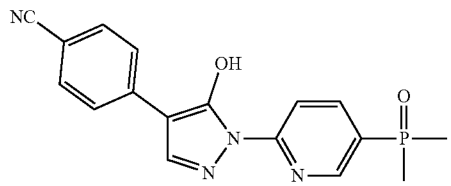 [SMILES: CP(C)(=O)c1ccc(-n2ncc(-c3ccc(C#N)cc3)c2O)nc1]

To a solution of methyl (E)-2-(4-cyanophenyl)-3-(dimethylamino)acrylate (100 mg, 0.43 mmol) and (6-hydrazineylpyridin-3-yl)dimethylphosphine oxide (80.4 mg, 0.43 mmol) in ethanol (5.0 mL) was added p-toluenesulfonic acid monohydrate (19 mg, 0.1 mmol). The mixture was stirred at 100° C. in a sealed tube overnight and cooled to precipitate solid. The solid was purified by reverse prep-HPLC to afford 4-(1-(5-(dimethylphosphoryl)pyridin-2-yl)-5-hydroxy-1H-pyrazol-4-yl)benzonitrile (Formate) (15.0 mg, 0.04 mmol, 9.3% yield) as white solid. LC-MS: m/z=339.0 $(M+H)^+$, retention time 3.48 min (Method A). $^1$HNMR (400 MHz, DMSO-$d_6$) δ 8.79-8.77 (m, 1H), 8.51-8.45 (m, 2H), 8.31-8.26 (m, 1H), 8.10-8.08 (m, 2H), 7.72-7.70 (m, 2H), 1.74-1.70 (m, 6H).

Example 31: Preparation of Compound 31

4-(5-chloropyridin-2-yl)-1-(5-(methylsulfonyl)pyridin-2-yl)-1H-pyrazol-5-ol

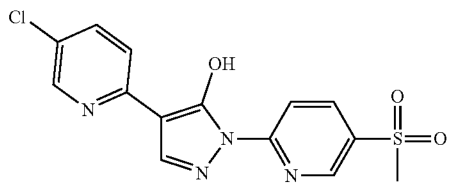 [SMILES: CS(=O)(=O)c1ccc(-n2ncc(-c3ccc(Cl)cn3)c2O)nc1]

The compound was synthesized according to the procedure for the preparation of 4-(5-hydroxy-1-(5-(methylsulfonyl)pyridin-2-yl)-1H-pyrazol-4-yl)benzonitrile (Example 4) using 5-chloropyridine-2-acetic acid. LCMS (ESI+): m/z 365 $(M+H)^+$; $^1$H NMR (300 MHz, DMSO-$d_6$) δ 8.91 (s, 1H), 8.70 (d, J=5.7 Hz, 1H), 8.55 (d, J=1.5 Hz, 1H), 8.46 (d, J=8.7 Hz, 1H), 8.27 (d, J=8.7 Hz, 1H), 7.51 (dd, J=8.7 Hz, J=2.4 Hz, 1H), 3.34 (s, 3H), 2.73 (s, 3H).

Example 32: Preparation of Compound 32

3-methyl-4-vinylbenzonitrile

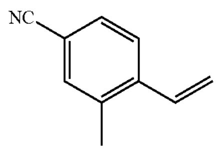

Under the nitrogen atmosphere, a mixture of 4-bromo-3-methylbenzonitrile (6.14 g, 31.34 mmol), $Cs_2CO_3$ (40.87 g, 125.38 mmol), potassium trifluoro(vinyl)borate (8.40 g, 62.69 mmol) and Pd(dppf)$Cl_2$ (2.29 g, 3.13 mmol) in THF (300 mL) and water (30 mL) was stirred at 75° C. for 6 hrs. After the reaction was completed as indicated by TLC analysis, the resulting mixture was diluted with brine (80 mL) and extracted with ethyl acetate (200 mL×2). The combined organic phase was dried over $Na_2SO_4$ (30 g), filtered and concentrated. The residue was purified by silica gel column chromatography (EtOAc:Hex=1:50) to give 6.74 g of the desired product as oil. GC-MS: m/z 143 $(M)^+$.

2-(4-cyano-2-methylphenyl)acetic acid

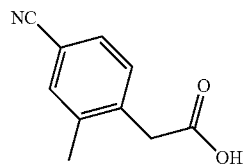

A mixture of 3-methyl-4-vinylbenzonitrile (6.74 g, 47.13 mmol) and 12 (1.20 g, 4.71 mmol) in DME (400 mL) and water (96 mL) was stirred at rt for 5 min. Oxone (57.97 g, 94.26 mmol) was added in portion. The reaction was stirred at rt overnight. After the reaction was completed as indicated by TLC analysis, the resulting mixture was diluted with an aqueous $Na_2S_2O_3$ solution (100 mL) and extracted with ethyl acetate (50 mL×5). The combined organic phase was dried over $Na_2SO_4$ (30 g), filtered and concentrated. The residue was purified by slurry to give 3.4 g of the crude product as solid, which was used for the next step directly without further purification.

methyl 2-(4-cyano-2-methylphenyl)acetate

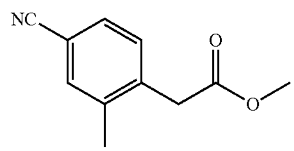

A mixture of 2-(4-cyano-2-methylphenyl)acetic acid (3.40 g, 21.66 mmol) in MeOH (60 mL) was added $SOCl_2$ (7 mL) dropwise over 5 min. The mixture was stirred at rt for 40 min. After the reaction was completed as indicated by TLC analysis, the resulting mixture was concentrated directly. The residue was purified by silica gel column chromatography (EtOAc: n-Hex=1:50 to 1:10) to give 1.66 g of the desired product as oil. $^1$H-NMR (300 MHz, $CDCl_3$) δ 7.46 (m, 2H), 7.30 (d, J=8.1 Hz, 1H), 3.71 (s, 3H), 3.69 (s, 2H), 2.34 (s, 3H).

methyl (Z)-2-(4-cyano-2-methylphenyl)-3-(dimethylamino)acrylate

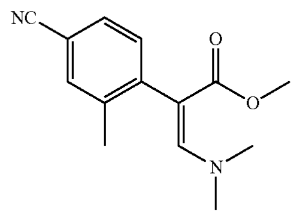 [SMILES: COC(=O)/C(=C\N(C)C)c1ccc(C#N)cc1C]

A mixture of methyl 2-(4-cyano-2-methylphenyl)acetate (1.66 g, 8.78 mmol) in DMF-DMA (6 mL) was stirred at 100° C. for 5 hrs. After the reaction was completed as indicated by TLC analysis, the resulting mixture was concentrated directly. The residue was purified by silica gel column chromatography (EtOAc: n-Hex=1:50 to 1:5) to give 2.0 g of the desired product as oil. LCMS (ESI+): m/z 245 $(M+H)^+$; $^1$H-NMR (300 MHz, $CDCl_3$) δ 7.61 (s, 1H), 7.46 (s, 1H), 7.42 (d, J=8.1 Hz, 1H), 7.22 (d, J=8.1 Hz, 1H), 3.61 (s, 3H), 2.66 (s, 6H), 2.22 (s, 3H).

4-(5-hydroxy-1H-pyrazol-4-yl)-3-methylbenzonitrile

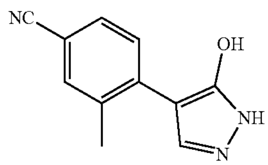

To a solution of methyl (Z)-2-(4-cyano-2-methylphenyl)-3-(dimethylamino)acrylate (0.34 g, 1.39 mmol) in EtOH (10 mL) was added $N_2H_4 \cdot H_2O$ (0.64 g, 10.20 mmol). The reaction was stirred at 70° C. overnight. After the reaction was completed as indicated by TLC, the resulting mixture was concentrated directly. The residue was purified by silica gel column chromatography (EtOAc: n-Hex=1:50 to 1:10) to give 287 mg of the desired product as oil. $^1$H-NMR (300 MHz, DMSO-$d_6$) δ 11.96 (brs, 1H), 10.21 (brs, 1H), 7.74 (s, 1H), 7.67 (s, 1H), 7.62 (d, J=8.1 Hz, 2H), 2.36 (s, 3H).

2,3-dichloro-5-(methylthio)pyridine

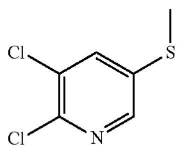

A mixture of 5,6-dichloropyridin-3-amine (0.50 g, 3.07 mmol) in conc HCl (2.5 mL) at 0° C. was added an aqueous $NaNO_2$ solution (0.32 g, 4.60 mmol, 1 mL of water) dropwise over 5 min. The reaction was stirred at 0° C. for 1 hr. The reaction was filtered to remove the inorganic salt. The solution was added to a suspension of MeSNa (1.29 g, 3.68 mmol, 20%) and $NaBF_4$ (3.4 mg, 0.031 mmol) in acetonitrile (2.5 ml) at 0° C. dropwise over 10 min. The resulting orange suspension was stirred at rt for 2 hrs. After the reaction was completed as indicated by TLC, the reaction was quenched with an aqueous NaOH solution (1N, 5 mL) and extracted with ethyl acetate (3×50 mL). The combined organic phase was dried over $Na_2SO_4$ (20 g), filtered and concentrated to give 456 mg of the desired product as black solid. $^1$H-NMR (300 MHz, $CDCl_3$) δ 8.15 (d, J=2.1 Hz, 1H), 7.62 (d, J=2.4 Hz, 1H), 2.50 (d, J=6.0 Hz, 3H).

2,3-dichloro-5-(methylsulfonyl)pyridine

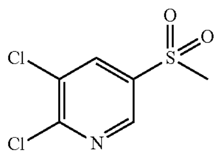

To a solution of 2,3-dichloro-5-(methylthio)pyridine (0.46 g, 2.35 mmol) in DCM (30 mL) was added m-CPBA (0.85 g, 4.94 mmol) in one portion. Then the reaction was stirred at rt for 3.5 hrs. After the reaction was completed as indicated by TLC, the mixture was concentrated directly. The residue in EtOAc (50 mL) was washed with an aqueous $Na_2S_2O_3$ solution (10 mL). The aqueous phase was extracted with EtOAc (2×50 mL). The combined organic phase was dried over $Na_2SO_4$ (30 g), filtered and concentrated. The residue was purified by silica gel column chromatography (EtOAc: n-Hex=1:50 to 1:20) to give 460 mg of the desired product as solid. $^1$H-NMR (300 MHz, $CDCl_3$) δ 8.82 (d, J=2.1 Hz, 1H), 8.29 (d, J=2.4 Hz, 1H), 3.15 (s, 3H).

4-(1-(3-chloro-5-(methylsulfonyl)pyridin-2-yl)-5-hydroxy-1H-pyrazol-4-yl)-3-methylbenzonitrile

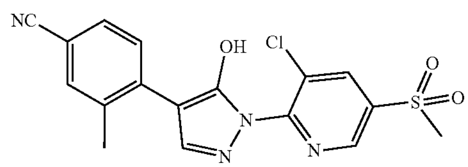 [SMILES: Cc1cc(C#N)ccc1-c1cnn(-c2ncc(S(C)(=O)=O)cc2Cl)c1O]

A mixture of 4-(5-hydroxy-1H-pyrazol-4-yl)-3-methylbenzonitrile (0.15 g, 0.75 mmol) in DMF (3 mL) was added NaH (60 mg, 1.50 mmol) portionwise over 5 min. The reaction was stirred at rt for 40 min. 2,3-dichloro-5-(methylsulfonyl)pyridine (0.25 g, 1.13 mmol) was added and the reaction was stirred at rt overnight. After the reaction was completed as indicated by TLC analysis, the resulting mixture was concentrated to dryness directly. The residue was purified by preparative HPLC to give 11 mg of the desired product as solid. LCMS (ESI+): m/z 389 $(M+H)^+$; $^1$H-NMR (300 MHz, $CDCl_3$) δ 10.23 (brs, 1H), 8.44 (d, J=2.1 Hz, 1H), 8.18 (d, J=2.1 Hz, 1H), 7.69 (s, 1H), 7.50 (s, 1H), 7.38-7.45 (m, 2H), 3.06 (s, 3H), 2.41 (s, 3H).

Example 33: Preparation of Compound 33

N-(6-(4-(4-cyanophenyl)-5-hydroxy-1H-pyrazol-1-yl)pyridin-3-yl)piperazine-1-carboxamide

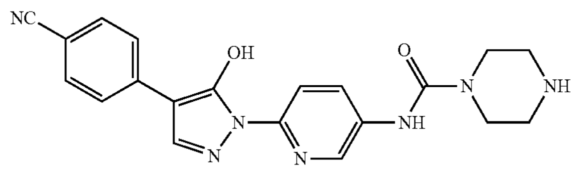 [SMILES: N#Cc1ccc(-c2cnn(-c3ccc(NC(=O)N4CCNCC4)cn3)c2O)cc1]

The compound was synthesized according to the procedure for the preparation of N-(6-(4-(4-cyanophenyl)-5-hydroxy-1H-pyrazol-1-yl)pyridin-3-yl)morpholine-4-carboxamide (Example 28) using tert-butyl piperazine-1-carboxylate.

Vitro Assays Demonstrate PHD Inhibition

Enzymatic half maximal inhibitory concentration ($IC_{50}$) values were determined on selected compounds of the invention.

Time-resolved fluorescence resonance energy transfer (TR-FRET) assay was utilized to determine the enzymatic half maximal inhibitory concentration ($IC_{50}$) value of PHD inhibitors against the full-length human prolyl-4-hydroxylase domain (PHD) enzymes, PHD1, PHD2, and PHD3. The TR-FRET assay was developed based on the specific binding of hydroxylated HIF-1α peptide with the complex formed by VHL, EloB and EloC (VBC), to generate a fluorescent signal. Terbium (Tb)-Donor (monoclonal antibody anti-6His-Tb-cryptate Gold) and D2-acceptor (streptavidin [SA]-D2) of TR-FRET are linked to the VBC complex and to HIF-1α peptide, respectively. The VBC complex binds specifically to the HIF-1α peptide when it is hydroxylated, allowing energy transfer from TR-FRET donor to acceptor (FIG. 1).

Materials and Methods

All chemicals and materials unless otherwise noted were of standard laboratory grade and were purchased from Sigma-Aldrich (St. Louis, MO, USA).

Reagents

TR-FRET Reagents

Monoclonal antibody anti-6His-Tb-cryptate Gold (catalog #61HI2TLA) and streptavidin (SA)-D2 (catalog #610SADLA) were purchased from CisBio International (Bedford, MA, USA).

N-terminus biotinylated HIF-1α C35 synthetic peptide representing amino acids 547 to 581 and including the proline 564 PHD2 hydroxylation site was purchased from California Peptide Research (Salt Lake City, UT, USA).

Recombinant Proteins

VBC Complex

His-tagged recombinant VHL protein, EloB, EloC complex (His-VBC) was supplied by Axxam (Milan, Italy). Recombinant human VHL (National Center for Biotechnology Information [NCBI] accession number NP_00542.1) contained a His tag at the C-terminus of amino acids 55 to 213 and is referred to as VHL-His. VHL-His was co-expressed in *E. coli* with full-length human EloB (NCBI accession number Q15370.1) and full-length human EloC (NCBI accession number Q15369.1) and purified by affinity chromatography on a nickel-nitrilotriacetic acid (Ni-NTA) column as the His-VBC complex. Purity (~80%) was assessed by sodium dodecyl sulfate polyacrylamide gel electrophoresis (SDS-PAGE).

PHD1

Recombinant human PHD1 protein (catalog #81064, Lot #24717001) was purchased from Active Motif (Carlsbad, CA, USA). PHD1 was expressed in a baculovirus expression system as the full-length protein (NCBI accession number NP_542770.2) with an N-terminal FLAG tag (molecular weight 44.9 kDa). Purity (>90%) was assessed by SDS-PAGE.

PHD2

The full-length human PHD2 enzyme was produced with a baculovirus infected insect cell (BIIC) expression system by Beryllium (Bedford, MA, USA). The PHD2 construct contained amino acids 1 to 426 of PHD2 (UniProt Knowledgebase[UniProtKB]/Swiss-Prot accession number Q9GZT9.1), and a His tag and a Tobacco Etch Virus (TEV) protease cleavage site at the N-terminus. The construct was expressed in Sf9 insect cells, purified by Ni-NTA column and digested with TEV protease to remove the His tag. The purity of final cleaved protein was assessed by SDS-PAGE and was found to be >94% pure.

PHD3

Recombinant human PHD3 protein (molecular weight 31.1 kDa) was purchased from Active Motif (Carlsbad, CA, USA). It was expressed in *E. coli* as the full-length protein (NCBI accession number NP_071356.1) with an N-terminal 6-His tag (catalog #81033, Lot #24417001). Purity was assessed by SDS-PAGE and was found to be >75% pure.

PHD Inhibitors.

Small molecule PHD inhibitors were synthesized and their identities were confirmed as described herein.

TR-FRET Assay Procedure

PHD inhibitor compound was preincubated with PHD enzyme in a 10 μL reaction volume in white 384-well Optiplate microplates (catalog #6007290, Perkin Elmer, Waltham, MA, USA). For this, 5 μL PHD inhibitor compound was serially diluted with dilution buffer (50 mM HEPES [4-(2-hydroxyethyl)-1-piperazineethanesulfonic acid] pH 7.5, 50 mM sodium chloride [NaCl], 0.01% Tween-20, 0.01% purified bovine serum albumin [BSA]) and mixed with 5 μL PHD enzyme mix prepared as a 4× concentrate in the dilution buffer containing PHD enzyme (60 nM PHD1, 20 nM PHD2, 140 nM PHD3), 40 μM ferrous ammonium sulfate (FAS), 4 mM sodium (Na) ascorbate. The plates were incubated for 30 minutes at room temperature without rotation.

Five microliters of the VBC/anti-6His-Tb-cryptate Gold mix prepared as a 4×concentrate in dilution buffer containing 20 nM His-VBC, 1.32 nM monoclonal antibody anti-6His-Tb-cryptate Gold was then added. This step was followed immediately by the addition of 5 μL of the HIF-1α C35 substrate mix prepared as a 4×concentrate in the dilution buffer containing 120 nM biotin-labeled HIF-1α C35, 132 nM SA-D2, 4 μM 2-oxoglutarate (2-OG) to reach a final reaction volume of 20 μL.

The final assay reaction contained 50 mM HEPES, pH 7.5, 50 mM NaCl, 1 μM 2-OG, 10 μM FAS, 1 mM Na ascorbate, 0.01% Tween-20, 0.01% purified BSA, 30 nM biotin-labeled HIF-1α C35, 5 nM His-VBC, 0.33 nM monoclonal antibody anti-6His-Tb-cryptate Gold, 33 nM SA-D2 and PHD enzyme (15 nM PHD1, 5 nM PHD2, or 35 nM PHD3) with the diluted compound.

For the measurement of the $IC_{50}$ of PHD inhibitor compound, reactions were incubated for 10 minutes at room temperature and then read on a Perkin Elmer EnVision (Waltham, MA, USA) at an excitation wavelength of 340 nm and at emission wavelengths of 615 nm and 665 nm. The data represent the quotient of the signal intensity at 665 nm and 615 nm, automatically calculated by Envision Manager software (Perkin Elmer, Waltham, MA, USA). The $IC_{50}$ values (mean, standard deviation, standard error of the mean, geometric mean and 95% confidence interval) were determined using a four-parameter curve-fit using GraphPad Prism 7.0 (GraphPad, La Jolla, CA, USA) and represent the compound concentration plotted against the calculated ratio of 665 nm and 615 nm. TR-FRET assays were performed in triplicate at each concentration of compound and the assays were repeated independently three times.

Kis were calculated from $IC_{50}$s based on the Cheng Prussoff equation:

$$Ki=IC50/(1+[2\text{-}OG]/Km)$$

The final concentration of 2-OG in both the PHD1 and PHD2 assays is 1 uM. The Km of 2-OG for PHD1 was determined to be 12.7 nM, while the Km of 2-OG for PHD2 was determined to be 22.6 nM.

Exemplary Compounds
| Cmpd. No. | Structure | PHD1 $IC_{50}$ (nM) | PHD2 $IC_{50}$ (nM) | PHD3 $IC_{50}$ (nM) |
|---|---|---|---|---|
| 1. | 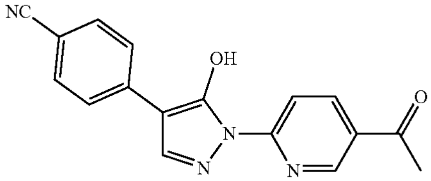 [SMILES: CC(=O)c1ccc(-n2ncc(-c3ccc(C#N)cc3)c2O)nc1] | A | A | A |
| 2. | 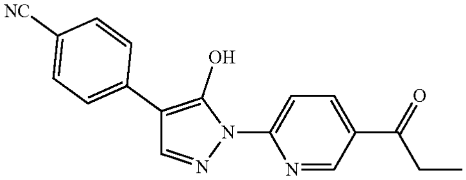 [SMILES: CCC(=O)c1ccc(-n2ncc(-c3ccc(C#N)cc3)c2O)nc1] | A | A | A |
| 3. | 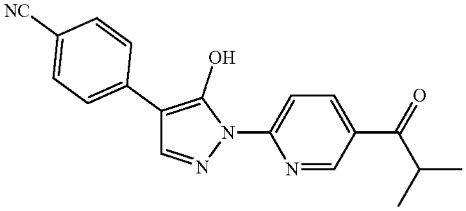 [SMILES: CC(C)C(=O)c1ccc(-n2ncc(-c3ccc(C#N)cc3)c2O)nc1] | A | A | A |
| 4. | 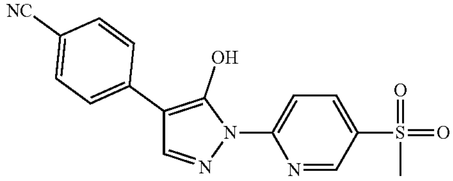 [SMILES: CS(=O)(=O)c1ccc(-n2ncc(-c3ccc(C#N)cc3)c2O)nc1] | A | A | A |
| 5. | 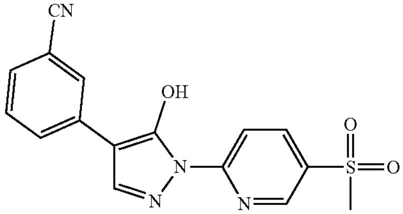 [SMILES: CS(=O)(=O)c1ccc(-n2ncc(-c3cccc(C#N)c3)c2O)nc1] | B | A | — |
| 6. | 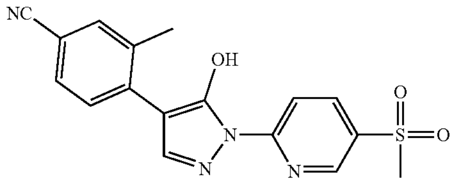 [SMILES: Cc1cc(C#N)ccc1-c1cnn(-c2ccc(S(C)(=O)=O)cn2)c1O] | A | A | A |
| 7. | 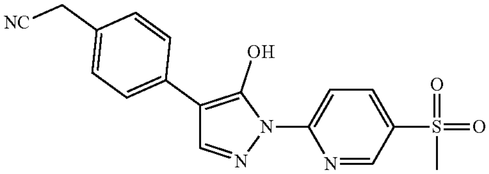 [SMILES: CS(=O)(=O)c1ccc(-n2ncc(-c3ccc(CC#N)cc3)c2O)nc1] | A | A | A |

-continued
| Cmpd. No. | Structure | PHD1 $IC_{50}$ (nM) | PHD2 $IC_{50}$ (nM) | PHD3 $IC_{50}$ (nM) |
|---|---|---|---|---|
| 8. | 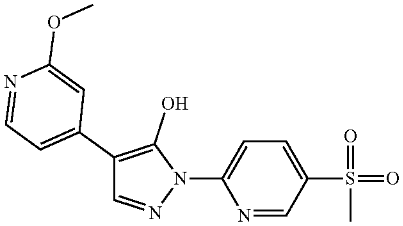 [SMILES: COc1cc(-c2cnn(-c3ccc(S(C)(=O)=O)cn3)c2O)ccn1] | A | A | B |
| 9. | 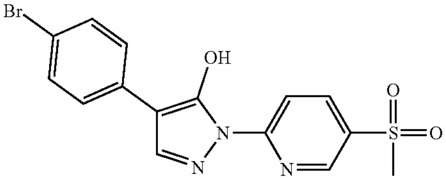 | A | A | B |
| 10. | 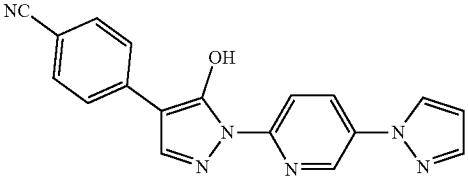 [SMILES: N#Cc1ccc(-c2cnn(-c3ccc(-n4cccn4)cn3)c2O)cc1] | A | A | B |
| 11. | 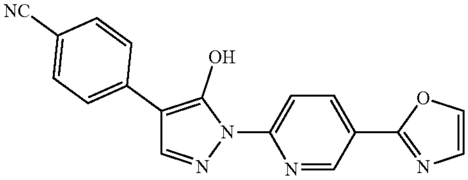 | A | A | B |
| 12. | 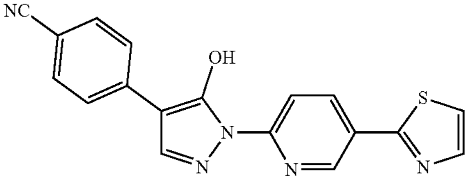 | A | A | A |
| 13. | 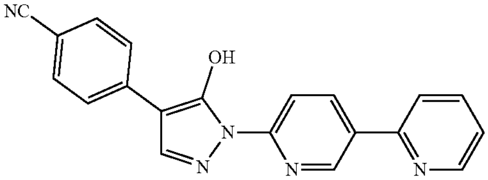 [SMILES: N#Cc1ccc(-c2cnn(-c3ccc(-c4ccccn4)cn3)c2O)cc1] | A | B | — |
| 14. | 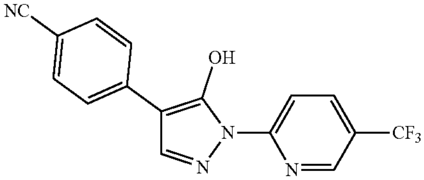 [SMILES: N#Cc1ccc(-c2cnn(-c3ccc(C(F)(F)F)cn3)c2O)cc1] | B | C | —— |

-continued
| Cmpd. No. | Structure | PHD1 $IC_{50}$ (nM) | PHD2 $IC_{50}$ (nM) | PHD3 $IC_{50}$ (nM) |
|---|---|---|---|---|
| 15. | 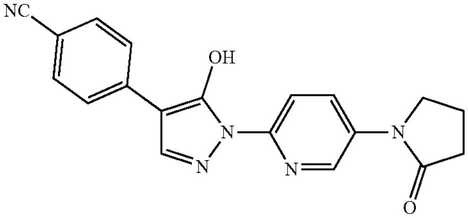 [SMILES: N#Cc1ccc(-c2cnn(-c3ccc(N4CCCC4=O)cn3)c2O)cc1] | A | A | A |
| 16. | 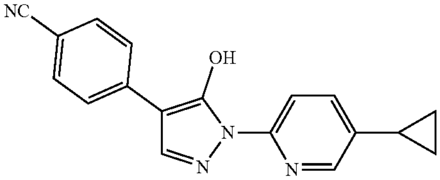 [SMILES: N#Cc1ccc(-c2cnn(-c3ccc(C4CC4)cn3)c2O)cc1] | B | D | — |
| 17. | 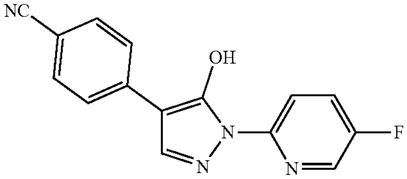 [SMILES: N#Cc1ccc(-c2cnn(-c3ccc(F)cn3)c2O)cc1] | A | A | B |
| 18. | 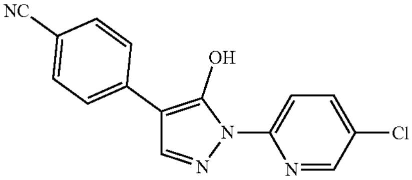 [SMILES: N#Cc1ccc(-c2cnn(-c3ccc(Cl)cn3)c2O)cc1] | B | B | — |
| 19. | 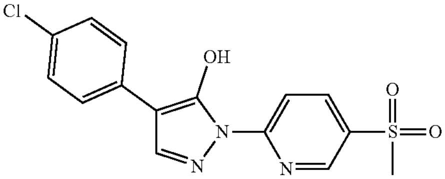 [SMILES: CS(=O)(=O)c1ccc(-n2ncc(-c3ccc(Cl)cc3)c2O)nc1] | A | A | B |
| 20. | 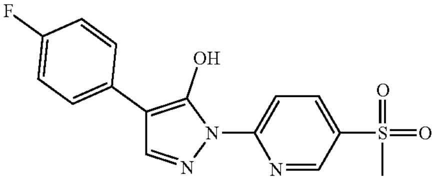 [SMILES: CS(=O)(=O)c1ccc(-n2ncc(-c3ccc(F)cc3)c2O)nc1] | A | A | D |
| 21. | 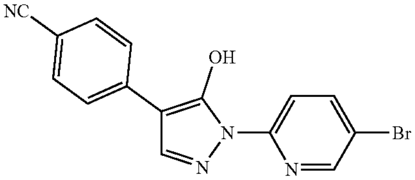 [SMILES: N#Cc1ccc(-c2cnn(-c3ccc(Br)cn3)c2O)cc1] | B | B | — |

-continued
| Cmpd. No. | Structure | PHD1 $IC_{50}$ (nM) | PHD2 $IC_{50}$ (nM) | PHD3 $IC_{50}$ (nM) |
|---|---|---|---|---|
| 22. | 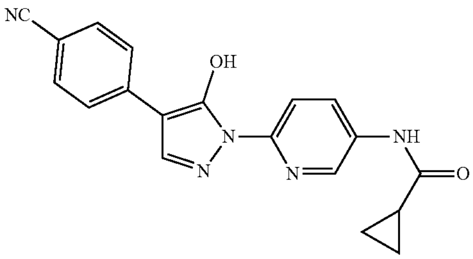 [SMILES: N#Cc1ccc(-c2cnn(-c3ccc(NC(=O)C4CC4)cn3)c2O)cc1] | A | A | B |
| 23. | 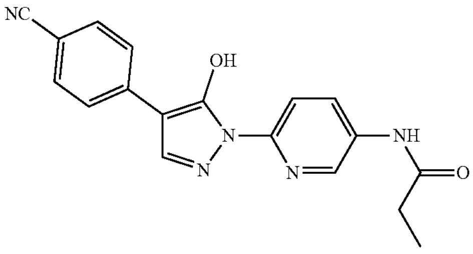 [SMILES: CCC(=O)Nc1ccc(-n2ncc(-c3ccc(C#N)cc3)c2O)nc1] | A | A | A |
| 24. | 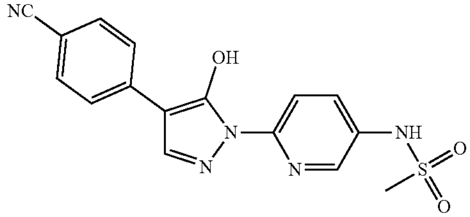 [SMILES: CS(=O)(=O)Nc1ccc(-n2ncc(-c3ccc(C#N)cc3)c2O)nc1] | A | A | A |
| 25. | 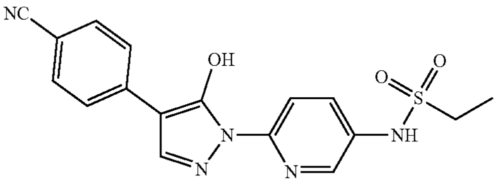 [SMILES: CCS(=O)(=O)Nc1ccc(-n2ncc(-c3ccc(C#N)cc3)c2O)nc1] | A | A | A |
| 26. | 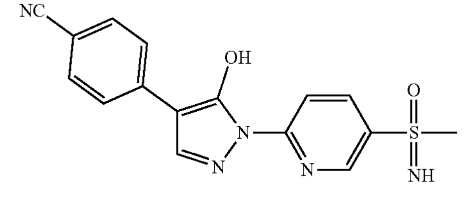 [SMILES: CS(=N)(=O)c1ccc(-n2ncc(-c3ccc(C#N)cc3)c2O)nc1] | A | A | — |
| 27. | 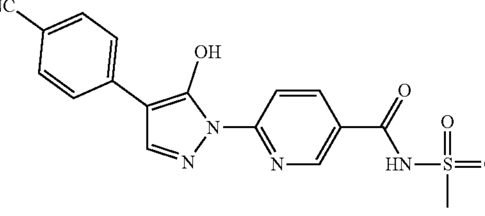 | A | A | — |
| 28. | 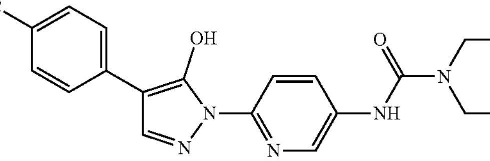 | D | D | — |

-continued
| Cmpd. No. | Structure | PHD1 $IC_{50}$ (nM) | PHD2 $IC_{50}$ (nM) | PHD3 $IC_{50}$ (nM) |
|---|---|---|---|---|
| 29. | 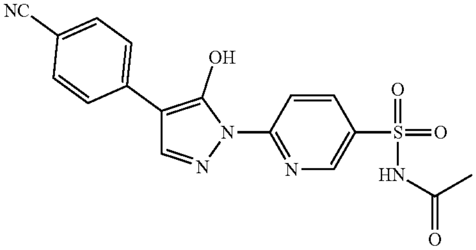 [SMILES: CC(=O)NS(=O)(=O)c1ccc(-n2ncc(-c3ccc(C#N)cc3)c2O)nc1] | A | A | — |
| 30. | 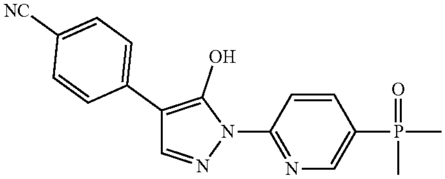 [SMILES: CP(C)(=O)c1ccc(-n2ncc(-c3ccc(C#N)cc3)c2O)nc1] | A | A | — |
| 31. | 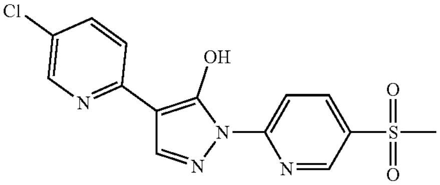 [SMILES: CS(=O)(=O)c1ccc(-n2ncc(-c3ccc(Cl)cn3)c2O)nc1] | B | B | — |
| 32. | 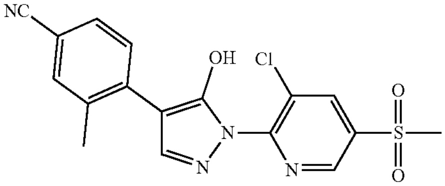 [SMILES: Cc1cc(C#N)ccc1-c1cnn(-c2ncc(S(C)(=O)=O)cc2Cl)c1O] | D | D | — |
| 33. | 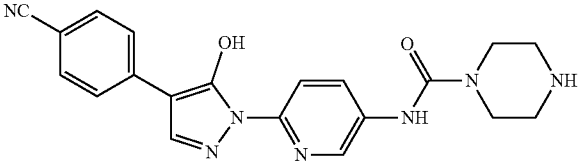 [SMILES: N#Cc1ccc(-c2cnn(-c3ccc(NC(=O)N4CCNCC4)cn3)c2O)cc1] | D | D | —— |
Legend:
A = IC50 < 100 nM
B = 100 nM ≤ IC50 < 1000 nM
C = 1000 nM ≤ IC50 < 10000 nM
D = IC50 ≥ 10000 nM From the ongoing description, one skilled in the art can easily ascertain the essential characteristics of this invention, and without departing from the spirit and scope thereof, can make various changes and modifications of the invention to adapt it to various usages and conditions.

All references, patents or applications, U.S. or foreign, cited in the application are hereby incorporated by reference as if written herein in their entireties. Where any inconsistencies arise, material literally disclosed herein controls.

The invention claimed is:

1. A compound selected from the group consisting of:

| Cmpd No. | Structure |
| --- | --- |
| 1 | 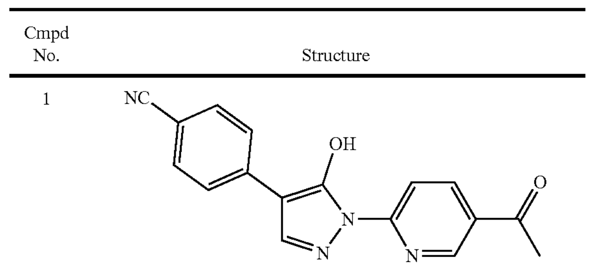 |

-continued

| Cmpd No. | Structure |
| --- | --- |
| 2 | 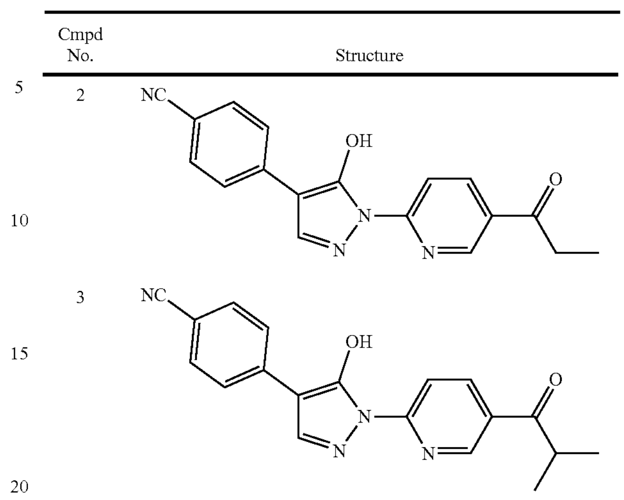 |
| 3 | |

or a pharmaceutically acceptable salt thereof.

2. A pharmaceutical composition comprising the compound of claim 1, or a pharmaceutically acceptable salt thereof, and a pharmaceutically acceptable excipient.

* * * * *